United States Patent
Moehs et al.

(10) Patent No.: US 10,801,036 B2
(45) Date of Patent: Oct. 13, 2020

(54) WHEAT HAVING RESISTANCE TO GLYPHOSATE DUE TO ALTERATIONS IN 5-ENOL-PYRUVYLSHIKIMATE-3 PHOSPHATE SYNTHASE

(71) Applicant: Arcadia Biosciences, Inc., Seattle, WA (US)

(72) Inventors: Charles Paul Moehs, Seattle, WA (US); Michael N. Steine, Kent, WA (US); Jessica C. Mullenberg, Kirkland, WA (US); Ann J. Slade, Bellevue, WA (US)

(73) Assignee: Arcadia Biosciences Inc., Seattle, WA (US)

( * ) Notice: Subject to any disclaimer, the term of this patent is extended or adjusted under 35 U.S.C. 154(b) by 0 days.

(21) Appl. No.: 15/740,876

(22) PCT Filed: Jul. 1, 2016

(86) PCT No.: PCT/US2016/040760
§ 371 (c)(1),
(2) Date: Dec. 29, 2017

(87) PCT Pub. No.: WO2017/004558
PCT Pub. Date: Jan. 5, 2017

(65) Prior Publication Data
US 2020/0017873 A1 Jan. 16, 2020

Related U.S. Application Data

(60) Provisional application No. 62/188,360, filed on Jul. 2, 2015.

(51) Int. Cl.
C12N 15/82 (2006.01)
A01H 5/10 (2018.01)
A23L 7/10 (2016.01)

(52) U.S. Cl.
CPC .......... C12N 15/8274 (2013.01); A23L 7/10 (2016.08); C12N 15/8275 (2013.01)

(58) Field of Classification Search
CPC .. C12N 15/8274; C12N 15/8275; A01H 5/10; A01H 6/4678
See application file for complete search history.

(56) References Cited

U.S. PATENT DOCUMENTS

| | | | |
|---|---|---|---|
| 6,870,075 B1 * | 3/2005 | Beetham | A01H 1/06 800/278 |
| 7,723,575 B2 | 5/2010 | Alibhai et al. | |
| 8,872,007 B2 * | 10/2014 | Shantz | C12N 15/8289 426/549 |
| 2003/0084473 A1 | 5/2003 | Gocal et al. | |
| 2009/0307802 A1 * | 12/2009 | Gocal | C12N 9/1092 800/292 |
| 2011/0119783 A1 | 5/2011 | Kidwell et al. | |

OTHER PUBLICATIONS

International Wheat Genome Sequencing Consortium. "A chromosome-based draft sequence of the hexaploid bread wheat (*Triticum aestivum*) genome." Science 345.6194 (2014): 1251788. (Year: 2014).*
NCBI, GenBank accession No. ACH72672.1 (Sep. 7, 2008) (Year: 2008).*
International Search Report and Written Opinion for International Application No. PCT/US2016/040760 dated Jan. 17, 2017, 14 pages.
Dong et al., "Oligonucleotide-directed gene repair in wheat using a transient plasmid gene repair assay system", Genetic Transformation and Hybridization, Plant Cell Rep (2006) 25: 457-465.
Dong et al., "Oligonucleotide-Directed Gene Repair: Promises and Limitations for Plant Gene Modification", Transgenic Plant Journal 1(1), 2007 Global Science Books, 10-16.
Sauer et al., "Oligonucleotide-directed mutagenesis for precision gene editing", Plant Biotechnology Journal, doi: 10.1111/pbi.12496, 2015, 1-7.
Yu et al., "Evolution of a Double Amino Acid Substitution in the 5-Enolpyruvylshikimate-3-Phosphate Synthase in Eleusine indica Conferring High-Level Glyphosate Resistance", Plant Physiology, Apr. 2015, vol. 167, 144-1447.
Sammons et al., "Glyphosate resistance: state of knowledge", Pest Management Science, Epub. Mar. 12, 2014, vol. 70, No. 9, 1367-1377.
Li et al., "Gene replacements and insertions in rice by intron targeting using CRISPR-Cas9", Nature Plants, vol. 2, Sep. 12, 2016, doi: 10.1038/NPLANTS.2016.139, 1-6.

* cited by examiner

*Primary Examiner* — Weihua Fan
(74) *Attorney, Agent, or Firm* — Husch Blackwell LLP

(57) ABSTRACT

Plants with resistance to glyphosate are disclosed herein. In one embodiment, the disclosure relate to human induced non-transgenic mutations in the EPSPS gene in plants.

10 Claims, 1 Drawing Sheet
Specification includes a Sequence Listing.

```
      wheat   ..MAMAAAAT VAASASSSAV SLDRAAPAHP RRLRMPAA.R AAHRGAVRLW
       rice   MAATMASNAA AAAAVSLDQA VAASAAFSSR KQLRLPAAAR GGMRVRVRAR
  Consensus   ..aaMAaaAa aAAaaSldaa saarAAfahr rrLR$PAA.R aahRgaVRar 51                                                 100
      wheat   GPRGAA..AR ATSVAAPAAP AGAEEVVLQP IREISGAVQL PGSKSLSNRI
       rice   GRREAVVVAS ASSSSVAAPA AKAEEIVLQP IREISGAVQL PGSKSLSNRI
  Consensus   GrReAa..Ar AsSsaaaAaa AgAEE!VLQP IREISGAVQL PGSKSLSNRI 101                                                150
      wheat   LLLSALSEGT TVVDNLLNSE DVHYMLEALE ALGLSVEADK VAKRAVVVGC
       rice   LLLSALSEGT TVVDNLLNSE DVHYMLEALK ALGLSVEADK VAKRAVVVGC
  Consensus   LLLSALSEGT TVVDNLLNSE DVHYMLEALe ALGLSVEADK VAKRAVVVGC 151                                                200
      wheat   GGRFPVEKDA KEEVKLFLGN AGTAMRPLTA AVVAAGGNAT YVLDGVPRMR
       rice   GGKFPVEKDA KEEVQLFLGN AGTAMRPLTA AVTAAGGNAT YVLDGVPRMR
  Consensus   GGrFPVEKDA KEEVqLFLGN AGTAMRPLTA AVtAAGGNAT YVLDGVPRMR 201                                                250
      wheat   ERPIGDLVVG LQQLGADVDC FLGTNCPPVR INGKGGLPGG KVKLSGSISS
       rice   ERPIGDLVVG LKQLGADVDC FLGTECPPVR VKGIGGLPGG KVKLSGSISS
  Consensus   ERPIGDLVVG LqQLGADVDC FLGT#CPPVR !nGiGGLPGG KVKLSGSISS 251                                                300
      wheat   QYLSSLLMAA PLALEDVEIE IIDKLISVPY VEMTLKLMER FGVTAEHSDS
       rice   QYLSALLMAA PLALGDVEIE IIDKLISIPY VEMTLRLMER FGVKAEHSDS
  Consensus   QYLSaLLMAA PLALeDVEIE IIDKLIS!PY VEMTLrLMER FGVkAEHSDS 301                                                350
      wheat   WDRFYIKGGQ KYKSPGNAYV EGDASSASYF LAGAAITGGT VTVEGCGTTS
       rice   WDRFYIKGGQ KYKSPGNAYV EGDASSASYF LAGAAITGGT VTVQGCGTTS
  Consensus   WDRFYIKGGQ KYKSPGNAYV EGDASSASYF LAGAAITGGT VTV#GCGTTS 351                                                400
      wheat   LQGDVKFAEV LEMMGAKVTW TDTSVTVTGP PRQPFGRKHL KAVDVNMNKM
       rice   LQGDVKFAEV LEMMGAKVTW TDTSVTVTGP PREPYGKKHL KAVDVNMNKM
  Consensus   LQGDVKFAEV LEMMGAKVTW TDTSVTVTGP PR#P%GrKHL KAVDVNMNKM 401                                                450
      wheat   PDVAMTLAVV ALFADGPTAI RDVASWRVKE TERMVAIRTE LTKLGATVEE
       rice   PDVAMTLAVV ALFADGPTAI RDVASWRVKE TERMVAIRTE LTKLGASVEE
  Consensus   PDVAMTLAVV ALFADGPTAI RDVASWRVKE TERMVAIRTE LTKLGAsVEE 451                                                500
      wheat   GPDYCIITPP EKLNITAIDT YDDHRMAMAF SLAACAEVPV TIRDPGCTRK
       rice   GPDYCIITPP EKLNITAIDT YDDHRMAMAF SLAACADVPV TIRDPGCTRK
  Consensus   GPDYCIITPP EKLNITAIDT YDDHRMAMAF SLAACA#VPV TIRDPGCTRK 501        515
      wheat   TFPNYFDVLS TFVKN
       rice   TFPNYFDVLS TFVRN
  Consensus   TFPNYFDVLS TFVrN
```

WHEAT HAVING RESISTANCE TO GLYPHOSATE DUE TO ALTERATIONS IN 5-ENOL-PYRUVYLSHIKIMATE-3 PHOSPHATE SYNTHASE

CROSS-REFERENCE TO RELATED APPLICATIONS

This application claims priority to U.S. Provisional Patent Application No. 62/188,360 filed Jul. 2, 2015, which is incorporated herein by reference in its entirety.

FIELD

This disclosure relates to mutations in one or more 5-enol-pyruvylshikimate-3-phosphate synthase (EPSPS) homoeologous genes of wheat and wheat plants and plant parts having said mutations in at least one of their EPSPS homoeologous gene sequences. In one embodiment, the mutation is a human induced non-transgenic mutation. In another embodiment, the disclosure relates to wheat having resistance to the herbicide glyphosate as a result of mutations in at least one of their EPSPS homoeologous genes.

BACKGROUND

The control of weeds in wheat cultivation would be considerably improved if the wheat could be made resistant to the lethal effects of the herbicide used by commercial growers to control the weeds. One such herbicide is glyphosate, which inhibits the enzyme 5-enolpyruvylshikimate-3-phosphate synthase (EPSPS). Because EPSPS activity is required for the biosynthesis of a number of essential compounds including amino acids and lignin, its inhibition is lethal to plants. Glyphosate is a very effective herbicide and is widely used in commercial agriculture.

A number of crop plants, including canola, corn, soybeans and cotton, have been transgenically engineered to over-express an altered bacterial EPSPS. The altered bacterial EPSPS does not bind glyphosate but still retains high affinity for the plants' endogenous substrates, including phosphoenolpyruvic acid (PEP) and 3-phophoshikimic acid. Fields planted with these genetically engineered crops can be sprayed with glyphosate during the growing season to control weeds since the crops expressing the altered bacterial EPSPS survive.

Because of its tremendous commercial value, transgenic glyphosate resistant wheat has been developed (U.S. Pat. No. 7,071,325) but it has not been released commercially due largely to the lack of acceptance by consumers of genetically modified (GM) foods (Stokstad, Science 304: 1088-1089, 2004). Because many consumers have preferences against GM crops, particularly GM food crops, attempts have been made to develop glyphosate resistant wheat through non-transgenic means. For example, the use of recombinogenic oligonucleotides to mutate endogenous EPSPS genes has been proposed (US Patent Application 2008/0256668) but it was not demonstrated that glyphosate resistant *Arabidopsis* plants could in fact be regenerated using this methodology and it was not shown that this methodology would work in wheat.

Despite previous investigations into the properties of EPSPS and the conserved nature of the glyphosate binding pocket, there is variation among species in the particular amino acid changes in the EPSPS enzyme that lead to resistance. For example, an alteration of a threonine to isoleucine at position 97 in the *E. coli* EPSPS leads to sensitivity to glyphosate and decreased affinity of the enzyme for its natural substrate phosphoenolpyruvate (PEP) (Funke et al., *Journal of Biological Chemistry* 284: 9854-9860, 2009), while, by contrast, alteration of the equivalent threonine to isoleucine in the maize EPSPS leads to reduced inhibition by glyphosate (U.S. Pat. No. 6,566,587).

In conclusion, there is a continuing commercial interest in the development of glyphosate resistant wheat that is not the product of genetic engineering and would therefore be acceptable to all consumers. Previous work has demonstrated that the transgenic over-expression of a mutated bacterial EPSPS results in glyphosate resistance in a number of crops including wheat. However, to date, there is no evidence that mutations of one or more endogenous EPSPS genes will lead to resistance in any crop plant, particularly in a hexaploid plant such as wheat. Further, the nature of the mutations that could result in glyphosate resistance is not known since species specific differences have been noted despite the fact that glyphosate binding domain is highly conserved across EPSPSs.

To meet the need for non-transgenic glyphosate resistant wheat, we have used a target-selected mutagenesis screening method to create and identify specific alterations in each of the three homoeologous copies of hexaploid wheat EPSPS. Novel partial genomic DNA sequences for the three wheat EPSPS homoeologous genes were determined and then used to identify individual wheat plants that contained specific alterations in the active site region of each EPSPS homoeologue. Using the mutations as selective markers, crosses were made to generate plants that were homozygous for preferred alterations in all of the homoeologous copies of EPSPS. Because these wheat plants are resistant to glyphosate without the inclusion of foreign DNA in their genomes, they will be acceptable to consumers and wheat breeders alike. Such a non-transgenic wheat cultivar with resistance to glyphosate as a result of human-induced non-transgenic mutations in one or more EPSPS homoeologous genes would have tremendous value for wheat based food products such as breads, cakes, cookies, tortillas and crackers.

SUMMARY

In one embodiment, the disclosure relates to plants and plant parts with one or mutations in an EPSPS gene that result in glyphosate resistant plants, including but not limited to barley, wheat and rye plants. In one embodiment, the disclosure relates to plants and plant parts with one or mutations in an EPSPS gene that result in glyphosate tolerant plants, including but not limited to barley, wheat and rye plants.

In one embodiment, the mutations are human-induced non-transgenic mutations. In yet another embodiment, the disclosure relates to plants with modified genes, wherein the genes were modified by genomic editing and contribute to plants with resistance to glyphosate.

In one embodiment, the plants discussed herein include wheat, barley and rye. In one embodiment, the disclosure relates to grains from plants and plant parts with one or mutations in an EPSPS gene.

In one embodiment, the disclosure relates to plants with non-transgenic mutations in one or more EPSPS genes, or homologous genes, which result in plants with resistance to glyphosate. In one embodiment, the disclosure relates to non-transgenic mutations in the EPSPS gene, wherein said mutations result in plants with resistance to glyphosate.

In one embodiment, one or more mutations are in the EPSPS gene of the wheat A genome. In another embodiment, one or more mutations are in the EPSPS gene of the wheat B genome. In another embodiment, one or more mutations are in the EPSPS gene of the D genome.

In one embodiment, the disclosure relates to multiple non-transgenic mutations in the EPSPS gene including but not limited to 1, 2, 3, 4, 5, 6, 7, 8, 9, 10, and greater than 10 mutations.

In another embodiment, the disclosure relates to multiple non-transgenic mutations in the EPSPS gene of the A genome including but not limited to 1, 2, 3, 4, 5, 6, 7, 8, 9, 10, and greater than 10 mutations and multiple mutations in the EPSPS gene of the B genome including but not limited to 1, 2, 3, 4, 5, 6, 7, 8, 9, 10, and greater than 10 mutations.

In another embodiment, the disclosure relates to multiple non-transgenic mutations in the EPSPS gene of the A genome including but not limited to 1, 2, 3, 4, 5, 6, 7, 8, 9, 10, and greater than 10 mutations and multiple mutations in the EPSPS gene of the D genome including but not limited to 1, 2, 3, 4, 5, 6, 7, 8, 9, 10, and greater than 10 mutations.

In another embodiment, the disclosure relates to multiple non-transgenic mutations in the EPSPS gene of the B genome including but not limited to 1, 2, 3, 4, 5, 6, 7, 8, 9, 10, and greater than 10 mutations and multiple mutations in the EPSPS gene of the D genome including but not limited to 1, 2, 3, 4, 5, 6, 7, 8, 9, 10, and greater than 10 mutations.

In another embodiment, the disclosure relates to multiple non-transgenic mutations in the EPSPS gene of the A genome including but not limited to 1, 2, 3, 4, 5, 6, 7, 8, 9, 10, and greater than 10 mutations and multiple mutations in the EPSPS gene of the B genome including but not limited to 1, 2, 3, 4, 5, 6, 7, 8, 9, 10, and greater than 10 mutations and multiple mutations in the EPSPS gene of the D genome including but not limited to 1, 2, 3, 4, 5, 6, 7, 8, 9, 10, and greater than 10 mutations.

In one embodiment, the disclosure relates to a wheat plant comprising at least two mutations in an EPSPS gene of the A genome, wherein the mutated EPSPS gene of the A genome encodes an EPSPS polypeptide comprising a threonine to isoleucine change at amino acid position 168 (T168I) and a proline to serine change at amino acid position 172 (P172S) of SEQ ID NO. 9.

In yet another embodiment, the disclosure relates to a wheat plant comprising two mutations in an EPSPS gene of the D genome, wherein the mutated EPSPS gene of the D genome encodes an EPSPS polypeptide comprising a threonine to isoleucine change at amino acid position 168 (T168I) and a proline to serine change at amino acid position 172 (P172S) of SEQ ID NO. 9.

In another embodiment, the disclosure relates to a wheat plant, wheat seeds, wheat plant parts, and progeny thereof with resistance to glyphosate as compared to wild type wheat plant, wheat seeds, wheat plant parts, and progeny thereof.

In another embodiment, the disclosure relates to a wheat plant, wheat seeds, wheat plant parts, and progeny thereof having resistance to glyphosate as compared to the wild type wheat plant, wherein the resistance to glyphosate is caused by a human-induced non-transgenic mutation in one or more of the wheat plant's EPSPS genes. In another embodiment, the disclosure relates to wheat plants with resistance to glyphosate as compared to the wild type wheat plant and normal germination and viability rates.

In another embodiment, the altered EPSPS protein, which is coded for by the EPSPS gene having a mutation, has altered affinity for glyphosate. In yet another embodiment, the altered EPSPS protein retains substantial affinity for the enzyme's endogenous substrates.

In another embodiment, the disclosure relates to a wheat plant containing one or more mutated EPSPS genes, as well as seeds, pollen, plant parts and progeny of that plant.

In another embodiment, the disclosure relates to food and food products incorporating wheat seeds and wheat flour with an altered EPSPS protein, which has reduced affinity for glyphosate caused by a human-induced non-transgenic mutation in one or more EPSPS genes.

In another embodiment, this disclosure relates to a wheat plant having one or more EPSPS proteins with reduced affinity for glyphosate compared to the wild type wheat plants, created by the steps of obtaining plant material from a parent wheat plant, inducing at least one mutation in at least one copy of a EPSPS gene of the plant material by treating the plant material with a mutagen to create mutagenized plant material (e.g., seeds or pollen), analyzing progeny wheat plants to detect at least one mutation in at least one copy of an EPSPS gene, selecting progeny wheat plants that have at least one mutation in at least one copy of an EPSPS gene, crossing progeny wheat plants that have at least one mutation in at least one copy of an EPSPS gene with other progeny wheat plants that have at least one mutation in a different copy of a EPSPS gene, and repeating the cycle of identifying progeny wheat plants having mutations and crossing the progeny wheat plants having mutations with other progeny wheat plants having mutations to produce progeny wheat plants with an EPSPS protein with reduced affinity for glyphosate. In another embodiment, the method comprises growing or using the mutagenized plant material to produce progeny wheat plants.

BRIEF DESCRIPTION OF THE SEQUENCE LISTING

SEQ ID NO:1 shows the Oryza sativa EPSPS mRNA (NCBI Reference Sequence NM_001063247).

SEQ ID NO:2 shows the Oryza sativa EPSPS genomic DNA (NCBI Reference Sequence NC_008399).

SEQ ID NO: 3 shows the EPSPS protein encoded by SEQ ID NO: 2 (NCBI Reference Sequence NP_001056712).

SEQ ID NOs: 4-5 show the DNA sequences for *Triticum aestivum* EPSPS-specific primers used for genomic sequencing.

SEQ ID NO: 6 shows the DNA sequence of a PCR product that comprises a partial genomic DNA sequence for EPSPS for the A genome of wheat.

SEQ ID NO: 7 shows the DNA sequence of a PCR product that comprises a partial genomic DNA sequence for EPSPS for the B genome of wheat.

SEQ ID NO: 8 shows the DNA sequence of a PCR product that comprises a partial genomic DNA sequence for EPSPS for the D genome of wheat.

SEQ ID NO: 9 shows the amino acid sequence for the wheat EPSPS protein.

SEQ ID NOs: 10-13 show the DNA sequences for wheat EPSPS-specific primers used for mutation detection.

SEQ ID NOs: 14-17 show primers useful for mutation detection.

SEQ ID NO. 18 shows the amino acid sequence of the active region of the wheat EPSPS protein.

BRIEF DESCRIPTION OF THE FIGURES

FIG. 1 is a sequence alignment of the rice EPSPS protein (SEQ ID NO. 20) and the wheat EPSPS protein (SEQ ID NO. 19). There is substantial similarity between the rice and wheat EPSPS proteins (consensus shown as SEQ ID NO. 21).

DETAILED DESCRIPTION

Definitions

The numerical ranges in this disclosure are approximate, and thus may include values outside of the range unless otherwise indicated. Numerical ranges include all values from and including the lower and the upper values, in increments of one unit, provided that there is a separation of at least two units between any lower value and any higher value. As an example, if a compositional, physical or other property, such as, for example, molecular weight, viscosity, etc., is from 100 to 1,000, it is intended that all individual values, such as 100, 101, 102, etc., and sub ranges, such as 100 to 144, 155 to 170, 197 to 200, etc., are expressly enumerated. For ranges containing values which are less than one or containing fractional numbers greater than one (e.g., 1.1, 1.5, etc.), one unit is considered to be 0.0001, 0.001, 0.01 or 0.1, as appropriate. For ranges containing single digit numbers less than ten (e.g., 1 to 5), one unit is typically considered to be 0.1. These are only examples of what is specifically intended, and all possible combinations of numerical values between the lowest value and the highest value enumerated, are to be considered to be expressly stated in this disclosure. Numerical ranges are provided within this disclosure for, among other things, relative amounts of components in a mixture, and various temperature and other parameter ranges recited in the methods.

As used herein, the term "allele" is any of one or more alternative forms of a gene, all of which relate to one trait or characteristic. In a diploid cell or organism, the two alleles of a given gene occupy corresponding loci on a pair of homologous chromosomes. In a tetraploid or hexaploid cell or organism, such as wheat, the two alleles of a given gene on one of the genomes occupy corresponding loci on a pair of homologous chromosomes and the two alleles of the same gene occupying the same loci on another of the genomes such as the A or B genomes of tetraploid, or the A, B or D genomes of hexaploid wheat are said to be homoeologous to the gene of the first genome and to be present on homoeologous chromosomes.

As used herein, the terms "altering," "increasing," "increased," "reducing," "reduced," "inhibited" or the like are considered relative terms, i.e. in comparison with the wild-type or unaltered state. The "level of a protein" refers to the amount of a particular protein, for example EPSPS, which may be measured by any means known in the art such as, for example, Western blot analysis or other immunological means.

As used herein, "altered EPSPS protein activity" refers to an EPSPS protein with reduced affinity for glyphosate. In one embodiment, the EPSPS protein may have altered affinity for glyphosate but retain substantial affinity for plant or endogenous substrates. It would be appreciated that the level of EPSPS activity might be altered in a mutant but not the expression level (amount) of the protein itself. Conversely, the amount of protein might be altered but the activity remain the same if a more or less active protein is produced. Reductions in both amount and activity are also possible such as, for example, when a gene encoding the protein is inactivated. In certain embodiments, the reduction in the level of protein or reduced affinity for glyphosate is by at least 10% or by at least 20% or by at least 30% or by at least 40% or by at least 50% or by at least 60%, or by at least 70%, or by at least 80% or by at least 85% or by at least 90% or at least 95% as compared to the level of protein or affinity for glyphosphgate in the endosperm of unmodified wheat. The reduction in the level of the protein or gene expression or EPSPS protein affinity for glyphosate may occur at any stage in the development of the plant and grain, particularly in the meristem of the plant during vegetative growth and during the grain filling stage, or at all stages of the plant and grain development through to maturity.

As used herein, amino acid or nucleotide sequence "identity" and "similarity" are determined from an optimal global alignment between the two sequences being compared. An optimal global alignment is achieved using, for example, the Needleman-Wunsch algorithm (Needleman and Wunsch, 1970, J. Mol. Biol. 48:443-453). Sequences may also be aligned using algorithms known in the art including but not limited to CLUSTAL V algorithm or the Blastn or BLAST 2 sequence programs.

"Identity" means that an amino acid or nucleotide at a particular position in a first polypeptide or polynucleotide is identical to a corresponding amino acid or nucleotide in a second polypeptide or polynucleotide that is in an optimal global alignment with the first polypeptide or polynucleotide. In contrast to identity, "similarity" encompasses amino acids that are conservative substitutions. A "conservative" substitution is any substitution that has a positive score in the Blosum62 substitution matrix (Hentikoff and Hentikoff, 1992, Proc. Natl. Acad. Sci. USA 89: 10915-10919).

By the statement "sequence A is n % similar to sequence B," it is meant that n % of the positions of an optimal global alignment between sequences A and B consists of identical residues or nucleotides and conservative substitutions. By the statement "sequence A is n % identical to sequence B," it is meant that n % of the positions of an optimal global alignment between sequences A and B consists of identical residues or nucleotides.

As used herein, the term "gene" or "gene sequence" refers to the partial or complete coding sequence of a gene, its complement, and its 5' or 3' un-translated regions. A gene is also a functional unit of inheritance, and in physical terms is a particular segment or sequence of nucleotides along a molecule of DNA (or RNA, in the case of RNA viruses) involved in producing a polypeptide chain. The latter may be subjected to subsequent processing such as chemical modification or folding to obtain a functional protein or polypeptide. A gene may be isolated, partially isolated, or found within an organism's genome. By way of example, a transcription factor gene encodes a transcription factor polypeptide, which may be functional or require processing to function as an initiator of transcription.

Operationally, genes may be defined by the cis-trans test, a genetic test that determines whether two mutations occur in the same gene and that may be used to determine the limits of the genetically active unit. A gene generally includes regions preceding ("leaders"; upstream) and following ("trailers"; downstream) the coding region. A gene may also include intervening, non-coding sequences, referred to as "introns", located between individual coding segments, referred to as "exons." Most genes have an associated promoter region, a regulatory sequence 5' of the transcription initiation codon (there are some genes that do not have an identifiable promoter). The function of a gene may also be regulated by enhancers, operators, and other regulatory elements.

As used herein, the term "modified plant" includes a plant that has a non-transgenic mutation, or a plant containing a transgene, or a plant that has undergone genomic editing or combinations thereof.

As used herein, the term "plant" includes reference to an immature or mature whole plant, including a plant from which seed or grain or anthers have been removed. A seed or embryo that will produce the plant is also considered to be the plant.

As used herein, the term "plant parts" includes plant protoplasts, plant cell tissue cultures from which wheat plants can be regenerated, plant calli, plant clumps, and plant cells that are intact in plants or parts of plants, such as embryos, pollen, ovules, pericarp, seed, flowers, florets, heads, spikes, leaves, roots, root tips, anthers, and the like.

As used herein, the term "polypeptide(s)" refers to any peptide or protein comprising two or more amino acids joined to each other by peptide bonds or modified peptide bonds. "Polypeptide(s)" refers to both short chains, commonly referred to as peptides, oligopeptides and oligomers, and to longer chains generally referred to as proteins. Polypeptides may contain amino acids other than the 20 gene-encoded amino acids. "Polypeptide(s)" include those modified either by natural processes, such as processing and other post-translational modifications, but also by chemical modification techniques. Such modifications are well described in basic texts and in more detailed monographs, as well as in a voluminous research literature and they are well known to those of skill in the art. It will be appreciated that the same type of modification may be present in the same or varying degree at several sites in a given polypeptide.

As used herein, the term "polynucleotide(s)" generally refers to any polyribonucleotide or poly-deoxyribonucleotide, which may be unmodified RNA or DNA or modified RNA or DNA.

This definition includes, without limitation, single- and double-stranded DNA, DNA that is a mixture of single- and double-stranded regions or single-, double- and triple-stranded regions, cDNA, single- and double-stranded RNA, and RNA that is a mixture of single- and double-stranded regions, hybrid molecules comprising DNA and RNA that may be single-stranded or, more typically, double-stranded, or triple-stranded regions, or a mixture of single- and double-stranded regions. The term "polynucleotide(s)" also embraces short nucleotides or fragments, often referred to as "oligonucleotides," that due to mutagenesis are not 100% identical but nevertheless code for the same amino acid sequence.

As used herein, the phrase "reduced affinity for glyphosate" refers to binding and/or interacting with glyphosate at a lower rate than normally measured. In one embodiment, a reduced affinity for glyphosate refers to a protein that shows no binding of glyphosate. In another embodiment, a reduced affinity for glyphosate refers to an EPSPS protein with one or more mutations that binds glyphosate at a slower rate than wild type EPSPS. In one embodiment, a reduced affinity for glyphosate refers to an EPSPS protein with one or more mutations that binds glyphosate at a rate of about 10% or 20% or 30% or 40% or 50% or 60% or 70% or 80% or 85% or 90% or 95% of the wild type EPSPS binding rate for glyphosate. In one embodiment, a reduced affinity for glyphosate refers to an EPSPS protein with one or more mutations that binds glyphosate at a rate of less than 70%, or less than 60%, or less than 50%, or less than 40%, or less than 30%, or less than 20%, or less than 10%, or less than 5% of the wild type EPSPS binding rate for glyphosate.

As used herein, the term "resistance to glyphosate" is used interchangeably with the term "tolerance to glyphosate." Both terms encompass a plants ability to grow under an application rate of glyphosate that would normally causes harm and/or growth inhibition in a wild type plant. The term "resistance to glyphosate" encompasses a plants ability to grow and/or produce at an application rate of glyphosphate that would be detrimental or lethal to a wild type plant.

In one embodiment, resistance/tolerance to glyphosphate encompasses a plant's ability to grow, produce, or live in a higher percentage or amount of glyphosphate including but not limited to 1-5%, 5-10%, 10-15%, 15-20%, 20-25%, 25-30%, 30-35%, 35-40%, 40-45%, 45-50%, 50-55%, 55-60%, 60-65%, 65-70%, 70-75%, 75-80%, 80-85%, 85-90%, 90-95%, 95-100% and greater than 100% as compared to a wild type plant.

In one embodiment, resistance/tolerance to glyphosphate encompasses a plant's ability to grow, produce, or live with an increased number of applications of glyphosphate as compared to a wild type plant including but not limited to 1, 2, 3, 4, 5, 6, 7, 8, 9, 10, and greater than 10 applications of glyphosphate.

A "reduced or non-functional fragment," as is used herein, refers to a nucleic acid sequence that encodes a EPSPS protein that has reduced affinity for glyphosate as compared to the protein coding sequence of the whole nucleic acid sequence. In other words, it refers to a nucleic acid or fragment(s) thereof that substantially retains the capacity of encoding a EPSPS polypeptide, but the encoded EPSPS polypeptide has reduced affinity for glyphosate.

The term "fragment," as used herein, refers to a polynucleotide sequence, (e.g, a PCR fragment) which is an isolated portion of the subject nucleic acid constructed artificially (e.g., by chemical synthesis) or by cleaving a natural product into multiple pieces, using restriction endonucleases or mechanical shearing, or a portion of a nucleic acid synthesized by PCR, DNA polymerase or any other polymerizing technique well known in the art, or expressed in a host cell by recombinant nucleic acid technology well known to one of skill in the art.

With reference to polynucleotides of the disclosure, the term "isolated polynucleotide" is sometimes used. This term, when applied to DNA, refers to a DNA molecule that is separated from sequences with which it is immediately contiguous (in the 5' and 3'directions) in the naturally occurring genome of the organism from which it was derived. For example, the "isolated polynucleotide" may comprise a PCR fragment. In another embodiment, the "isolated polynucleotide" may comprise a DNA molecule inserted into a vector, such as a plasmid or virus vector, or integrated into the genomic DNA of a prokaryote or eukaryote. An "isolated polynucleotide molecule" may also comprise a cDNA molecule.

As used herein, a single nucleotide polymorphism (SNP) is a single nucleotide base difference between two DNA according to nucleotide substitutions either as transitions (C/T or G/A) or transversions (C/G, A/T, C/A or T/G). Single base variants are considered to be SNPs as are single base insertions and deletions (in/dels) in the genome.

As used herein, a "transgenic plant" refers to a plant that contains a gene construct ("transgene") not found in a wild-type plant of the same species, variety or cultivar. A "transgene" as referred to herein has the normal meaning in the art of biotechnology and includes a genetic sequence that has been produced or altered by recombinant DNA or RNA technology and which has been introduced into the plant cell. The transgene may include genetic sequences derived from a plant cell. Typically, the transgene has been introduced into the plant by human manipulation such as, for example, by transformation but any method can be used as one of skill in the art recognizes.

As used herein, a "modified EPSPS gene" includes modification of the EPSPS gene through non-transgenic mutations or transgenes or genomic editing or combinations thereof.

As used herein, a "EPSPS derivative" refers to a EPSPS protein/peptide/polypeptide sequence that possesses reduced affinity for glyphosate as compared to the whole EPSPS protein/peptide/polypeptide sequence. The term "EPSPS derivative" encompasses the "fragments" or "chemical derivatives" of a modified EPSPS protein/peptide.

A wheat plant is defined herein as any plant of a species of the genus *Triticum*, which species is commercially cultivated, including, for example, *Triticum aestivum* L. ssp. *aestivum* (common or bread wheat), other subspecies of *Triticum aestivum*, *Triticum turgidum* L. ssp. *durum* (durum wheat, also known as macaroni or pasta wheat), *Triticum monococcum* L. ssp. *monococcum* (cultivated einkorn or small spelt), *Triticum timopheevi* ssp. *timopheevi*, *Triticum turgidum* L. ssp. *dicoccon* (cultivated emmer), and other subspecies of *Triticum turgidum* (Feldman). The wheat may be hexaploid wheat having an AABBDD type genome, or tetraploid wheat having an AABB type genome. Since genetic variation in wheat transferred to certain related species, including rye and barley by hybridization, the disclosure also includes the hybrid species thus formed, including triticale that is a hybrid between bread wheat and rye. In one embodiment, the wheat plant is of the species Triticum aestivum, and preferably of the subspecies aestivum. Alternatively, since mutations or transgenes can be readily transferred from Triticum aestivum to durum wheat, the wheat is preferably *Triticum turgidum* L. ssp. *durum*.

In another embodiment, the disclosure describes wheat plants exhibiting resistance to glyphosate as compared to wild type wheat plants without the inclusion of foreign nucleic acids in the wheat plant genome. In one embodiment, the disclosure relates to non-transgenic mutations in one or more EPSPS genes.

In still another embodiment, the disclosure relates to a series of independent human-induced non-transgenic mutations in one or more EPSPS genes; wheat plants having one or more of these mutations in at least one EPSPS gene thereof; and a method of creating and identifying similar and/or additional mutations in at least one EPSPS gene of wheat.

In yet another embodiment, the disclosure relates to a transgenic wheat plant with a transgene that reduces expression of the EPSPS gene and/or reduces affinity of the EPSPS protein for glyphosate as compared to a wild type plant.

In still another embodiment, the disclosure relates to wheat plant having a modified EPSPS gene, wherein the EPSPS gene is modified by genomic editing, and further wherein said modification contributes to plants with resistance to glyphosate as compared to a wild type plant.

I. 5-enolpyruvylshikimate-3-phosphate Synthase (EPSPS)

In one embodiment, the disclosure relates to reducing expression of the EPSPS gene. In another embodiment, the disclosure relates to reducing affinity of the EPSPS protein for glyphosate. In one embodiment, the disclosure relates to wheat plants with an EPSPS protein with reduced affinity for glyphosate. In one embodiment, reducing expression of the EPSPS gene or reducing affinity of the EPSPS protein for glyphosate can be accomplished by non-transgenic mutations, transgenes, or genomic editing.

In one embodiment, the disclosure relates to modifying the EPSPS gene through non-transgenic mutations, or transgenes or genomic editing.

In one embodiment, the disclosure relates to modifying the EPSPS gene through non-transgenic mutations, or transgenes or genomic editing resulting in an altered EPSPS protein with reduced affinity for glyphosate but substantial affinity for plant substrates as compared to an unaltered or wild type EPSPS protein. In one embodiment, substantial affinity for plant substrates refers to an altered EPSPS protein that has at least 70%, or at least 75%, or at least 80% or at least 85% or at least 90% or at least 95% of the affinity of wild type EPSPS for plant substrates.

FIG. 1 provides an alignment of the protein sequence of rice EPSPS and the wheat EPSPS protein. As can be observed, substantial identity exists between the rice EPSPS and wheat EPSPS proteins. Minor differences can be found between the rice and wheat EPSPS protein in the N-terminal region.

The active region of the EPSPS protein is highly conserved between the rice and wheat EPSPS proteins. The active region is typically encompassed by the following amino acid sequence: FLGNAGTAMRPLTAAVVAAGGN (SEQ ID NO. 18).

II. Mutations of the EPSPS Gene

In one embodiment, wheat seeds can be mutagenized with ethyl methanesulfonate (EMS) and then grown into M1 plants. The M1 plants were then allowed to self-pollinate and seeds from the M1 plant were grown into M2 plants, which were then screened for mutations in their EPSPS loci. M1 plants can be screened for mutations but an advantage of screening the M2 plants is that all somatic mutations correspond to germline mutations. One of skill in the art would understand that a variety of wheat plant materials, including but not limited to, seeds, pollen, plant tissue or plant cells, may be mutagenized in order to create the EPSPS-mutated wheat plants of the disclosure. However, the type of plant material mutagenized may affect when the plant DNA is screened for mutations. For example, when pollen is subjected to mutagenesis prior to pollination of a non-mutagenized plant, the seeds resulting from that pollination are grown into M1 plants. Every cell of the M1 plants will contain mutations created in the pollen, thus these M1 plants may then be screened for EPSPS mutations instead of waiting until the M2 generation.

Mutagens that create primarily point mutations and short deletions, insertions, transversions, and or transitions (about 1 to about 5 nucleotides), such as chemical mutagens or radiation, may be used to create the mutations. Mutagens conforming with the method disclosed herein include, but are not limited to, ethyl methanesulfonate (EMS), methylmethane sulfonate (MMS), N-ethyl-N-nitrosurea (ENU), triethylmelamine (TEM), N-methyl-N-nitrosourea (MNU), procarbazine, chlorambucil, cyclophosphamide, diethyl sulfate, acrylamide monomer, melphalan, nitrogen mustard, vincristine, dimethylnitrosamine, N-methyl-N'-nitro-Nitrosoguanidine (MNNG), nitrosoguanidine, 2-aminopurine, 7, 12 dimethyl-benz(a)anthracene (DMBA), ethylene oxide, hexamethylphosphoramide, bisulfan, diepoxyalkanes (diepoxyoctane (DEO), diepoxybutane (BEB), and the like), 2-methoxy-6-chloro-9[3-(ethyl-2-chloro-ethyl)aminopropylamino] acridine dihydrochloride (ICR-170), and formaldehyde.

Any suitable method of plant DNA preparation now known or hereafter devised may be used to prepare the wheat plant DNA for EPSPS mutation screening. For example, see Chen & Ronald, *Plant Molecular Biology Reporter* 17:53-57, 1999; Stewart and Via, *Bio Techniques* 14:748-749, 1993. Additionally, several commercial kits are available, including kits from Qiagen (Valencia, Calif.) and Qbiogene (Carlsbad, Calif.).

In one embodiment, prepared DNA from individual wheat plants was then pooled in order to expedite screening for mutations in the EPSPS genes of the entire population of plants originating from the mutagenized plant tissue. The size of the pooled group may be dependent upon the sensitivity of the screening method used and the ploidy of the plants being screened. Preferably, groups of two or more individual wheat plants are pooled.

In another embodiment, after the DNA samples are pooled, the pools are subjected to EPSPS sequence-specific amplification techniques, such as Polymerase Chain Reaction (PCR). For a general overview of PCR, see *PCR Protocols: A Guide to Methods and Applications* (Innis, Gelfand, Sninsky, and White, eds.), Academic Press, San Diego, 1990. Any primer specific to an EPSPS locus or the sequences immediately adjacent to an EPSPS locus may be utilized to amplify the EPSPS sequences within the pooled DNA sample. Preferably, the primer is designed to amplify the regions of the EPSPS loci where useful mutations are most likely to arise. Most preferably, the primer is designed to amplify the conserved region of the EPSPS gene that codes for the enzyme's active domain. This region of the EPSPS enzyme is well known in the art (Padgette et al., *The Journal of Biological Chemistry* 266(33):22364-22369, 1991; Schonbrunn et al., *Proceedings of the National Academy of Sciences* 98(4):1376-1380, 2001; Funke et al., The Journal of Biological Chemistry 284(15):9854-9860, 2009). Additionally, it is preferable for the primer to avoid known polymorphic sites in order to ease screening for point mutations. In one embodiment, the primers are designed to amplify only one of the homoeologs so that only one homoeolog at a time is screened for mutations. The primers can be targeted to polymorphic sites between the homoeologs, so that they only amplify one of the homoeologs To facilitate detection of PCR products on a gel, the PCR primer may be labeled using any conventional or hereafter devised labeling method.

In one embodiment, Oryza sativa (rice) EPSPS cDNA (SEQ ID NO:1; NCBI Reference Sequence NM_001063247) and genomic DNA (SEQ ID NO: 2; NCBI Reference Sequence NC_008399) sequences were aligned against wheat expressed sequence tags (ESTs) in GenBank using NCBI's Basic Local Alignment Search Tool for nucleotides (BLASTN) and a Unigene cluster of ESTs (Ta. 12687; retired and replaced by Ta. 17912) was identified. The Unigene sequences were then aligned with the rice EPSPS cDNA and genomic DNA sequences and the PCR primers (SEQ ID NOs 4-5) shown in Table 1 were designed to amplify a region of the wheat EPSPS gene that coded for the active domain of the enzyme. These PCR primers were used to amplify EPSPS from wheat genomic DNAs that were prepared from the wild type tetraploid and hexaploid cultivars, Kronos (*Triticum turgidum, Durum*) and Express (*Triticum aestivum*, PVP #9000012), respectively.

TABLE 1

Exemplary Genomic Sequencing Primers

| SEQ ID | Primer Name | Primer ID | Sequence |
|---|---|---|---|
| 4 | TaEPS1CL | 3155 | ACAGTGAGGATGTCCACTACATGCTTGA |
| 5 | TaEPS1ER | 3158 | AAATAGCTCGCACTTGAGGCATCACCTT |

PCR amplification products were cloned using a TOPO Ta Cloning® Kit (with pCR® 2.1-TOPO) (Invitrogen, Carlsbad, Calif. 92008) although any suitable cloning vector could be used. Multiple independent clones were sequenced. Two categories of sequences were identified in genomic DNA from Kronos. These two plus an additional sequence category were identified in Express genomic DNA. These were presumed to represent the three wheat EPSPS homoeologues. Based on an expected synteny with the rice genome, the wheat EPSPS A and D genome copies were expected to be localized on chromosomes 7A and 7D while the B genome copy was expected to be on chromosome 4A due to a known translocation of a portion of chromosome 7B (http://wheat.pw.usda.gov/NSF/project/mapping data). With this in mind, genomic DNAs were amplified from the Chinese Spring nullisomic/tetrasomic wheat lines containing altered chromosome complements of homoeologous groups 7 A, B, D and 4 A using the same PCR primers (SEQ ID NOs: 4-5) and the PCR amplification products were sequenced. The same three EPSPS sequence categories were identified in the nullisomic/tetrasomic lines as were identified in Express. The resulting sequences were determined to represent novel partial genomic sequences for the EPSPS homoeologous genes in wheat (SEQ ID NOs: 6-8).

In another embodiment, primers were then designed to amplify specifically each EPSPS homoeologue based upon nucleotide differences that were identified in the three partial genomic sequences. Exemplary PCR primers (SEQ ID NOs: 9-12) that have proven useful in identifying useful mutations within the EPSPS sequences are shown below in Table 2. The A homoeologue of EPSP was amplified using SEQ ID NO: 9 as the left primer in combination with SEQ ID NO: 10 as the right primer. The B homoeologue of EPSP was amplified using SEQ ID NO: 9 as the left primer in combination with SEQ ID NO: 11 as the right primer and this PCR product was further screened using the TaqMan protocol as described below. The D homoeologue of EPSP was amplified using SEQ ID NO: 9 as the left primer in combination with SEQ ID NO: 12 as the right primer.

TABLE 2

Exemplary Primers Useful for Detection of Preferred Mutations

| SEQ ID | Primer Name | Primer ID | Primer Sequence |
|---|---|---|---|
| 10 | TaEPS1CL | 3155 | ACAGTGAGGATGTCCACTACATGCTTGA |
| 11 | Ep486AR | 3418 | ACTTCTCTGACAGAGAACAGAAGTGTGCAC |

TABLE 2-continued

Exemplary Primers Useful for Detection of Preferred Mutations

| SEQ ID | Primer Name | Primer ID | Primer Sequence |
|---|---|---|---|
| 12 | Ep558BR | 3419 | TTGTGTAAGGTCGCATTGATCGTACTACCA |
| 13 | TaEpsJR | 3223 | GAAAACTAGAATCATGCTTTTGTACTCCACTATC |

The PCR amplification products from the various primer combinations were sequenced to confirm that the primer pairs specifically amplified the desired homoeologues. The PCR products then were used to screen for EPSPS mutations in each homoeologue.

In another embodiment, the PCR amplification products may be screened for EPSPS mutations using any method that identifies nucleotide differences between wild type and mutant sequences. These may include, for example, without limitation, sequencing, denaturing high pressure liquid chromatography (dHPLC), constant denaturant capillary electrophoresis (CDCE), temperature gradient capillary electrophoresis (TGCE) (see Li et al., *Electrophoresis* 23(10):1499-1511, 2002), or by fragmentation using enzymatic cleavage, such as used in the high throughput method described by Colbert et al., *Plant Physiology* 126:480-484, 2001. Preferably the PCR amplification products are incubated with an endonuclease that preferentially cleaves mismatches in heteroduplexes between wild type and mutant sequences.

In another embodiment, cleavage products are electrophoresed using an automated sequencing gel apparatus, and gel images are analyzed with the aid of a standard commercial image-processing program. PCR amplification products may also be screened for single nucleotide polymorphisms using a TaqMan® SNP Genotyping Assay (Protocol Number 4332856C from Applied Biosystems, Foster City, Calif.).

TABLE 3

TaqMan Primers Useful for T173I Mutation Detection

| SEQ ID | Primer Name | Primer Sequence |
|---|---|---|
| 14 | HT_TtoI-TtoIF | ACGCCAAAGAGGAAGTAAAGCT |
| 15 | HT_TtoI-TtoIR | TCCAAACATACCCATGGATCTCATACT |
| 16 | HT_TtoI-TtoIV2 VIC | CGCATTGCAGTTCCA |
| 17 | HT_TtoI-TtoIM2 FAM | CATTGCAATTCCA |

In one embodiment, mutations disclosed and contemplated herein include missense mutations in the active domains of the EPSPS enzymes that should decrease the binding of glyphosate with minimal alterations in the binding of the endogenous substrates, including phosphoenolpyruvic acid (PEP) and 3-phophoshikimic acid.

In one embodiment, mutations in wheat EPSPS gene include a mutation that results in a change from threonine to isoleucine at amino acid position 173 (referred to herein as the T173I mutation), a mutation that results in a change from proline to serine at amino acid position 177 (referred to herein as the P177S mutation), and a mutation that results in a change from proline to leucine at amino acid position 177 (referred to herein as the P177L mutation) For clarity, the mutated amino acids in the wheat EPSPS protein are numbered according to the published rice EPSPS protein sequence (SEQ ID NO: 3). Preferred mutations also include other mutations in the EPSPS enzymes' active domain that alter enzyme activity as described above. Each novel mutation is evaluated in order to predict its impact on protein function (i.e., completely tolerated to loss-of-function) using bioinformatics tools such as SIFT (Sorting Intolerant from Tolerant; Ng and Henikoff, *Nucleic Acids Research* 31:3812-3814, 2003), PSSM (Position-Specific Scoring Matrix; Henikoff and Henikoff, *Computer Applications in the Biosciences* 12:135-143, 1996) and PARSESNP (Taylor and Greene, *Nucleic Acids Research* 31:3808-3811, 2003). For example, a SIFT score that is less than 0.05 and a large change in PSSM score (e.g., roughly 10 or above) indicate a mutation that is likely to have a deleterious effect on protein function.

A. EPSPS Gene

In one embodiment, the disclosure relates to one or more non-transgenic mutations in the EPSPS gene. In another embodiment, the disclosure relates to one or more mutations in the EPSPS gene. In one embodiment, the disclosure relates to multiple non-transgenic mutations in the EPSPS gene including but not limited to 1, 2, 3, 4, 5, 6, 7, 8, 9, 10, and greater than 10 mutations.

In another embodiment, the EPSPS gene may contain one or more non-transgenic mutations that results in a polypeptide having one or more mutations recited in Table 4 and corresponding mutations in homoeologues and combinations thereof.

In another embodiment, the disclosure relates to corresponding mutations to the one or more non-transgenic mutations disclosed herein in the EPSPS gene in a corresponding homoeologue. By way of example, an identified mutation in the EPSPS gene of the A genome may be a beneficial mutation in the EPSPS gene of the B and/or D genome. One of ordinary skill in the art will understand that the mutation in the homoeologue may not be in the exact same location.

One of ordinary skill in the art understands that there may be natural variation in the genetic sequences of the EPSPS genes in different wheat varieties.

The inventors have determined that to achieve plants with resistance to glyphosate, mutations that alter EPSPS gene function are desirable. Preferred mutations include missense and nonsense changes, including mutations that prematurely truncate the translation of one or more EPSPS proteins from messenger RNA, such as those mutations that create a stop codon within the coding region of an EPSPS messenger RNA. Such mutations include insertions, repeat sequences, splice junction mutations, modified open reading frames (ORFs) and point mutations.

In still another embodiment, one or more mutations are in the EPSPS gene of the A genome. In another embodiment, one or more mutations are in the EPSPS gene of the B genome. In still another embodiment, one or more mutations are in the EPSPS gene of the D genome. In yet another embodiment, one or more mutations are in the EPSPS genes of the A and B genomes. In still another embodiment, one or more mutations are in the EPSPS genes of the A and D genomes. In another embodiment, one or more mutations are in the EPSPS genes of the B and D genomes. In yet another embodiment, one or more mutations are in the EPSPS genes of the A, B, and D genomes.

1. A Genome

In one embodiment, the disclosure relates to multiple non-transgenic mutations in the EPSPS gene of the A genome including but not limited to 1, 2, 3, 4, 5, 6, 7, 8, 9, 10, and greater than 10 mutations. In one embodiment, one or more non-transgenic mutations are in both alleles of the EPSPS gene in the A genome. In another embodiment, the non-transgenic mutations are identical in both alleles of the EPSPS gene of the A genome. In one embodiment, the mutations are homozygous.

The following mutations identified in Table 4 are exemplary of the mutations created and identified according to various embodiments disclosed herein. They are offered by way of illustration, not limitation. It is to be understood that the mutations below are merely exemplary and that similar mutations are also contemplated.

Table 4 provides a list of representative mutations in the EPSPS gene in the A, B, and D genomes. Amino acid changes are identified according to both the published rice protein sequence, SEQ ID NO: 3, as well as the wheat protein sequence, SEQ ID NO: 9.

TABLE 4

Representative mutations in the Wheat EPSPS gene in the A, B, and D genomes.

| Cultivar | Genome | Amino Acid Change (SEQ ID NO: 3) | Amino Acid Change (SEQ ID NO: 9) | PSSM Score | SIFT Score | DNA Mutation Score |
|---|---|---|---|---|---|---|
| Express | A | M175I | M170I | 7.6 | 0.44 | Missense |
| Express | A | P177S | P172S | 10.3 | 0.02 | Severe Missense |
| Express | A | A181T | A176T | 6.0 | 0.06 | Missense |
| Express | A | A171V | A166V | 5.5 | 0.20 | Missense |
| Express | A | R176W | R171W | 28.0 | 0.00 | Severe Missense |
| Express | A | G169S | G164S | 15 | 0 | Severe Missense |
| Express | A | A185T | A180T |  | 0.38 | Missense |
| Express | B | A174V | A169V | 5.5 | 0.20 | Missense |
| Express | B | T179M | T174M | 18.3 | 0.01 | Severe Missense |
| Express | B | VI82I | V177I | 14.2 | 0.02 | Severe Missense |
| Express | B | A181V | A176V | 8.4 | 0.1 | Missense |
| Express | B | A184T | A179T | 16.3 | 0.04 | Severe Missense |
| Express | B | G172R | G167R | 17 | 0 | Severe Missense |
| Express | B | T173I | T168I | 13.1 | 0.05 | Severe Missense |
| Express | B | G169S | G164S | 15 | 0 | Severe Missense |
| Express | B | A171T | A166T | 13 | 0 | Severe Missense |
| Express | B | M175I | M171I | 10.6 | 0.08 | Missense |
| Express | B | A180T | A175T | 21.7 | 0 | Severe Missense |
| Express | B | V196L | V191L | 18.1 | 0.04 | Severe Missense |
| Express | B | R198K | R193K | 20 | 0.01 | Severe Missense |
| Express | B | M199I | M194I | 24 | 0 | Severe Missense |

TABLE 4-continued

Representative mutations in the Wheat EPSPS gene in the A, B, and D genomes.

| Cultivar | Genome | Amino Acid Change (SEQ ID NO: 3) | Amino Acid Change (SEQ ID NO: 9) | PSSM Score | SIFT Score | DNA Mutation Score |
|---|---|---|---|---|---|---|
| Express | B | V209I | V204I | 8.4 | 0 | Severe Missense |
| Express | B or D | M175I | M171I | 11.0 | 0.09 | Missense |
| Express | D | T173I | T168I | 13.9 | 0.00 | Severe Missense |
| Express | B | P177L | P172L |  |  |  |
| Kronos | A | M175I | M171I | 7.6 | 0.44 | Missense |
| Kronos | A | G195D | G190D | 26.9 | 0 | Severe Missense |
| Kronos | B | A184T | A179T | 2.7 | 0.35 | Missense |
| Express | A | P177S -A T173I -A | P172S -A T168I -A |  |  |  |
| Express | D | P177S -D T173I -D | P172S -D T168I -D |  |  |  |
| Express | A and D | P177S -A T173I -A P177S -D T173I -D | P172S -A T168I -A P172S -D T168I -D |  |  |  |
| Express | A and D | P177S -A T173I -A T173I -D | P172S -A T168I -A T168I -D |  |  |  |
| Express | A and D | P177S -A P177S -D T173I -D | P172S -A P172S -D T168I -D |  |  |  |
| Express | A, B, and D | P177S -A T173I -A T173I -B P177S -D T173I -D | P172S -A T168I -A T168I -B P172S -D T168I -D |  |  |  |
| Express | A, B, and D | P177S-A T173I-A T173I-B T173I-D | P172S-A T168I-A T168I-B T168I-D |  |  |  |
| Express | A, B, and D | T173I -A T173I -B P177S -D T173I -D | T168I -A T168I -B P172S -D T168I -D |  |  |  |
| Express | A, B, and D | T173I -A P177S-A P177L -B P177S -D T173I -D | T168I -A P172S-A P172L -B P172S -D T168I -D |  |  |  |

In one embodiment, two or more mutations identified in the A genome and recited in Table 4 can be combined so that the A genome contains two or more mutations.

In another embodiment, two or more mutations identified in the B genome and recited in Table 4 can be combined so that the B genome contains two or more mutations.

In yet another embodiment, two or more mutations identified in the D genome and recited in Table 4 can be combined so that the D genome contains two or more mutations.

TABLE 5

Representative combination mutations in Wheat EPSPS gene of the A, B, and D genomes.

| Cultivar | Genome | Mutation (location on SEQ ID NO: 3) | Mutation (location on SEQ ID NO: 9) |
|---|---|---|---|
| Express | A | P177S -A T173I -A | P172S -A T168I -A |
| Express | D | P177S -D T173I -D | P172S -D T168I -D |

TABLE 5-continued

Representative combination mutations in Wheat EPSPS gene of the A, B, and D genomes.

| Cultivar | Genome | Mutation (location on SEQ ID NO: 3) | Mutation (location on SEQ ID NO: 9) |
|---|---|---|---|
| Express | A and D | P177S -A<br>T173I -A<br>P177S -D<br>T173I -D | P172S -A<br>T168I -A<br>P172S -D<br>T168I -D |
| Express | A and D | P177S -A<br>T173I -A<br>P177S -D | P172S -A<br>T168I -A<br>P172S -D |
| Express | A and D | P177S -A<br>T173I -A<br>T173I -D | P172S -A<br>T168I -A<br>T168I -D |
| Express | A and D | P177S -A<br>P177S -D<br>T173I -D | P177S -A<br>P177S -D<br>T173I -D |
| Express | A and D | T173I -A<br>P177S -D<br>T173I -D | T168I -A<br>P172S -D<br>T168I -D |
| Express | A, B, and D | P177S -A<br>T173I -A<br>T173I -B<br>P177S -D<br>T173I -D | P172S -A<br>T168I -A<br>T168I -B<br>P172S -D<br>T168I -D |
| Express | A, B, and D | P177S-A<br>T173I-A<br>T173I-B<br>T173I-D | P172S-A<br>T168I-A<br>T168I-B<br>T168I-D |
| Express | A, B, and D | P177S-A<br>T173I-A<br>T173I-B<br>P177S -D | P172S-A<br>T168I-A<br>T168I-B<br>P172S-D |
| Express | A, B, and D | P177S-A<br>T173I-B<br>P177S-D<br>T173I-D | P172S-A<br>T168I-B<br>P172S-D<br>T168I-D |
| Express | A, B, and D | T173I -A<br>T173I -B<br>P177S -D<br>T173I -D | T168I -A<br>T168I -B<br>P172S -D<br>T168I -D |
| Express | A, B, and D | P177S -A<br>P177L -B<br>T173I -D | P172S -A<br>P172L -B<br>T168I -D |

In one embodiment, any mutations identified in the A genome in Table 4 can be combined with any mutation in the B genome recited in Table 4.

TABLE 6

Representative combinations of wheat plants with mutations in the EPSPS gene in both the A and B genomes. Amino acid designation corresponds to the amine position in SEQ ID NO: 9.

| Cultivar | A Genome | B genome |
|---|---|---|
| Express/Kronos | P172S | T174M |
| Express/Kronos | P172S | V177I |
| Express/Kronos | P172S | A176V |
| Express/Kronos | P172S | A179T |
| Express/Kronos | P172S | G167R |
| Express/Kronos | P172S | T168I |
| Express/Kronos | P172S | G164S |
| Express/Kronos | P172S | A166T |
| Express/Kronos | P172S | M171I |
| Express/Kronos | P172S | A175T |
| Express/Kronos | P172S | V191L |
| Express/Kronos | P172S | R193K |
| Express/Kronos | P172S | M194I |
| Express/Kronos | P172S | V205I |
| Express/Kronos | P172S | M170I |
| Express/Kronos | M170I | T168I |
| Express/Kronos | P172S | T168I |
| Express/Kronos | A176T | T168I |
| Express/Kronos | A166V | T168I |
| Express/Kronos | R171W | T168I |
| Express/Kronos | G164S | T168I |
| Express/Kronos | A181T | T168I |

In another embodiment, any mutations identified in the A genome in Table 4 can be combined with any mutation in the D genome recited in Table 4.

TABLE 7

Representative combinations of wheat plants with mutations in the EPSPS gene of the A and D genomes. Amino acid designation corresponds to the amino acid position in SEQ ID NO: 9.

| Cultivar | A Genome | D genome |
|---|---|---|
| Express/Kronos | P172S | T168I |
| Express/Kronos | M170I | T168I |
| Express/Kronos | P172S | T168I |
| Express/Kronos | A176T | T168I |
| Express/Kronos | A166V | T168I |
| Express/Kronos | R171W | T168I |
| Express/Kronos | G164S | T168I |
| Express/Kronos | A180T | T168I |

In yet another embodiment, any mutations identified in the A genome in Table 4 can be combined with any mutation in the B genome in Table 4 and any mutation in the D genome recited in Table 4.

TABLE 8

Representative combinations of wheat plants with mutations in the EPSPS gene in the A, B, and D genomes. Amino acid designation corresponds to the amino acid position in SEQ ID NO: 9.

| Cultivar | A Genome | B genome | D genome |
|---|---|---|---|
| Express/Kronos | P172S | T174M | T168I or M170I |
| Express/Kronos | P172S | V177I | T168I or M170I |
| Express/Kronos | P172S | A176V | T168I or M170I |
| Express/Kronos | P172S | A179T | T168I or M170I |
| Express/Kronos | P172S | G167R | T168I or M170I |
| Express/Kronos | P172S | T168I | T168I or M170I |
| Express/Kronos | P172S | G164S | T168I or M170I |
| Express/Kronos | P172S | A166T | T168I or M170I |
| Express/Kronos | P172S | M170I | T168I or M170I |
| Express/Kronos | P172S | A175T | T168I or M170I |
| Express/Kronos | P172S | V191L | T168I or M170I |
| Express/Kronos | P172S | R193K | T168I or M170I |
| Express/Kronos | P172S | M194I | T168I or M170I |
| Express/Kronos | P172S | V204I | T168I or M170I |
| Express/Kronos | P172S | M170I | T168I or M170I |
| Express/Kronos | M170I | T168I | T168I or M170I |
| Express/Kronos | P172S | T168I | T168I or M170I |
| Express/Kronos | A166T | T168I | T168I or M170I |
| Express/Kronos | A166V | T168I | T168I or M170I |
| Express/Kronos | R171W | T168I | T168I or M170I |
| Express/Kronos | G164S | T168I | T168I or M170I |
| Express/Kronos | A180T | T168I | T168I or M170I |

In another embodiment, any mutations identified in the B genome in Table 4 can be combined with any mutation in the D genome recited in Table 4.

In one embodiment, the disclosure relates to a polynucleotide of the EPSPS gene in the A genome corresponding to SEQ ID NO: 6 with one or more non-transgenic mutations that produces a polypeptide with one or more mutations recited in Table 4. In another embodiment, the polynucleotide that codes for a polypeptide with one or more non-transgenic mutations listed in Table 4 has 85%, 86%, 87%, 88%, 89%, 90%, 91%, 92%, 93%, 94%, 95%, 96%, 97%, 98%, 99% or greater than 99% identity to SEQ ID NO: 6.

In still another embodiment, the polynucleotide codes for an EPSPS protein with one or more non-transgenic mutation listed in Table 4, wherein the EPSPS protein comprises one or more non-transgenic mutations and has 85%, 86%, 87%, 88%, 89%, 90%, 91%, 92%, 93%, 94%, 95%, 96%, 97%, 98%, 99% or greater than 99% identity to the EPSPS-A protein.

2. B Genome

In one embodiment, the disclosure relates to multiple non-transgenic mutations in the EPSPS gene of the B genome including but not limited to 1, 2, 3, 4, 5, 6, 7, 8, 9, 10, and greater than 10 mutations. In one embodiment, one or more non-transgenic mutations are in both alleles of the EPSPS gene in the B genome. In another embodiment, the non-transgenic mutations are identical in both alleles of the EPSPS gene of the B genome. In still another embodiment, the mutations are homozygous.

In one embodiment, the disclosure relates to a polynucleotide of the EPSPS gene in the B genome corresponding to SEQ ID NO: 7 with one or more non-transgenic mutations that codes for a polypeptide with one or more mutations listed in Table 4. In another embodiment, the polynucleotide with one or more non-transgenic mutations codes for a polypeptide having one or more mutations recited in Table 4, and has 85%, 86%, 87%, 88%, 89%, 90%, 91%, 92%, 93%, 94%, 95%, 96%, 97%, 98%, 99% or greater than 99% identity to SEQ ID NO: 7.

In still another embodiment, the disclosure relates to a polynucleotide of the EPSPS gene in the B genome with one or more non-transgenic mutation that codes for a polypeptide with one or more non-transgenic mutations and has 85%, 86%, 87%, 88%, 89%, 90%, 91%, 92%, 93%, 94%, 95%, 96%, 97%, 98%, 99% or greater than 99% identity to the EPSPS-B protein.

3. D Genome

In one embodiment, the disclosure relates to multiple non-transgenic mutations in the EPSPS gene of the D genome including but not limited to 1, 2, 3, 4, 5, 6, 7, 8, 9, 10, and greater than 10 mutations. In one embodiment, one or more non-transgenic mutations are in both alleles of the EPSPS gene in the D genome. In another embodiment, the non-transgenic mutations are identical in both alleles of the EPSPS gene of the D genome. In still another embodiment, the mutations are homozygous.

In one embodiment, the disclosure relates to a polynucleotide of the EPSPS gene in the D genome corresponding to SEQ ID NO: 8 with one or more non-transgenic mutations that codes for a polypeptide with one or more mutations listed in Table 4. In another embodiment, the polynucleotide with one or more non-transgenic mutations codes for a polypeptide having one or more mutations recited in Table 4, and has 85%, 86%, 87%, 88%, 89%, 90%, 91%, 92%, 93%, 94%, 95%, 96%, 97%, 98%, 99% or greater than 99% identity to SEQ ID NO: 8.

In still another embodiment, the disclosure relates to a polynucleotide of the EPSPS gene in the D genome with one or more non-transgenic mutation that codes for a polypeptide with one or more non-transgenic mutations and has 85%, 86%, 87%, 88%, 89%, 90%, 91%, 92%, 93%, 94%, 95%, 96%, 97%, 98%, 99% or greater than 99% identity to the EPSPS-D protein.

B. EPSPS Proteins

In yet another embodiment, the disclosure relates to one or more non-transgenic mutations in the EPSPS gene (as discussed above in the section entitled EPSPS Mutations) that result in a EPSPS protein with one or more mutations as compared to wild type EPSPS protein. In one embodiment, the non-transgenic mutations include but are not limited to the mutations recited in Table 4, corresponding mutations in homoeologues, and combinations thereof.

In another embodiment, the disclosure relates to one or more non-transgenic mutations in the EPSPS gene that results in an EPSPS protein with reduced affinity for glyphosate. In some embodiments, a mutation in the EPSPS gene reduces expression of the EPSPS protein. In other embodiments, a mutation in the EPSPS gene creates an unstable or a EPSPS protein with reduced function.

1. Expression Level of EPSPS Protein

In another embodiment, the expression level of EPSPS protein with one or more mutations disclosed herein is reduced by 0-2%, 2-5%, 5-7%, 7-10%, 10-15%, 15-20%, 20-25%, 25-30%, 30-35%, 35-40%, 40-45%, 45-50%, 50-60%, 60-70%, 70-80%, 80-90%, 90-95%, and 95-99% of the expression level of the wild type EPSPS protein.

In still another embodiment, the expression level of EPSPS protein with one or more mutations disclosed herein is reduced from 10-20%, or from 20-30%, or from 30-40%, or from 40-50%, or from 50-60%, or from 60-70%, or from 70-80%, or from 80-90%, or from 90-99% as compared to the expression level of the wild type EPSPS protein.

2. Activity of EPSPS Protein

In yet another embodiment, the EPSPS protein with one or more mutations disclosed herein has reduced affinity for glyphosate, wherein the reduced affinity is 0-1, 1, 2, 3, 4, 5, 6, 7, 8, 9, 10, 11, 12, 13, 14,15, 16, 17,18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99% and by more than 99% of the affinity of the wild type EPSPS protein for glyphosate. In another embodiment, the EPSPS protein with one or more mutations disclosed herein has no affinity or zero affinity for glyphosate as compared to wild type EPSPS protein.

In yet another embodiment, the EPSPS protein with one or more mutations disclosed herein has reduced affinity for glyphosate but wild type affinity for plant or endogenous substrates. In one embodiment, the EPSPS protein with one or more mutations disclosed herein has substantial affinity for plant or endogeneous substrates, wherein the affinity for plant substrates is about 100%, or 99%, or 98%, or 97%, or 96%, or 95%, or 94%, or 93%, or 92%, or 91%, or 90% as compared to wild type EPSPS protein.

In yet another embodiment, the activity of the EPSPS protein with one or more mutations disclosed herein is from 1-10% or from 10-30% or from 30-50% or from 50-70% or from 70-80% or from 80-90% or from 90-95% of the activity level of the wild type EPSPS protein.

III. Genomic Editing

In one embodiment, the disclosure relates to a plant with reduced expression of the EPSPS gene and/or reduced activity of the EPSPS protein, wherein reduced expression of the EPSPS gene and/or reduced activity of the EPSPS protein is achieved by genomic editing.

In one embodiment, the disclosure relates to a wheat plant with a genomically edited EPSPS gene, wherein the wheat plant has an altered EPSPS protein compared to a wild type plant.

Genome editing, or genome editing with engineered nucleases (GEEN), is a type of genetic engineering in which DNA is inserted, replaced, or removed from a genome using artificially engineered nucleases, or "molecular scissors." The nucleases create specific double-stranded breaks (DSBs) at desired locations in the genome, and harness the cell's endogenous mechanisms to repair the induced break by natural processes of homologous recombination (HR) and nonhomologous end-joining (NHEJ). There are currently four main families of engineered nucleases being used: Zinc finger nucleases (ZFNs), Transcription Activator-Like Effector Nucleases (TALENs), the CRISPR/Cas system, and engineered meganuclease with a re-engineered homing endonucleases.

A. Zinc Finger Nucleases (ZFNs)

Zinc-finger nucleases (ZFNs) are artificial restriction enzymes generated by fusing a zinc finger DNA-binding domain to a DNA-cleavage domain. Zinc finger domains can be engineered to target specific desired DNA sequences and this enables zinc-finger nucleases to target unique sequences within complex genomes. By taking advantage of endogenous DNA repair machinery, these reagents can be used to precisely alter the genomes of higher organisms.

ZFNs consist of an engineered zinc finger DNA-binding domain fused to the cleavage domain of the FokI restriction endonuclease. ZFNs can be used to induce double-stranded breaks (DSBs) in specific DNA sequences and thereby promote site-specific homologous recombination with an exogenous template. The exogenous template contains the sequence that is to be introduced into the genome.

Publicly available methods for engineering zinc finger domains include: (1) Context-dependent Assembly (CoDA), (2) Oligomerized Pool Engineering (OPEN), and (3) Modular Assembly.

In one embodiment, the disclosure relates to increasing the glyphosate tolerance of the EPSPS gene and its encoded enzyme using ZFNs.

B. Transcription Activator-Like Effector Nucleases (TALENs)

TALEN is a sequence-specific endonuclease that consists of a transcription activator-like effector (TALE) and a FokI endonuclease. TALE is a DNA-binding protein that has a highly conserved central region with tandem repeat units of 34 amino acids. The base preference for each repeat unit is determined by two amino acid residues called the repeat-variable di-residue (RVD), which recognizes one specific nucleotide in the target DNA. Arrays of DNA-binding repeat units can be customized for targeting specific DNA sequences. As with ZFNs, dimerization of two TALENs on targeted specific sequences in a genome results in FokI-dependent introduction of DSBs, stimulating homology directed repair (HDR) and Non-homologous end joining (NHEJ) repair mechanisms.

In one embodiment, the disclosure relates to increasing the glyphosate tolerance of the EPSPS gene and its encoded enzyme using TALENs.

C. CRISPR/Cas System

The Clustered Regularly Interspaced Short Palindromic Repeats (CRISPR) Type II system is an RNA-Guided Endonuclease technology for genome engineering. There are two distinct components to this system: (1) a guide RNA and (2) an endonuclease, in this case the CRISPR associated (Cas) nuclease, Cas9.

The guide RNA is a combination of the endogenous bacterial crRNA and tracrRNA into a single chimeric guide RNA (gRNA) transcript. The gRNA combines the targeting specificity of the crRNA with the scaffolding properties of the tracrRNA into a single transcript. When the gRNA and the Cas9 are expressed in the cell, the genomic target sequence can be modified or permanently disrupted.

The gRNA/Cas9 complex is recruited to the target sequence by the base-pairing between the gRNA sequence and the complementarity to the target sequence in the genomic DNA. For successful binding of Cas9, the genomic target sequence must also contain the correct Protospacer Adjacent Motif (PAM) sequence immediately following the target sequence. The binding of the gRNA/Cas9 complex localizes the Cas9 to the genomic target sequence so that the wild-type Cas9 can cut both strands of DNA causing a Double Strand Break (DSB). Cas9 will cut 3-4 nucleotides upstream of the PAM sequence. A DSB can be repaired through one of two general repair pathways: (1) NHEJ DNA repair pathway or (2) the HDR pathway. The NHEJ repair pathway often results in insertions/deletions (InDels) at the DSB site that can lead to frameshifts and/or premature stop codons, effectively disrupting the open reading frame (ORF) of the targeted gene.

The HDR pathway requires the presence of a repair template, which is used to fix the DSB. HDR faithfully copies the sequence of the repair template to the cut target sequence. Specific nucleotide changes can be introduced into a targeted gene by the use of HDR with a repair template.

In one embodiment, the disclosure relates to increasing the glyphosate tolerance of the EPSPS gene and its encoded enzyme using the CRISPR/cas9 system.

D. Meganuclease with Re-Engineered Homing Nuclease

Meganucleases are endodeoxyribonucleases characterized by a large recognition site (double-stranded DNA sequences of 12 to 40 base pairs); as a result this site generally occurs only once in any given genome. For example, the 18-base pair sequence recognized by the I-SceI meganuclease would on average require a genome twenty times the size of the human genome to be found once by chance (although sequences with a single mismatch occur about three times per human-sized genome). Meganucleases are therefore considered to be the most specific naturally occurring restriction enzymes.

Among meganucleases, the LAGLIDADG family of homing endonucleases has become a valuable tool for the study of genomes and genome engineering over the past fifteen years. By modifying their recognition sequence through protein engineering, the targeted sequence can be changed.

In one embodiment, the disclosure relates to increasing the glyphosate tolerance of the EPSPS gene and its encoded enzyme using a meganuclease with a re-engineered homing nuclease.

IV. Wheat Cultivars

In one embodiment, a wheat cultivar having at least one EPSPS gene that is diploid, polyploid, tetraploid, and hexaploid may be used.

In another embodiment, the wheat is Triticum aestivum.

In one embodiment, any cultivar of wheat can be used to create mutations in an EPSPS gene. In one embodiment, any cultivar of wheat can be used to create mutations in the EPSPS gene of the A genome. In another embodiment, any cultivar of wheat can be used to create mutations in the EPSPS gene of the B genome. In another embodiment, any cultivar of wheat can be used to create mutations in the EPSPS gene of the D genome.

In one embodiment, any cultivar of wheat can be used as lines to cross EPSPS mutations into different cultivars. In another embodiment, any cultivar of wheat having at least one EPSPS gene may be used including but not limited to hard red spring wheat, hard white wheat, durum wheat, soft white spring wheat, soft white winter wheat, hard red winter wheat, common wheat, club wheat, spelt wheat, emmer wheat, pasta wheat and turgidum wheat.

In one embodiment, hard red spring wheat includes but is not limited to Bullseye, Cabernet, Cal Rojo, Hank, Joaquin, Kelse, Lariat, Lassik, Malbec, Mika, PR 1404, Redwing, Summit 515, SY 314, Triple IV, Ultra, WB-Patron, WB-Rockland, Yecora Rojo, Accord, Aim, Anza, Baker, Beth Hashita, Bonus, Borah, Brim, Brooks, Buck Pronto, Butte 86, Cavalier, Challenger, Chief, Ciano T79, Colusa, Companion, Copper, Cuyama, Dash 12, Eldon, Enano, Express, Expresso, Jefferson, Genero F81, Grandin, Helena 554, Hollis, Imuris T79, Inia 66R, Jerome, Kern, Len, Marshall, McKay, Nomad, Northwest 10, Oslo, Pavon F76, Pegasus, Pitic 62, Poco Red, Powell, Probrand 711, Probrand 751, Probrand 771, Probrand 775, Probred, Prointa Queguay, Prointa Quintal, Rich, RSI 5, Sagittario, Scarlet, Serra, Shasta, Solano, Spillman, Sprite, Stander, Stellar, Stoa, Success, Summit, Sunstar 2, Sunstar King, Tadinia, Tammy, Tanori 71, Tara 2000, Tempo, Tesia T79, Topic, UI Winchester, Vance, Vandal, W444, Wampum, Wared, WB-Fuzion, Westbred 906R, Westbred 911, Westbred 926, Westbred 936, Westbred Discovery, Westbred Rambo, Yolo, and Zeke.

In another embodiment, hard white wheat includes but is not limited to Blanca Fuerte, Blanca Grande 515, Blanca Royale, Clear White, Patwin, Patwin 515, WB-Cristallo, WB-Paloma, WB-Perla, Alta Blanca, Blanca Grande, Delano, Golden Spike, ID377S, Klasic, Lochsa, Lolo, Macon, Otis, Phoenix, Pima 77, Plata, Pristine, Ramona 50, Siete Cerros 66, Vaiolet, and Winsome.

In yet another embodiment, durum wheat includes but is not limited to Crown, Desert King, Desert King HP, Duraking, Fortissimo, Havasu, Kronos, Maestrale, Normanno, Orita, Platinum, Q-Max, RSI 59, Saragolla, Tango, Tipai, Topper, Utopia, Volante, WB-Mead, Westmore, Aldente, Aldura, Altar 84, Aruba, Bittern, Bravadur, Candura, Cortez, Deluxe, Desert Titan, Durex, Durfort, Eddie, Germains 5003D, Imperial, Kofa, Levante, Matt, Mead, Mexicali 75, Minos, Modoc, Mohawk, Nudura, Ocotillo, Produra, Reva, Ria, Septre, Sky, Tacna, Titan, Trump, Ward, Westbred 803, Westbred 881, Westbred 883, Westbred 1000D, Westbred Laker, Westbred Turbo, and Yavaros 79.

In another embodiment, soft white spring wheat includes but is not limited to Alpowa, Alturas, Babe, Diva, JD, New Dirkwin, Nick, Twin,Whit, Blanca, Bliss, Calorwa, Centennial, Challis, Dirkwin, Eden, Edwall, Fielder, Fieldwin, Jubilee, Louise, Owens, Penawawa, Pomerelle, Sterling, Sunstar Promise, Super Dirkwin, Treasure, UI Cataldo, UI Pettit, Urquie, Vanna, Waduel, Waduel 94, Wakanz, Walladay, Wawawai, Whitebird, and Zak.

In still another embodiment, soft white winter wheat includes but is not limited to AP Badger, AP Legacy, Brundage 96, Bruneau, Cara, Goetze, Legion, Mary, Skiles, Stephens, SY Ovation, Tubbs, WB-Junction, WB-528, Xerpha, Yamhill, Barbee, Basin, Bitterroot, Bruehl, Castan, Chukar, Coda, Daws, Edwin, Eltan, Faro, Finch, Foote, Gene, Hill 81, Hiller, Hubbard, Hyak, Hyslop, Idaho 587, Kmor, Lambert, Lewjain, MacVicar, Madsen, Malcolm, Masami, McDermid, Moro, Nugaines, ORCF-101, ORCF-102, ORCF-103, Rod, Rohde, Rulo, Simon, Salute, Temple, Tres, Tubbs 06, UICF-Brundage, WB-523, and Weatherford.

In another embodiment, hard red winter wheat includes but is not limited to Andrews, Archer, Batum, Blizzard, Bonneville, Boundary, Declo, Debris, Finley, Garland, Hatton, Hoff, Longhorn, Manning, Meridian, Promontory, Vona, Wanser, Winridge.

In another embodiment, common wheat (hexaploid, free threshing), Triticum aestivum ssp aestivum includes but is not limited to Sonora, Wit Wolkoring, Chiddam Blanc De Mars, India-Jammu, Foisy.

In still another embodiment, spelt wheat (hexaploid, not free threshing), Triticum aestivum ssp spelta includes but is not limited to Spanish Spelt, Swiss Spelt.

In yet another embodiment, Emmer Wheat (tetraploid), *Triticum turgidum* ssp. *dicoccum* includes but is not limited to Ethiopian Blue Tinge.

In another embodiment, pasta wheat (tetraploid, free threshing), *Triticum turgidum* ssp *durum* includes but is not limited to Blue Beard, Durum-Iraq.

In yet another embodiment, Turgidum Wheat (tetraploid, free threshing), *Triticum turgidum* ssp turgidum includes but is not limited to Akmolinka, Maparcha.

In one embodiment, a cultivar of wheat having at least one EPSPS gene with substantial percent identity to SEQ ID NO: 6, SEQ ID NO: 7, or SEQ ID NO. 8 may be used with the methods and compositions disclosed herein.

As used herein with regard to the wheat cultivars, "substantial percent identity" means that the DNA sequence of the gene is sufficiently similar to SEQ ID NO: 6, 7, and 8 at the nucleotide level to code for a substantially similar protein, allowing for allelic differences (or alternate mRNA splicing) between cultivars. In one embodiment, "substantial percent identity" may be present when the percent identity in the coding region between the EPSPS gene and SEQ ID NO: 6, 7, and 8 is as low as about 85%, provided that the percent identity in the conserved regions of the gene is higher (e.g., at least about 90%). Preferably the percent identity in the coding region is 85-90%, more preferably 90-95%, and optimally, it is above 95%. Thus, one of skill in the art may prefer to utilize a wheat cultivar having commercial popularity or one having specific desired characteristics in which to create the EPSPS-mutated wheat plants, without deviating from the scope and intent of the disclosure. Alternatively, one of skill in the art may prefer to utilize a wheat cultivar having few polymorphisms, such as an in-bred cultivar, in order to facilitate screening for mutations within one or more EPSPS genes in accordance with the disclosure V. Representative Methodology for Identification of EPSPS Mutations One of ordinary skill in the art will appreciate that numerous techniques and methods are available for generating mutations and/or non-transgenic mutations. One representative methodology is described below.

In order to create and identify the EPSPS mutations and wheat plants disclosed herein, a method known as TILLING was utilized. See McCallum et al., Nature Biotechnology 18:455-457, 2000; McCallum et al., *Plant Physiology*, 123: 439-442, 2000; U.S. Publication No. 20040053236; and U.S. Pat. No. 5,994,075, all of which are incorporated herein by reference. In the basic TILLING methodology, plant materials, such as seeds, are subjected to chemical mutagenesis, which creates a series of mutations within the genomes of the seeds' cells. The mutagenized seeds are grown into adult M1 plants and self-pollinated. DNA samples from the resulting M2 plants are pooled and are then screened for mutations in a gene of interest. Once a mutation is identified in a gene of interest, the seeds of the M2 plant carrying that mutation are grown into adult M3 plants and screened for the phenotypic characteristics associated with that mutation in the gene of interest.

In one embodiment, the tetraploid cultivar Kronos was used. In other embodiments, the hexaploid cultivar Express was used.

In one embodiment, seeds from wheat are mutagenized and then grown into M2plants. The M1 plants are then allowed to self-pollinate and seeds from the M1 plant are grown into M2 plants, which are then screened for mutations in their EPSPS loci. While M1 plants can be screened for mutations in accordance with alternative embodiments disclosed herein, one advantage of screening the M2 plants is that all somatic mutations correspond to germline mutations.

One of skill in the art will understand that a variety of wheat plant materials, including, but not limited to, seeds, pollen, plant tissue or plant cells, may be mutagenized in order to create the EPSPS-mutated wheat plants disclosed herein. However, the type of plant material mutagenized may affect when the plant DNA is screened for mutations. For example, when pollen is subjected to mutagenesis prior to pollination of a non-mutagenized plant, the seeds resulting from that pollination are grown into M1 plants. Every cell of the M1 plants will contain mutations created in the pollen, thus these M1 plants may then be screened for EPSPS mutations instead of waiting until the M2 generation.

Mutagens that create primarily point mutations and short deletions (about 1 to about 30 nucleotides), insertions, transversions, and or transitions, such as chemical mutagens or radiation, such as x-rays and fast neutrons, may be used to create the mutations. Mutagens conforming with the methods disclosed herein include, but are not limited to, ethyl methanesulfonate (EMS), methylmethane sulfonate (MMS), N-ethyl-N-nitrosourea (ENU), triethylmelamine (TEM), N-methyl-N-nitrosourea (MNU), procarbazine, chlorambucil, cyclophosphamide, diethyl sulfate, acrylamide monomer, melphalan, nitrogen mustard, vincristine, dimethylnitrosamine, N-methyl-N'-nitro-Nitrosoguanidine (MNNG), nitrosoguanidine, 2-aminopurine, 7, 12 dimethylbenz(a)anthracene (DMBA), ethylene oxide, hexamethylphosphoramide, bisulfan, diepoxyalkanes (diepoxyoctane (DEO), diepoxybutane (DEB), and the like), 2-methoxy-6-chloro-9[3-(ethyl-2-chloro-ethyl)aminopropylamino] acridine dihydrochloride (ICR-170), sodium azide, and formaldehyde. Spontaneous mutations in a EPSPS gene that may not have been directly caused by the mutagen can also be identified.

Any suitable method of plant DNA preparation now known or hereafter devised may be used to prepare the wheat plant DNA for EPSPS mutation screening. For example, see Chen & Ronald, *Plant Molecular Biology Reporter* 17:53-57, 1999; Stewart and Via, *Bio Techniques* 14:748-749, 1993. Additionally, several commercial kits designed for this purpose are available, including kits from Qiagen (Valencia, Calif.) and Qbiogene (Carlsbad, Calif.).

In one embodiment, prepared DNA from individual wheat plants are pooled in order to expedite screening for mutations in one or more EPSPS genes of the entire population of plants originating from the mutagenized plant tissue. The size of the pooled group may be dependent upon the sensitivity of the screening method used. Preferably, groups of two or more individual wheat plants are pooled.

In another embodiment, after the DNA samples are pooled, the pools are subjected to EPSPS sequence-specific amplification techniques, such as Polymerase Chain Reaction (PCR). For a general overview of PCR, see PCR Protocols: *A Guide to Methods and Applications* (Innis, Gelfand, Sninsky, and White, eds.), Academic Press, San Diego, 1990.

Any primer specific to a EPSPS locus or the sequences immediately adjacent to one of these loci may be utilized to amplify the EPSPS sequences within the pooled DNA sample. Preferably, the primer is designed to amplify the regions of the EPSPS locus where useful mutations are most likely to arise. Most preferably, the primer is designed to detect exonic regions of one or more EPSPS genes. Additionally, it is preferable for the primer to target known polymorphic sites to design genome specific primers in order to ease screening for point mutations in a particular genome. To facilitate detection of PCR products on a gel, the PCR primer may be labeled using any conventional or hereafter devised labeling method.

In one embodiment, primers are designed based upon the EPSPS genes (SEQ ID NOs: 6, 7, and 8). In another embodiment, primers can be designed that are 5' or 3' to the EPSPS genes.

In another embodiment, the PCR amplification products may be screened for EPSPS mutations using any method that identifies nucleotide differences between wild type and mutant sequences. These may include, for example, without limitation, sequencing, denaturing high pressure liquid chromatography (dHPLC), constant denaturant capillary electrophoresis (CDCE), temperature gradient capillary electrophoresis (TGCE) (see Li et al., Electrophoresis 23(10):1499-1511, 2002), or by fragmentation using enzymatic cleavage, such as used in the high throughput method described by Colbert et al., *Plant Physiology* 126:480-484, 2001. Preferably, the PCR amplification products are incubated with an endonuclease that preferentially cleaves mismatches in heteroduplexes between wild type and mutant sequences.

In another embodiment, cleavage products are electrophoresed using an automated sequencing gel apparatus, and gel images are analyzed with the aid of a standard commercial image-processing program.

In yet another embodiment, once an M2 plant having a mutated EPSPS gene sequence is identified, the mutations are analyzed to determine their effect on the expression, translation, and/or activity of a EPSPS enzyme. In one embodiment, the PCR fragment containing the mutation is sequenced, using standard sequencing techniques, in order to determine the exact location of the mutation in relation to the overall EPSPS sequence. Each mutation is evaluated in order to predict its impact on protein function (i.e., from completely tolerated to causing loss-of-function) using bioinformatics tools such as SIFT (Sorting Intolerant from Tolerant; Ng and Henikoff, *Nucleic Acids Research* 31:3812-3814, 2003), PSSM (Position-Specific Scoring Matrix; Henikoff and Henikoff, *Computer Applications in the Biosciences* 12:135-143, 1996) and PARSESNP (Taylor and Greene, *Nucleic Acids Research* 31:3808-3811, 2003). For example, a SIFT score that is less than 0.05 and a large change in PSSM score (e.g., roughly 10 or above) indicate a mutation that is likely to have a deleterious effect on protein function. These programs are known to be predictive, and it is understood by those skilled in the art that the predicted outcomes are not always accurate.

In another embodiment, if the initial assessment of a mutation in the M2 plant indicates it to be of a useful nature and in a useful position within a EPSPS gene, then further phenotypic analysis of the wheat plant containing that mutation may be pursued. In hexaploid wheat, mutations in each of the A, B and D genomes usually must be combined before a phenotype can be detected. In tetraploid wheat, A and B genome mutations are combined. In addition, the mutation containing plant can be backcrossed or outcrossed two times or more in order to eliminate background mutations at any generation. Then, the backcrossed or outcrossed plant can be self-pollinated or crossed in order to create plants that are homozygous for the EPSPS mutations.

Several physical characteristics of these homozygous EPSPS mutant plants are assessed to determine if the mutation results in a useful phenotypic change in the wheat plant without resulting in undesirable negative effects, such as significantly reduced seed yields.

In one embodiment, seeds of the plant containing multiple preferred single mutations in EPSPS can be re-mutagenized and then the progeny can be screened to find the preferred second-site utation that increases the glyphosate tolerance above the tolerance of the single-site mutations.

VI. Methods of Producing a Wheat Plant

In another embodiment, the disclosure relates to a method for producing a wheat plant with resistance to glyphosate. In another embodiment, the disclosure relates to a method for producing a wheat plant with resistance to glyphosate.

In another embodiment, the disclosure relates to a method of out-crossing EPSPS gene mutations to wild type plants.

In still another embodiment, the disclosure relates to a method for producing a plant having one or more EPSPS proteins with reduced affinity for glyphosate as compared to the wild EPSPNS protein.

In one embodiment, the method comprises inducing at least one non-transgenic mutation in at least one copy of a EPSPS gene in plant material or plant parts from a parent plant; growing or using the mutagenized plant material to produce progeny plants; analyzing mutagenized plant material and/or progeny plants to detect at least one mutation in at least one copy of a EPSPS gene; and selecting progeny plants that have at least one mutation in at least one copy of a EPSPS gene.

In another embodiment, the method further comprises crossing progeny plants that have at least one mutation in at least one copy of a EPSPS gene with other progeny plants that have at least one mutation in a different copy of a EPSPS gene. The process of identifying progeny plants with mutations and crossing said progeny plants with other progeny plants, which have mutations, can be repeated to produce progeny wheat plants with reduced EPSPS activity.

In another embodiment, the affinity of the altered EPSPS protein in the wheat plant for glyphosate is reduced to 0-2%, 2-5%, 5-7%, 7-10%, 10-15%, 15-20%, 20-25%, 25-30%, 30-35%, 35-40%, 40-45%, 45-50%, 50-60%, 60-70%, 70-80%, 80-90%, 90-95%, or 95-99% of the affinity of EPSPS protein in the wild type plant.

A. Methods of producing a plant with one or more mutations in the EPSPS gene in more than one genome In still another embodiment, the disclosure relates to a method for producing a plant comprising the following: inducing at least one non-transgenic mutation in at least one copy of a EPSPS gene in plant material from a parent plant that comprises a mutation in a EPSPS gene; growing or using the mutagenized plant material to produce progeny plants; and selecting progeny wheat plants that have at least one mutation in at least two copies of a EPSPS gene. For example, the parent plant may have a mutation in a EPSPS gene of the A genome. The selected progeny plants may have a mutation in a EPSPS gene of the A genome and one or more mutations in the EPSPS gene of the B genome. This example is provided merely for clarification and should not limit the methods disclosed herein.

In yet another embodiment, the disclosure relates to a method for producing a plant comprising inducing at least one non-transgenic mutation in at least one copy of a EPSPS gene in plant material from a parent plant that comprises at least one mutation in two EPSPS genes; growing or using the mutagenized plant material to produce progeny plants; and selecting progeny plants that have at least one mutation in three copies of a EPSPS gene. In this embodiment, there would be at least one mutation in the EPSPS gene of the A, B and D genomes.

In another embodiment, the disclosure relates to a method for producing a wheat plant comprising crossing a first plant that has at least one non-transgenic mutation in a first EPSPS gene with a second plant that has at least one non-transgenic mutation in a second EPSPS gene; and selecting progeny plants that have at least one mutation in at least two copies of a EPSPS gene.

In another embodiment, the disclosure relates to a method for producing a plant comprising crossing a first plant that has at least one non-transgenic mutation in a first and second EPSPS gene with a second plant that has at least one non-transgenic mutation in a third EPSPS gene; and selecting progeny plants that have at least one mutation in all three copies of a EPSPS gene. In this embodiment, there would be at least one mutation in the EPSPS gene of the A, B, and D genomes.

VII. Wheat Plant, Wheat Seed and Parts of Wheat Plant

In one embodiment, a wheat plant with resistance to glyphosate is produced according to the methods disclosed herein. In yet another embodiment, a wheat plant with resistance to glyphosate and unaltered growth characteristics as compared to a wild type wheat plant is produced according to the methods disclosed herein. In yet another embodiment, a wheat plant with resistance to glyphosate and wild type germination rates is disclosed herein.

In yet another embodiment, a wheat plant with resistance to glyphosate that produces seed that germinates is disclosed herein. In yet another embodiment, a wheat plant with resistance to glyphosate and wild type fertility is disclosed herein.

In yet another embodiment, a wheat plant with resistance to glyphosate and normal yields is disclosed herein.

In one embodiment, wheat plants or parts thereof are tolerant to an application rate of 34.4 g or more, or 68.8 g or more, of the isopropylamine salt of glyphosate per hectare in the field.

In another embodiment, the wheat plant, wheat seed or parts of a wheat plant have one or more mutations in a EPSPS gene or a modified EPSPS gene. In another embodiment, the wheat plant, wheat seed or parts of a wheat plant have one or more mutations in EPSPS genes.

In another embodiment, the disclosure relates to a wheat plant, wheat seed or parts of a wheat plant comprising one or more non-transgenic mutations in the EPSPS gene. In another embodiment, the disclosure relates to a wheat plant, wheat seed or parts of a wheat plant comprising at least one non-transgenic mutation in the EPSPS gene in each of two genomes. In still another embodiment, the disclosure relates to a wheat plant, wheat seed or parts of a wheat plant comprising at least one non-transgenic mutation in the EPSPS gene in each of three genomes.

In one embodiment, the wheat plant, wheat seed or parts of a wheat plant comprises one or more non-transgenic mutations in both alleles of the EPSPS gene in the A genome. In another embodiment, the non-transgenic mutations are identical in both alleles of the EPSPS gene of the A genome.

In one embodiment, the wheat plant, wheat seed or parts of a wheat plant comprises one or more non-transgenic mutations in both alleles of the EPSPS gene in the B genome. In another embodiment, the non-transgenic mutations are identical in both alleles of the EPSPS gene of the B genome.

In one embodiment, the wheat plant, wheat seed or parts of a wheat plant comprises one or more non-transgenic mutations in both alleles of the EPSPS gene in the D genome. In another embodiment, the non-transgenic mutations are identical in both alleles of the EPSPS gene of the D genome.

In another embodiment, the wheat plant, wheat seed or parts of the wheat plant comprise a polynucleotide that codes for a polypeptide with one or more non-transgenic mutations listed in Table 4, wherein the polynucleotide has 85%, 86%, 87%, 88%, 89%, 90%, 91%, 92%, 93%, 94%, 95%, 96%, 97%, 98%, 99% or greater than 99% identity or similarity to SEQ ID NO: 6.

In still another embodiment, the wheat plant, wheat seed or parts of a wheat plant comprise a polynucleotide that codes for a polypeptide with one or more non-transgenic mutations listed in Table 4, wherein the polypeptide comprises one or more non-transgenic mutations and has 85%, 86%, 87%, 88%, 89%, 90%, 91%, 92%, 93%, 94%, 95%, 96%, 97%, 98%, 99% or greater than 99% identity or similarity to the EPSPS-A protein.

In another embodiment, the wheat plant, wheat seed or parts of the wheat plant comprise a polynucleotide having one or more mutations that codes for a polypeptide with one or more non-transgenic mutations listed in Table 4, wherein the polynucleotide has 85%, 86%, 87%, 88%, 89%, 90%, 91%, 92%, 93%, 94%, 95%, 96%, 97%, 98%, 99% or greater than 99% identity or similarity to SEQ ID NO: 7.

In still another embodiment, the wheat plant, wheat seed or parts of a wheat plant comprise a polynucleotide with one or more non-transgenic mutations that codes for a EPSPS protein, wherein the EPSPS protein comprises one or more non-transgenic mutations and has 85%, 86%, 87%, 88%, 89%, 90%, 91%, 92%, 93%, 94%, 95%, 96%, 97%, 98%, 99% or greater than 99% identity or similarity to the EPSPS-B protein.

In another embodiment, the wheat plant, wheat seed or parts of the wheat plant comprise a polynucleotide having one or more mutations that codes for a polypeptide with one or more non-transgenic mutations listed in Table 4, wherein the polynucleotide has 85%, 86%, 87%, 88%, 89%, 90%, 91%, 92%, 93%, 94%, 95%, 96%, 97%, 98%, 99% or greater than 99% identity or similarity to SEQ ID NO: 8.

In still another embodiment, the wheat plant, wheat seed or parts of a wheat plant comprise a polynucleotide with one or more non-transgenic mutations that codes for a EPSPS protein, wherein the EPSPS protein comprises one or more non-transgenic mutations and has 85%, 86%, 87%, 88%, 89%, 90%, 91%, 92%, 93%, 94%, 95%, 96%, 97%, 98%, 99% or greater than 99% identity or similarity to the EPSPS-D protein.

In another embodiment, the wheat plant, wheat seed or parts of a wheat plant has one or more mutations in the EPSPS gene that codes for a polypeptide having one or more mutations enumerated in Table 4 and corresponding mutations in the homoeologues. A wheat plant, wheat seed or parts of a wheat plant can be generated having 1, 2, 3, 4, 5, 6, 7, 8, 9, 10, 11, 12, 13, 14, 15, 16, 17, 18, 19, 20, 21, 22, 23, 24, 25 or greater than 25 of the mutations disclosed herein including but not limited to the mutations disclosed in Table 4, as well as mutations in corresponding homoeologues.

VIII. Grain, Flour and Starch

In another embodiment, the disclosure relates to a wheat grain, flour or starch comprising one or more non-transgenic mutations in the EPSPS gene or a modified EPSPS gene. In another embodiment, the disclosure relates to wheat grain comprising an embryo, wherein the embryo comprises one or more non-transgenic mutations in a EPSPS gene or a modified EPSPS gene.

In another embodiment, the wheat grain, flour or starch comprises one or more non-transgenic mutations in the EPSPS genes including but not limited to the mutations recited in Table 4 and the corresponding mutations in homologues, and homoeologues.

In still another embodiment, the disclosure relates to a wheat grain or flour comprising at least one non-transgenic mutation in the EPSPS gene in one, two, or three genomes.

In still another embodiment, the disclosure relates to a wheat grain, flour, or starch comprising one or more non-transgenic mutations in the EPSPS gene of the A genome. In another embodiment, the non-transgenic mutations are identical in both alleles of the EPSPS gene of the A genome.

In one embodiment, the wheat grain, flour, or starch comprises one or more non-transgenic mutations in both alleles of the EPSPS gene in the B genome. In another embodiment, the non-transgenic mutations are identical in both alleles of the EPSPS gene of the B genome.

In one embodiment, the wheat grain, flour or starch comprises one or more non-transgenic mutations in both alleles of the EPSPS gene in the D genome. In another embodiment, the non-transgenic mutations are identical in both alleles of the EPSPS gene of the D genome.

In one embodiment, the disclosure relates to wheat grain, wheat flour or starch comprising a polynucleotide of the EPSPS gene in the A genome corresponding to SEQ ID NO: 6 with one or more non-transgenic mutations that codes for a polypeptide having one or more mutations listed in Table 4. In another embodiment, the wheat grain or wheat flour comprise a polynucleotide with one or more non-transgenic mutations and has 85%, 86%, 87%, 88%, 89%, 90%, 91%, 92%, 93%, 94%, 95%, 96%, 97%, 98%, 99% or greater than 99% identity or similarity to SEQ ID NO: 6.

In still another embodiment, wheat grain, wheat flour or starch comprise a polynucleotide with one or more non-transgenic mutations that codes for a EPSPS protein having one or more mutations recited in Table 4, wherein the EPSPS protein has 85%, 86%, 87%, 88%, 89%, 90%, 91%, 92%, 93%, 94%, 95%, 96%, 97%, 98%, 99% or greater than 99% identity or similarity to the EPSPS-A protein.

In one embodiment, the disclosure relates to wheat grain, wheat flour or starch comprising a polynucleotide of the EPSPS gene in the B genome corresponding to SEQ ID NO: 7 with one or more mutations that codes for a polypeptide having one or more mutations recited in Table 4. In another embodiment, the wheat grain or wheat flour comprise a polynucleotide with one or more non-transgenic mutations and has 85%, 86%, 87%, 88%, 89%, 90%, 91%, 92%, 93%, 94%, 95%, 96%, 97%, 98%, 99% or greater than 99% identity or similarity to SEQ ID NO: 7

In still another embodiment, wheat grain, wheat flour or starch comprise a polynucleotide with one or more non-transgenic mutations that codes for a EPSPS protein having one or more mutations recited in Table 4, wherein the EPSPS protein has 85%, 86%, 87%, 88%, 89%, 90%, 91%, 92%, 93%, 94%, 95%, 96%, 97%, 98%, 99% or greater than 99% identity or similarity to EPSPS-B protein.

In one embodiment, the disclosure relates to wheat grain, wheat flour or starch comprising a polynucleotide of the EPSPS gene in the D genome corresponding to SEQ ID NO: 8 with one or more mutations that codes for a polypeptide having one or more mutations listed in Table 4. In another embodiment, the wheat grain or wheat flour comprise a polynucleotide with one or more mutations and has 85%, 86%, 87%, 88%, 89%, 90%, 91%, 92%, 93%, 94%, 95%, 96%, 97%, 98%, 99% or greater than 99% identity or similarity to SEQ ID NO: 8.

In still another embodiment, wheat grain, wheat flour or starch comprise a polynucleotide with one or more mutations that codes for a EPSPS protein having one or more mutations recited in Table 4, wherein the EPSPS protein has 85%, 86%, 87%, 88%, 89%, 90%, 91%, 92%, 93%, 94%, 95%, 96%, 97%, 98%, 99% or greater than 99% identity or similarity to EPSPS-D protein.

In still another embodiment, the disclosure relates to wheat grain or flour comprising an endosperm and a reduced gene expression level, activity or expression level and activity of the EPSPS gene as compared to wild type wheat grain or flour.

IX. Food Products

In one embodiment, the disclosure is directed to a flour or other product produced from the grain or flour discussed above. In another embodiment, the flour, the coarse fraction or purified starch may be a component of a food product.

The food product includes but is not limited to a bagel, a biscuit, a bread, a bun, a croissant, a dumpling, an English muffin, a muffin, a pita bread, a quickbread, a flat bread, a sourdough bread, a refrigerated/frozen dough product, dough, baked beans, a burrito, chili, a taco, a tamale, a tortilla, a pot pie, a ready to eat cereal, a ready to eat meal, stuffing, a microwaveable meal, a brownie, a cake, a cheesecake, a coffee cake, a cookie, a dessert, a pastry, a sweet roll, a candy bar, a pie crust, pie filling, baby food, a baking mix, a batter, a breading, a gravy mix, a meat extender, a meat substitute, a seasoning mix, a soup mix, a gravy, a roux, a salad dressing, a soup, sour cream, a noodle, a pasta, ramen noodles, chow mein noodles, lo mein noodles, an ice cream inclusion, an ice cream bar, an ice cream cone, an ice cream sandwich, a cracker, a crouton, a doughnut, an egg roll, an extruded snack, a fruit and grain bar, a microwaveable snack product, a nutritional bar, a pancake, a par-baked bakery product, a pretzel, a pudding, a granola-based product, a snack chip, a snack food, a snack mix, a waffle, a pizza crust, animal food or pet food.

In one embodiment, the flour is a whole grain flour (ex.—an ultrafine-milled whole grain flour, such as an ultrafine-milled whole grain wheat flour). In one embodiment, the whole grain flour includes a refined flour constituent (ex.—refined wheat flour or refined flour) and a coarse fraction (ex.—an ultrafine-milled coarse fraction). Refined wheat flour may be flour which is prepared, for example, by grinding and bolting (sifting) cleaned wheat. The Food and Drug Administration (FDA) requires flour to meet certain particle size standards in order to be included in the category of refined wheat flour. The particle size of refined wheat flour is described as flour in which not less than 98% passes through a cloth having openings not larger than those of woven wire cloth designated "212 micrometers (U.S. Wire 70)."

In another embodiment, the coarse fraction includes at least one of: bran and germ. For instance, the germ is an embryonic plant found within the wheat kernel. The germ includes lipids, fiber, vitamins, protein, minerals and phytonutrients, such as flavonoids. The bran may include several cell layers and has a significant amount of lipids, fiber, vitamins, protein, minerals and phytonutrients, such as flavonoids.

For example, the coarse fraction or whole grain flour or refined flour of the disclosure may be used in various amounts to replace refined or whole grain flour in baked goods, snack products, and food products. The whole grain flour (i.e.—ultrafine-milled whole grain flour) may also be marketed directly to consumers for use in their homemade baked products. In an exemplary embodiment, a granulation profile of the whole grain flour is such that 98% of particles by weight of the whole grain flour are less than 212 micrometers.

In another embodiment, the whole grain flour or coarse fraction or refined flour may be a component of a nutritional supplement. The nutritional supplement may be a product that is added to the diet containing one or more ingredients, typically including: vitamins, minerals, herbs, amino acids, enzymes, antioxidants, herbs, spices, probiotics, extracts, prebiotics and fiber.

In a further embodiment, the nutritional supplement may include any known nutritional ingredients that will aid in the overall health of an individual, examples include but are not limited to vitamins, minerals, other fiber components, fatty acids, antioxidants, amino acids, peptides, proteins, lutein, ribose, omega-3 fatty acids, and/or other nutritional ingredients. Because of the high nutritional content of the endosperm, there may be many uses that confer numerous benefits to an individual, including, delivery of fiber and other essential nutrients, increased digestive function and health, weight management, blood sugar management, heart health, diabetes risk reduction, potential arthritis risk reduction, and overall health and wellness for an individual.

In still another embodiments, the whole grain flour or coarse fraction or refined flour may be a component of a dietary supplement. The Code of Federal Regulations defines a dietary supplement as a product that is intended to supplement the diet and contains one or more dietary ingredients including: vitamins, minerals, herbs, botanicals, amino acids, and other substances or their constituents; is intended to be taken by mouth as a pill, capsule, tablet, or liquid; and is labeled on the front panel as being a dietary supplement.

In yet another embodiment, the whole grain flour or coarse fraction or refined flour may be a fiber supplement or a component thereof. The fiber supplement may be delivered in, but is not limited to the following forms: instant beverage mixes, ready-to-drink beverages, nutritional bars, wafers, cookies, crackers, gel shots, capsules, chews, chewable tablets, and pills. One embodiment delivers the fiber supplement in the form of a flavored shake or malt type beverage.

In another embodiment, the whole grain flour or coarse fraction or refined flour may be included as a component of a digestive supplement. The whole grain flour or coarse fraction or refined flour may be a component of a digestive supplement alone or in combination with one or more prebiotic compounds and/or probiotic organisms. Prebiotic compounds are non-digestible food ingredients that may beneficially affect the host by selectively stimulating the growth and/or the activity of a limited number of microorganisms in the colon. Examples of prebiotic compounds within the scope of the disclosure, may include, but are not limited to: oligosaccharides and inulins.

Probiotics are microorganisms which, when administered in adequate amounts, confer a health benefit on the host.

Probiotic organisms include, but are not limited to: *Lactobacillus*, *Bifidobacteria*, *Escherichia*, *Clostridium*, *Lactococcus*, *Streptococcus*, *Enterococcus*, and *Saccharomyces*.

In yet another embodiment, the whole grain flour or coarse fraction or refined flour may be included as a component of a functional food. The Institute of Food Technologists defines functional foods as, foods and food components that provide a health benefit beyond basic nutrition. This includes conventional foods, fortified, enriched, or enhanced foods, and dietary supplements. The whole grain flour and coarse fraction or refined flour include numerous vitamins and minerals, have high oxygen radical absorption capacities, and are high in fiber, making them ideally suited for use in/as a functional food.

In another embodiment, the whole grain flour or coarse fraction or refined flour may be used in medical foods. Medical food is defined as a food that is formulated to be consumed or administered entirely under the supervision of a physician and which is intended for the specific dietary management of a disease or condition for which distinctive nutritional requirements, based on recognized scientific principles, are established by medical evaluation. The nutrient contents and antioxidant capacities of the whole grain flour and coarse fraction or refined flour make them ideal for use in medical foods.

In yet another embodiment, the whole grain flour or coarse fraction or refined flour may also be used in pharmaceuticals. The whole grain flour and coarse fraction or refined flour are high in fiber and have a very fine granulation making them suitable for use as a carrier in pharmaceuticals.

In still another embodiment, delivery of the whole grain flour or coarse fraction or refined flour as a nutritional supplement, dietary supplement or digestive supplement is contemplated via delivery mechanisms where the whole grain flour or coarse fraction is the single ingredient or one of many nutritional ingredients. Examples of delivery mechanisms include but are not limited to: instant beverage mixes, ready-to-drink beverages, nutritional bars, wafers, cookies, crackers, gel shots, capsules, and chews.

In yet another embodiment, a milling process may be used to make a multi-wheat flour, or a multi-grain coarse fraction. In one embodiment, bran and germ from one type of wheat may be ground and blended with ground endosperm or whole grain wheat flour of another type of wheat. Alternatively bran and germ of one type of grain may be ground and blended with ground endosperm or whole grain flour of another type of grain.

In still another embodiment, bran and germ from a first type of wheat or grain may be blended with bran and germ from a second type of wheat or grain to produce a multi-grain coarse fraction. It is contemplated that the disclosure encompasses mixing any combination of one or more of bran, germ, endosperm, and whole grain flour of one or more grains. This multi-grain, multi-wheat approach may be used to make custom flour and capitalize on the qualities and nutritional contents of multiple types of grains or wheats to make one flour.

The whole grain flour disclosed herein may be produced via a variety of milling processes. One exemplary process involves grinding grain in a single stream without separating endosperm, bran, and germ of the grain into separate streams. Clean and tempered grain is conveyed to a first passage grinder, such as a hammermill, roller mill, pin mill, impact mill, disc mill, air attrition mill, gap mill, or the like. After grinding, the grain is discharged and conveyed to a sifter. Any sifter known in the art for sifting a ground particle may be used. Material passing through the screen of the sifter is the whole grain flour of the disclosure and requires no further processing. Material that remains on the screen is referred to as a second fraction. The second fraction requires additional particle reduction. Thus, this second fraction may be conveyed to a second passage grinder.

After grinding, the second fraction may be conveyed to a second sifter. Material passing through the screen of the second sifter is the whole grain flour. The material that remains on the screen is referred to as the fourth fraction and requires further processing to reduce the particle size. The fourth fraction on the screen of the second sifter is conveyed back into either the first passage grinder or the second passage grinder for further processing via a feedback loop.

It is contemplated that the whole grain flour, coarse fraction, purified starch and/or grain products of the disclosure may be produced by a number of milling processes known in the art.

X. Plant Breeding

In another embodiment, the disclosure is directed to methods for plant breeding using wheat plants and plant parts with one or more non-transgenic mutations in the EPSPS gene.

One such embodiment is the method of crossing a wheat variety with one or more non-transgenic mutations in the EPSPS gene with another variety of wheat to form a first generation population of F1 plants. The population of first generation F1 plants produced by this method is also an embodiment of the disclosure. This first generation population of F1 plants will comprise an essentially complete set of the alleles of a wheat variety with one or more non-transgenic mutations in the EPSPS gene. One of ordinary skill in the art can utilize either breeder books or molecular methods to identify a particular F1 plant produced using a wheat variety with one or more non-transgenic mutations in the EPSPS gene, and any such individual plant is also encompassed by this disclosure. These embodiments also cover use of transgenic or backcross conversions of wheat varieties with one or more mutations in the EPSPS gene to produce first generation F1 plants.

In another embodiment, the disclosure relates to a method of developing a progeny wheat plant. A method of developing a progeny wheat plant comprises crossing a wheat variety with one or more non-transgenic mutations in the EPSPS gene with a second wheat plant and performing a breeding method. A specific method for producing a line derived from a wheat variety with one or more non-transgenic mutations in the EPSPS gene is as follows.

One of ordinary skill in the art would cross a wheat variety with one or more non-transgenic mutations in the EPSPS gene with another variety of wheat, such as an elite variety. The F1 seed derived from this cross would be grown to form a homogeneous population. The F1 seed would contain one set of the alleles from a wheat variety with one or more non-transgenic mutations in the EPSPS gene and one set of the alleles from the other wheat variety.

The F1 genome would be made-up of 50% of a wheat variety with one or more non-transgenic mutations in the EPSPS gene and 50% of the other elite variety. The F1 seed would be grown to form F2 seed. The F1 seed could be allowed to self, or bred with another wheat cultivar.

On average the F2 seed would have derived 50% of its alleles from a wheat variety with one or more non-transgenic mutations in the EPSPS gene and 50% from the other wheat variety, but various individual plants from the population would have a much greater percentage of their alleles derived from a wheat variety with one or more non-transgenic mutations in the EPSPS gene (Wang J. and R. Bernardo, 2000, Crop Sci. 40:659-665 and Bernardo, R. and A. L. Kahler, 2001, Theor. Appl. Genet. 102:986-992).

The F2 seed would be grown and selection of plants would be made based on visual observation and/or measurement of traits and/or marker assisted selection. The wheat variety with one or more non-transgenic mutations in the EPSPS gene-derived progeny that exhibit gene-derived traits would be selected and each plant would be harvested separately. This F3 seed from each plant would be grown in individual rows and allowed to self. Then selected rows or plants from the rows would be harvested and threshed individually. The selections would again be based on visual observation and/or measurements for desirable traits of the plants, such as one or more of the desirable wheat variety with one or more non-transgenic mutations in the EPSPS gene-derived traits.

The process of growing and selection would be repeated any number of times until a homozygous wheat variety with one or more non-transgenic mutations in the EPSPS gene-derived wheat plant is obtained. The homozygous wheat variety with one or more non-transgenic mutations in the EPSPS gene-derived wheat plant would contain desirable traits derived from the wheat variety with one or more non-transgenic mutations in the EPSPS gene, some of which may not have been expressed by the other original wheat variety to which the wheat variety with one or more non-transgenic mutations in the EPSPS gene was crossed and some of which may have been expressed by both wheat varieties but now would be at a level equal to or greater than the level expressed in the wheat variety with one or more non-transgenic mutations in the EPSPS gene.

The breeding process, of crossing, selfing, and selection may be repeated to produce another population of wheat variety with one or more non-transgenic mutations in the EPSPS gene-derived wheat plants with, on average, 25% of their genes derived from wheat variety with one or more non-transgenic mutations in the EPSPS gene, but various individual plants from the population would have a much greater percentage of their alleles derived from the wheat variety with one or more non-transgenic mutations in the EPSPS gene. Another embodiment of the disclosure is a homozygous wheat variety with one or more non-transgenic mutations in the EPSPS gene-derived wheat plant that has been crossed with another wheat plant with one or more non-transgenic mutations in the EPSPS gene-derived traits.

A. Mutations as Markers

Genetic markers are the biological features that are determined by allelic forms of genes or genetic loci and can be transmitted from one generation to another, and thus they can be used as experimental probes or tags to keep track of an individual, a plant, a tissue, a cell, a nucleus, a chromosome or a gene. Genetic markers used in genetics and plant breeding can be classified into two categories: classical markers and DNA markers. Classical markers include morphological markers, cytological markers and biochemical markers. DNA markers have developed into many systems based on different polymorphism-detecting techniques or methods (southern blotting-nuclear acid hybridization, PCR-polymerase chain reaction, and DNA sequencing), such as restriction fragment length polymorphism (RFLP), amplified fragment length polymorphism (AFLP), random amplified polymorphic DNA (RAPD), simple sequence repeat (SSR), single nucleotide polymorphism (SNP), etc.

SNPs provide the ultimate/simplest form of molecular markers as a single nucleotide base is the smallest unit of inheritance, and thus they can provide the maximum number of markers. SNPs occur very commonly in animals and plants. Typically, SNP frequencies are in a range of one SNP every 100-300 base pairs in plants. SNPs may be present within coding sequences of genes, non-coding regions of genes or in the intergenic regions between genes at different frequencies in different chromosome regions.

SNPs are co-dominant markers, often linked to genes and present in the simplest/ultimate form for polymorphism, and thus they have become very attractive and potential genetic markers in genetic study and breeding. Moreover, SNPs can be very easily automated and quickly detected, with a high efficiency for detection of polymorphisms.

In one embodiment, the disclosure relates to mutations in the EPSPS gene, which are single nucleotide polymorphisms, that can be used as markers in plant breeding. The mutations in the EPSPS gene are causative and their segregation can be followed using, for example, KASP probes.

In another embodiment, mutations identified in Section II of this disclosure can be used as markers in plant breeding. In yet another embodiment, one or more mutations in Tables 1-3 can be used as markers in plant breeding.

In one embodiment, the mutations can be followed using techniques including but not limited to SNP-Restriction Fragment Length Polymorphism (RFLP); CAPS; Axiom SNP Arrays; iSelect Array; TaqMan Probes, and KASP Probes. In another embodiment, Next Generation Sequencing techniques can be used including but not limited to 454 Life Sciences (Roche Applied Science, Indianapolis, Ind.); HiSeq (Illumina, San Diego, Calif.); SOLiD and Ion Torrent (Life Technologies Corporation, Carlsbad, Calif.).

PCR-based KASP™ genotyping assay is a homogeneous, fluorescence (FRET) based assay that enables accurate bi-allelic discrimination of known SNPs and InDels. A key feature of PCR-based KASP technology is the use of a universal FRET cassette reporter system that eliminates the need for costly dual-labelled probes. The allele-specific forward primers each have a proprietary tail sequence that corresponds with one of two FRET cassettes: one label with FAM dye and the other with HEX dye. Bi-allelic discrimination is achieved through the competitive binding of the two allele-specific forward primers.

The plants, compositions and methods are further described by the following non-limiting paragraphs:

1. A wheat plant comprising a mutation in a EPSPS gene in at least one of the A, B, or D genomes, wherein the mutation contributes to a wheat plant having resistance to glyphosate as compared to a wild type plant.

2. A wheat plant comprising a mutation in an EPSPS gene in at least one of the A, B, or D genomes, wherein the gene mutation produces an EPSPS protein with a mutation in the active region, and further wherein the mutation contributes to wheat plant having resistance to glyphosate as compared to a wild type plant.

3. A wheat plant comprising a mutation in a EPSPS gene in at least one of the A, B, or D genomes, wherein the gene mutation produces an EPSPS protein with reduced affinity for glyphosate and similar affinity as wild type for plant substrates, and further wherein the mutation contributes to a wheat plant having resistance to glyphosate as compared to a wild type plant 4. The wheat plant of any of paragraphs 1-3, wherein the mutation in the EPSPS gene is in the B and D genomes.

5. The wheat plant of any of paragraphs 1-3, wherein the mutation in the EPSPS gene is in the A and B genomes.

6. The wheat plant of any of paragraphs 1-3, wherein the mutation in the EPSPS gene is in the A and D genomes.

7. The wheat plant of any of paragraphs 1-3, wherein the mutation in the EPSPS gene is in the A, B, and D genomes.

8. The wheat plant of any of the preceding paragraphs, wherein the mutation results in an EPSPS protein with reduced affinity for glyphosate.

9. The wheat plant of any of the preceding paragraphs, wherein the mutation results in an EPSPS protein with similar affinity as wild type for plant substrates.

10. The wheat plant of any of the preceding paragraphs, wherein the mutation results in an EPSPS protein with reduced affinity for glyphosate and similar affinity as wild type for
plant substrates.

11. The wheat plant of any of the preceding paragraphs, wherein the mutation results in an EPSPS protein with affinity for glyphosate selected from the group consisting of: about 10%, 20%, 30%, 40%, 50%, 60%, 70%, 80, or 90% of the affinity of wild type EPSPS for glyphosate.

12. The wheat plant of any of the preceding paragraphs, wherein said wheat plant is homozygous for the mutation.

13. The wheat plant of any of the preceding paragraphs, which is *Triticum aestivum* ssp. *aestivum*.

14. The wheat plant of any of the preceding paragraphs, which is *Triticum turgidum* subsp. *Durum*.

15. The wheat plant of any of the preceding paragraphs, wherein the mutation is recited in Tables 1-3.

16. Wheat grain from the wheat plant of any of the preceding paragraphs.

17. Flour comprising the wheat grain of any of the preceding paragraphs.

18. A food product comprising a component of the wheat plant of any of the preceding paragraphs.

19. A wheat seed, plant part or progeny thereof from the wheat plant of any of the preceding paragraphs.

20. A transgenic wheat plant comprising a transgene that reduces expression of a EPSPS gene and/or reduces affinity of an EPSPS protein for glyphosate, wherein the reduced expression and/or reduced affinity for glyphosate contributes to a wheat plant having resistance teglyphosate.

21. The wheat plant of paragraph 20, wherein the transgene results an EPSPS protein with similar affinity as wild type for plant substrates.

22. The wheat plant of paragraph 20, wherein the transgene results in an EPSPS protein with a mutation in the active region of the protein.

23. The wheat plant of paragraph 20, wherein the transgene results in an EPSPS protein with reduced affinity for glyphosate and similar affinity as wild type EPSPS for plant substrates.

24. The wheat plant of paragraph 20, wherein the transgene results in an EPSPS protein with affinity for glyphosate selected from the group consisting of: about 10%, 20%, 30%, 40%, 50%, 60%, 70%, 80, or 90% of the affinity of wild type EPSPS for glyphosate.

25. The wheat plant of paragraph 20, which is *Triticum aestivum* ssp. *aestivum*.

26. The wheat plant of paragraph 20, which is *Triticum turgidum* subsp. *Durum*.

27. Wheat grain from the wheat plant of any of paragraphs 20-26.

28. Flour comprising the wheat grain of paragraph 27.

29. A food product comprising a component of the wheat plant of paragraphs 20-28.

30. A wheat seed, plant part or progeny thereof from the wheat plant of paragraphs 20-26.

31. A wheat plant comprising a modified EPSPS gene, wherein the EPSPS gene was modified by genomic editing, and said modification contributes to said wheat plant having resistance to glyphosate.

32. The wheat plant of paragraph 31, wherein the modified EPSPS gene results an EPSPS protein with wild type affinity for plant substrates.

33. The wheat plant of paragraph 31, wherein the modified EPSPS gene results in an EPSPS protein with a mutation in the active region of the protein.

34. The wheat plant of paragraph 31, wherein the modified EPSPS gene results in an EPSPS protein with reduced affinity for glyphosate and similar affinity as wild type for plant vsubstrates.

35. The wheat plant of paragraph 31, wherein the modified EPSPS gene results in an EPSPS protein with affinity for glyphosate selected from the group consisting of: about 10%, 20%, 30%, 40%, 50%, 60%, 70%, 80, or 90% of the affinity of wild type EPSPS for glyphosate.

36. The wheat plant of paragraph 31, which is *Triticum aestivum* ssp. *aestivum*.

37. The wheat plant of paragraph 31, which is *Triticum turgidum* subsp. *Durum*.

38. Wheat grain from the wheat plant of any of paragraphs 31-37.

39. Flour comprising the wheat grain of paragraph 38.

40. A food product comprising a component of the wheat plant of paragraphs 31-39.

41. A wheat seed, plant part or progeny thereof from the wheat plant of paragraphs 31-37.

42. A method of creating a wheat plant that is resistant to the herbicide glyphosate compared to wild type wheat plants, comprising the steps of:
   a. obtaining plant material from a parent wheat plant;
   b. inducing at least one mutation in at least one copy of an EPSPS gene of the plant material by treating the plant material with a mutagen to create mutagenized plant material;
   c. culturing the mutagenized plant material to produce progeny wheat plants;
   d. analyzing progeny wheat plants to detect at least one mutation in at least one copy of an EPSPS gene;
   e. selecting progeny wheat plants that are resistant to the herbicide glyphosate compared to the parent wheat plant; and
   f. repeating the cycle of culturing the progeny wheat plants to produce additional progeny wheat plants that are resistant to glyphosate.

43. The method of paragraph 42 wherein the plant material is selected from the group consisting of seeds, pollen, plant cells, or plant tissue.

44. The method of paragraph 42 wherein the mutagen is ethyl methanesulfonate.

45. The method of paragraph 44 wherein the concentration of ethyl methanesulfonate used is from 0.75% to about 1.2%.

46. The method of paragraph 42 where the progeny wheat plant are analyzed by a. isolating genomic DNA from the progeny wheat plants; and
   b. amplifying segments of an EPSPS gene in the isolated genomic DNA using primers specific to the EPSPS gene or to the DNA sequences adjacent to the EPSPS gene.

47. The method of any of the preceding paragraphs wherein the EPSPS gene sequence is substantially identical to SEQ. I.D. No.: 6.

48. The method of any of the preceding paragraphs wherein the EPSPS gene sequence is substantially identical to SEQ. I.D. No.: 7.

49. The method of any of the preceding paragraphs wherein the EPSPS gene sequence is substantially identical to SEQ. I.D. No.: 8.

50. The method of any of the preceding paragraphs where at least one primer has a sequence substantially identical to a sequence in the group consisting of SEQ. ID. NOs. 9 through 12.

51. The method of any of the preceding paragraphs wherein the mutation detected in step d is evaluated to determine the mutation's likelihood of increasing resistance to glyphosate 52. The method of any of the preceding paragraphs where in the mutation is evaluated using a bioinformatics tool selected from the group consisting of SIFT, PSSM and PARSESNP.

53. A wheat plant created according to a method of any of the preceding paragraphs 54. Flower, seeds, pollen, plant parts or progeny of the wheat plant of paragraph 53.

55. Parts of the seeds of paragraph 54.

56. Food and food products incorporating any portion of the seed of the wheat plant of paragraph 53.

57. A wheat plant exhibiting resistance to glyphosate created by breeding a wheat plant with the wheat plant of paragraph 53.

58. An endogenous EPSPS gene having substantial identity to SEQ. I.D. No. 6 and having a non-transgenic mutation within the endogenous EPSPS gene following treatment with a mutagen.

59. The endogenous EPSPS gene of paragraph 58 wherein the non-transgenic mutation is a missense mutation.

60. The non-transgenic missense mutation of paragraph 59 wherein the mutation is a T168I of SEQ ID NO. 9.

61. The non-transgenic missense mutation of paragraph 59 wherein the mutation is a P172S of SEQ ID NO. 9.

62. A wheat plant containing the endogenous EPSPS gene of any of the preceding paragraphs.

63. Flowers, seeds, pollen, plant parts, and progeny of the wheat plant of any of the preceding paragraphs.

64. Parts of the seeds of any of the preceding paragraphs.

65. Food and food products incorporating any portion of the seeds of the wheat plant of any of the preceding paragraphs.

66. An endogenous EPSPS gene having substantial identity to SEQ. I.D. No. 7 and having a non-transgenic mutation within the endogenous EPSPS gene following treatment with a mutagen.

67. The endogenous EPSPS gene of paragraph 66 wherein the non-transgenic mutation is a missense mutation.

68. The non-transgenic missense mutation of paragraph 67 wherein the mutation is a T168I of SEQ ID NO. 9.

69. The non-transgenic missense mutation of paragraph 67 wherein the mutation is a P172S of SEQ ID NO. 9.

70. A wheat plant containing the endogenous EPSPS gene of paragraph 66.

71. Flowers, seeds, pollen, plant parts, and progeny of the EPSPS plant of any of the preceding paragraphs.

72. Parts of the seeds of any of the preceding paragraphs.

73. Food and food products incorporating any portion of the seeds of the wheat plant of any of the preceding paragraphs.

74. An endogenous EPSPS gene having substantial identity to SEQ. I.D. No. 8 and having a non-transgenic mutation within the endogenous EPSPS gene following treatment with a mutagen.

75. The endogenous EPSPS gene of paragraph 74 wherein the non-transgenic mutation is a missense mutation.

76. The non-transgenic missense mutation of paragraph 75 wherein the mutation is a threonine to isoleucine at position 173 (T173I) of SEQ ID NO. 3 or T168I of SEQ ID NO. 9.

77. The non-transgenic missense mutation of claim 75 wherein the mutation is a proline to serine at position 177 of SEQ ID NO. 3 (P177S) or P172S of SEQ ID NO. 9.

78. A wheat plant containing the endogenous EPSPS gene of paragraph 74.

79. Flowers, seeds, pollen, plant parts, and progeny of the EPSPS plant of any of the preceding paragraphs.

80. Parts of the seeds of any of the preceding paragraphs.

81. Food and food products incorporating any portion of the seeds of the wheat plant
of any of the preceding paragraphs.

82. A wheat plant containing two or more of the endogenous EPSPS genes selected from the endogenous EPSPS genes of any of the preceding paragraphs.

83. A wheat plant comprising a mutation in an EPSPS gene of at least two of the A, B, and D genomes, wherein the EPSPS gene of the A genome encodes an EPSPS polypeptide comprising a proline to serine mutation at amino acid position 172 of SEQ ID NO. 9 (P177S of SEQ ID NO. 3).

84. A wheat plant comprising at least two mutations in an EPSPS gene of the A genome, wherein the mutated EPSPS gene of the A genome encodes an EPSPS polypeptide comprising a threonine to isoleucine change at amino acid position 168 (T168I) and a proline to serine change at amino acid position 172 (P172S) of SEQ ID NO. 9 (T173I and P177S of SEQ ID NO. 3).

85. A wheat plant comprising at least two mutations in an EPSPS gene of the D genome, wherein the mutated EPSPS gene of the D genome encodes an EPSPS polypeptide comprising a threonine to isoleucine change at amino acid position 168 (T168I) and a proline to serine change at amino acid position 172 (P172S) of SEQ ID NO. 9 (T173I and P177S of SEQ ID NO. 3).

86. A wheat plant comprising a mutation in an EPSPS gene of at least two of the A, B, and D genomes, wherein the EPSPS gene of the A genome has at least two mutations and encodes an EPSPS polypeptide comprising a threonine to isoleucine change at amino acid position 168 (T168I) and a proline to serine change at amino acid position 172 (P172S) of SEQ ID NO. 9 (T173I and P177S of SEQ ID NO. 3).

87. A wheat plant comprising a mutation in an EPSPS gene of at least two of the A, B, and D genomes, wherein the EPSPS gene of the A genome has at least two mutations and encodes an EPSPS polypeptide comprising a threonine to isoleucine change at amino acid position 168 (T168I) and a proline to serine change at amino acid position 172 (P172S) of SEQ ID NO. 9, and wherein the EPSPS gene of the D genome has at least two mutations and encodes an EPSPS polypeptide comprising a threonine to isoleucine change at amino acid position 168 (T168I) and a proline to serine change at amino acid position 172 (P172S) of SEQ ID NO. 9.

88. A wheat plant comprising a mutation in an EPSPS gene in each of the A, B, and D genomes, wherein the EPSPS gene of the A genome has at least two mutations and encodes an EPSPS polypeptide comprising a threonine to isoleucine change at amino acid position 168 (T168I) and a proline to serine change at amino acid position 172 (P172S) of SEQ ID NO. 9, and wherein the EPSPS gene of the D genome has at least two mutations and encodes an EPSPS polypeptide comprising a threonine to isoleucine change at amino acid position 168 (T168I) and a proline to serine change at amino acid position 172 (P172S) of SEQ ID NO. 9, and wherein the EPSPS gene of the B genome has a mutation and encodes an EPSPS polypeptide comprising a threonine to isoleucine change at amino acid position 168 of SEQ ID NO. 9.

89. A wheat plant comprising a mutation in an EPSPS gene in each of the A, B, and D genomes, wherein the EPSPS gene of the A genome has at least two mutations and encodes an EPSPS polypeptide comprising a threonine to isoleucine change at amino acid position 168 (T168I) and a proline to serine change at amino acid position 172 (P172S) of SEQ ID NO. 9, and wherein the EPSPS gene of the D genome has at least one mutation and encodes an EPSPS polypeptide comprising a threonine to isoleucine change at amino acid position 168 (T168I) and/or a proline to serine change at amino acid position 172 (P172S) of SEQ ID NO. 9, and wherein the EPSPS gene of the B genome has a mutation and encodes an EPSPS polypeptide comprising a threonine to isoleucine change at amino acid position 168 of SEQ ID NO. 9.

90. A wheat plant comprising a mutation in an EPSPS gene in each of the A, B, and D genomes, wherein the EPSPS gene of the A genome has at least one mutation and encodes an EPSPS polypeptide comprising a threonine to isoleucine change at amino acid position 168 (T168I) and/or a proline to serine change at amino acid position 172 (P172S) of SEQ ID NO. 9, and wherein the EPSPS gene of the D genome has at least two mutations and encodes an EPSPS polypeptide comprising a threonine to isoleucine change at amino acid position 168 (T168I) and a proline to serine change at amino acid position 172 (P172S) of SEQ ID NO. 9, and wherein the EPSPS gene of the B genome has a mutation and encodes an EPSPS polypeptide comprising a threonine to isoleucine change at amino acid position 168 of SEQ ID NO. 9.

91. A wheat plant comprising a mutation in an EPSPS gene of at least two of the A, B, and D genomes, wherein the EPSPS gene of the A genome encodes an EPSPS polypeptide comprising a proline to serine at amino acid position 172 of SEQ ID NO. 9, and wherein the EPSPS gene of the D genome encodes an EPSPS polypeptide comprising a threonine to isoleucine at amino acid position 168 of SEQ ID NO. 9.

92. A wheat plant comprising a mutation in an EPSPS gene in each of the A, B, and D genomes, wherein the EPSPS gene of the A genome has at least two mutations, the EPSPS gene of the B genome has a least one mutation, and the EPSPS gene of the D genome has at least one mutation, wherein the wheat plant has increased resistance to glyphosate.

93. A wheat plant comprising a mutation in an EPSPS gene in each of the A, B, and D genomes, wherein the EPSPS gene of the A genome has at least one mutations, the EPSPS gene of the B genome has a least one mutation, and the EPSPS gene of the D genome has at least two mutations, wherein the wheat plant has increased resistance to glyphosate.

94. A wheat plant comprising a mutation in an EPSPS gene in each of the A, B, and D genomes, wherein the EPSPS gene of the A genome has at least one mutation and encodes an EPSPS polypeptide comprising a threonine to isoleucine change at amino acid position 168 (T168I) and/or a proline to serine change at amino acid position 172 (P172S) of SEQ ID NO. 9, and wherein the EPSPS gene of the D genome has at least two mutations and encodes an EPSPS polypeptide comprising a threonine to isoleucine change at amino acid position 168 (T168I) and a proline to serine change at amino acid position 172 (P172S) of SEQ ID NO. 9, and wherein the EPSPS gene of the B genome has a mutation and encodes an EPSPS polypeptide comprising a proline to leucine change at amino acid position 172 of SEQ ID NO. 9.

95. The wheat plant of any of paragraphs 82-94, which is *Triticum aestivum* ssp. *aestivum*.

96. The wheat plant of any of paragraphs 82-94, which is *Triticum turgidum* subsp. *Durum*.

97. Wheat grain from the wheat plant of any of paragraphs 82-94.

98. Flour comprising the wheat grain of paragraph 97.

99. A food product comprising a component of the wheat plant of paragraphs 82-94

100. A wheat seed, plant part or progeny thereof from the wheat plant of paragraphs 82-94.

101. A wheat plant of any of the preceding paragraphs, wherein the wheat plant has resistance to glyphosate.

102. A wheat plant of any of the preceding paragraphs, wherein the wheat plant has resistance to glyphosate and unaltered growth characteristics.

103. A wheat plant of any of the preceding paragraphs, wherein the EPSPS protein has reduced affinity for glyphosate and substantial affinity for plant or endogenous substrates.

The following Examples are offered by way of illustration only, and not limitation. It is to be understood that the mutations discussed herein are merely exemplary and that similar mutations are also contemplated.

EXAMPLES

Example 1

A. Mutagenesis

Wheat seeds of the hexaploid cultivar Express (*Triticum aestivum*, PVP #9000012) were vacuum infiltrated in $H_2O$ (approximately 1,000 seeds/100 ml $H_2O$ for approximately 4 minutes). The seeds were then placed on a shaker (45 rpm) in a fume hood at ambient temperature. The mutagen ethyl methanesulfonate (EMS) was added to the imbibing seeds to final concentrations ranging from about 0.75% to about 1.2% (v/v). Following an 18 hour incubation period, the EMS solution was replaced 4 times with fresh $H_2O$. The seeds were then rinsed under running water for about 4-8 hours. Finally, the mutagenized seeds were planted (96/tray) in potting soil and allowed to germinate indoors. Plants that were four to six weeks old were transferred to the field to grow to fully mature M1 plants. The mature M1 plants were allowed to self-pollinate and then seeds from the M1 plant were collected and planted to produce M2 plants.

B. DNA Preparation

DNA from these M2 plants produced in accordance with the above description was extracted and prepared in order to identify the M2 plants carried a mutation at an EPSPS locus. The M2 plant DNA was prepared using the methods and reagents contained in the Qiagen® (Valencia, Calif.) DNeasy® 96 Plant Kit. Approximately 50 mg of frozen plant sample was placed in a sample tube with a tungsten bead, frozen in liquid nitrogen and ground 2 times for 1 minute each at 20 Hz using the Retsch® Mixer Mill MM 300. Next, 400 µl of solution AP1 [Buffer AP1, solution DX and RNAse (100 mg/ml)] at 80° C. was added to the sample. The tube was sealed and shaken for 15 seconds. Following the addition of 130 µl Buffer AP2, the tube was shaken for 15 seconds. The samples were placed in a freezer at minus 20° C. for at least 1 hour. The samples were then centrifuged for 20 minutes at 5,600×g. A 400 µl aliquot of supernatant was transferred to another sample tube. Following the addition of 600 µl of Buffer AP3/E, this sample tube was capped and shaken for 15 seconds. A filter plate was placed on a square well block and 1 ml of the sample solution was applied to each well and the plate was sealed. The plate and block were centrifuged for 4 minutes at 5,600×g. Next, 800 µl of Buffer AW was added to each well of the filter plate. Plates were sealed and spun for 15 minutes at 5600×g in the square well block. The filter plate was then placed on a new set of sample tubes and 80 µl of Buffer AE was applied to the filter. It was capped and incubated at room temperature for 1 minute and then spun for 2 minutes at 5,600×g. This step was repeated with an additional 80 µl Buffer AE. The filter plate was removed and the tubes containing the pooled filtrates were capped. The individual samples were then normalized to a DNA concentration of 5 to 10 ng/µl.

C. TILLING®

The M2 DNA was pooled into groups of two individual plants. The DNA concentration for each individual within the pool was approximately 0.8 ng/µl with a final concentration of 1.6 ng./µl for the entire pool. Then, 5 µl of the pooled DNA samples (or 8 ng) was arrayed on microtiter plates and subjected to gene-specific PCR.

PCR amplification was performed in 15 µl volumes containing 2.5 ng pooled DNA, 0.75× ExTaq buffer (Panvera®, Madison, Wis.), 2.6 mM $MgCl_2$, 0.3 mM dNTPs, 0.3 µM primers, and 0.05 U Ex-Taq (Panvera) DNA polymerase. PCR amplification was performed using an MJ Research® thermal cycler as follows: 95° C. for 2 minutes; 8 cycles of "touchdown PCR" (94° C. for 20 second, followed by annealing step starting at 70-68° C. for 30 seconds and decreasing 1° C. per cycle, then a temperature ramp of 0.5° C. per second to 72° C. followed by 72° C. for 1 minute); 25-45 cycles of 94° C. for 20 seconds, 63-61° C. for 30 seconds, ramp 0.5° C./sec to 72° C., 72° C. for 1 minute; 72° C. for 8 minutes; 98° C. for 8 minutes; 80° C. for 20 seconds; 60 cycles of 80° C. for 7 seconds −0.3 degrees/cycle.

The PCR primers (MWG Biotech, Inc., High Point, N.C.) were mixed as follows:

2.5 µl 100 µM IRD-700 labeled left primer
7.5 µl 100 µM left primer
9.0 µl 100 µM IRD-800 labeled right primer
1.0 µl 100 µM right primer A label can be attached to each primer as described or to only one of the primers. Alternatively, Cy5.5 modified primers could be used. The label was coupled to the oligonucleotide using conventional phosphoramidite chemistry.

PCR products (15 µl) were digested in 96-well plates. Next, 30 µl of a solution containing 10 mM HEPES [4-(2-hydroxyethyl)-1-piperazineethanesulfonic acid] (pH 7.5), 10 mM $MgSO_4$, 0.002% (w/v) Triton® X-100, 20 ng/ml of bovine serum albumin, and CEL 1 (Transgenomic®, Inc.; 1:100,000 dilution) was added with mixing on ice, and the plate was incubated at 45° C. for 15 minutes. The specific activity of the CEL1 was 800 units/µl, where a unit was defined by the manufacturer as the amount of enzyme required to produce 1 ng of acid-soluble material from sheared, heat denatured calf thymus DNA at pH 8.5 in one minute at 37° C. Reactions were stopped by addition of 10 µl of a 2.5 M NaCl solution with 0.5 mg/ml blue dextran and 75 mM EDTA, followed by the addition of 80 µl isopropanol. The reactions were precipitated at 80° C., spun at 4,000 rpm for 30 minutes in an Eppendorf Centrifuge 5810. Pellets were resuspended in 8 µl of 33% formamide with 0.017% bromophenol blue dye, heated at 80° C. for 7 minutes and then at 95° C. for 2 minutes. Samples were transferred to a membrane comb using a comb-loading robot (MWG Biotech). The comb was inserted into a slab acrylamide gel (6.5%), electrophoresed for 10 minutes, and removed. Electrophoresis was continued for 4 hours at 1,500-V, 40-W, and 40-mA limits at 50° C.

During electrophoresis, the gel was imaged using a LICOR® (Lincoln, Nebr.) scanner which was set at a channel capable of detecting the IR Dye 700 and 800 labels. The gel image showed sequence-specific pattern of background bands common to all 96 lanes. Rare events, such as mutations, create new bands that stand out above the background pattern. Plants with bands indicative of mutations of interest were evaluated by TILLING® individual members of a pool mixed with wild type DNA and then sequencing individual PCR products. Plants carrying mutations confirmed by sequencing were grown up as described above (e.g., the M2 plant was backcrossed or outcrossed twice in order to eliminate background mutations and self-pollinated in order to create a plant that was homozygous for the mutation).

D. Identification and Evaluation of Mutation P177S in A Genome

DNA from a wheat plant originating from seeds of cultivar Express, which were incubated in 0.75% EMS, was amplified using primers TaEPS1CL and Ep486AR (SEQ ID NOs: 10 and 11). The PCR amplification products were then incubated with CEL 1 and electrophoresed. The electrophoresis gel image showed an IRD-700 labeled fragment at approximately 200 bp, which stood out above the background pattern for the full length PCR amplification product that was approximately 486 bp. Therefore, it was likely that this fragment contained a heteroduplex created by a mutation in the A homoeologue of the EPSPS gene sequence. Sequence analysis of this fragment showed the mutation was a cytosine to thymine change at nucleotide 1233 numbered according to the published genomic DNA for rice EPSPS (SEQ ID NO: 2). This mutation was associated with a change from proline to serine at amino acid number 177 (numbered according to the published rice EPSPS protein SEQ ID NO: 3) in the EPSPS polypeptide coded for by the A genome EPSPS homoeologue.

E. Identification and Evaluation of Mutation T173I in the B Genome

DNA from a wheat plant originating from seeds of cultivar Express that were incubated in 1.2% EMS, was amplified using primers TaEPS1CL and Ep558BR (SEQ ID NOs: 10 and 12). The PCR amplification products were then screened using a modification of the TaqMan® SNP Genotyping Assay (PN4332856C available from Applied Biosystems, Foster City, Calif.) with PCR primers (SEQ ID NOs: 14-15) and TaqMan® MGB probes (SEQ ID NOs: 16-17) to identify a cytosine to thymine change at nucleotide 1222 numbered according to the published genomic DNA for rice EPSPS (SEQ ID NO: 2). This mutation was associated with a change from threonine to isoleucine at amino acid number 173 (numbered according to the published rice EPSPS protein SEQ ID NO: 3) in the EPSPS polypeptide coded for by the B genome EPSPS homoeologue.

F. Identification and Evaluation of Mutation T173I in the D Genome

DNA from a wheat plant originating from seeds of cultivar Express that were incubated in 1.0% EMS, was amplified using primers TaEPS1CL and TaEPSJR (SEQ ID NOs: 10 and 13). The PCR amplification product were then incubated with CEL 1 and electrophoresed. The electrophoresis gel image showed an IRD_700 labeled fragment approximately 160 bp in length, which stood out above the background pattern for the full length PCR amplification product which was approximately 1,000 bps in length. Therefore, it was likely that this fragment contained a heteroduplex created by a mutation in the B homoeologue of the EPSPS gene sequence. Sequence analysis of this fragment showed the mutation was a cytosine to thymine change at nucleotide 1222 numbered according to the published genomic DNA for rice EPSPS (SEQ ID NO: 2). This mutation was associated with a change from threonine to isoleucine at amino acid number 173 (numbered according to the published rice EPSPS protein SEQ ID NO: 3) in the EPSPS polypeptide coded for by the D genome EPSPS homoeologue.

G. Phenotypic Analysis:

Wheat Plants Selected for Study:

Plants homozygous for the single preferred mutations (the T173I mutation in the B genome, the T173I mutation in the D genome and the P177S mutation in the A genome) were identified in the M3 seeds. Wild type siblings were also identified and used as controls. Plants that were homozygous for the T173I mutation in the D genome were crossed to plants that were homozygous for the P177S mutation in the A genome to generate double mutant plants.

Measurement of Resistance to Glyphosate:

Growth Chamber Studies: Seeds from plants that were homozygous for one of the single preferred mutations and seeds from their wild type sibling control plants were surface sterilized, placed on moist germination paper overnight, and then grown in glass tubes with 0.1× Murashige & Skoog (MS) medium containing 0 or 0.15 mM glyphosate. Germination was performed in a growth chamber under a light condition of 16 hours of light/8 hours of dark of 80 microEinsteins. At 10-14 days of development, shoot and root lengths were measured. On medium containing glyphosate, both shoot and root length were significantly greater for seeds that were homozygous for the preferred mutations than for wild type sibling control seeds indicating that the seeds with preferred mutations were resistant to glyphosate. Wild type seeds failed to thrive on medium containing glyphosate and most failed to grow whereas the majority of seeds with mutations grew well.

Seeds from plants that were homozygous for the double preferred mutations (both T173 I and P177S) were compared to seeds that were homozygous for each of the single preferred mutation for their ability to survive on MS media containing glyphosate. Seeds from their wild type sibling plants were used as positive controls. Seeds were germinated as described above. Measurements of shoot and root length indicated that seeds homozygous for the double preferred mutations were more resistant to glyphosate than seeds that were homozygous for each of the single preferred mutations. All three groups of seeds carrying mutations in one or more EPSPS genes (double T173I and P177S; single T173I; single P177S) were resistant to glyphosate and grew well compared to seeds from wild type sibling plants which for the most part failed to grow.

H. Re-Mutagenesis of Seeds of the Plant homozygous for A: P177S and D: 173I

In one embodiment, re-mutagenesis of seeds of plants homozygous for a mutation in the A genome or D genome can identify second-site mutations. Progeny seeds of the single site A and D genome plant were re-mutagenized and independent M2 mutants were identified that contained second-site mutations in EPSPS. A plant was identified that contains both the mutations P177S and T173I in the A genome. This combination was identified two independent times. Separately a plant was identified that contains the mutations P177S and T173I in the D genome. Crosses were made to incorporate both double mutants in the A and D genomes into a single plant. Separately, the B genome T173I mutation has been crossed to a plant containing the double mutations in the A and D genomes. In addition, separately, the B genome P177L (P172L) was crossed to a plant containing the double mutations in the A and D genomes.

The above examples are provided to illustrate the disclosure but not limit its scope. Other variants of the disclosure will be readily apparent to one of ordinary skill in the art and are encompassed by the appended claims and all their equivalents. The examples above used TILLING technology to create and identify mutations in one or more EPSPS genes of wheat but one of ordinary skill in the art would understand that other methods such as targeted mutagenesis (also known as site-directed mutagenesis, site-specific mutagenesis or oligonucleotide-directed mutagenesis) could be used to create the useful mutations in one or more EPSPS loci of wheat (see for example Zhang et al., PNAS 107(26):12028-12033, 2010; Saika et al., Plant Physiology 156:1269-1277, 2011). One of ordinary skill in the art would also recognize that additional methods could be used to inactivate or reduce the activity of the wheat EPSPS genes. These methods include without limitation CRISPR/Cas9 mutagenesis, TALEN and zinc finger mutagenesis, RNAi, micro RNA and hairpin RNA based methods to mutate or reduce the accumulation of the EPSPS transcripts. All publications, patents, and patent applications cited herein are hereby incorporated by reference.

Informational Sequence Listing

SEQ ID NO:1 shows the *Oryza sativa* EPSPS mRNA (NCBI Reference Sequence NM_001063247).

```
ORIGIN
     1  atggcggcga ccatggcgtc caacgccgcg gctgcggcgg cggtgtccct ggaccaggcc 61  gtggcggcgt cggcggcgtt ctcgtcgcgg aagcagctgc ggctgcccgc cgcggcgcgc 121  gggggatgc gggtgcgggt gcgggcgcgg gggcggcggg aggcggtggt ggtggcgtcc 181  gcgtcgtcgt cgtcggtggc agcgccggcg gcgaaggcgg aggagatcgt gctccagccc 241  atcagggaga tctccggggc ggttcagctg ccagggtcca agtcgctctc caacaggatc 301  ctcctcctct ccgccctctc cgagggcaca acagtggtgg acaacttgct gaacagtgag 361  gatgttcact acatgcttga ggccctgaaa gccctcgggc tctctgtgga agcagataaa
```

-continued

```
 421   gttgcaaaaa gagctgtagt cgttggctgt ggtggcaagt ttcctgttga aaggatgcg
 481   aaagaggaag tgcaactctt cttggggaac gctggaactg caatgcgacc attgacagca
 541   gccgtgactg ctgctggtgg aaatgcaact tatgtgcttg atggagtgcc acgaatgagg
 601   gagagaccga ttggtgactt ggttgtcggg ttgaaacaac ttggtgcgga tgtcgactgt
 661   ttccttggca ctgaatgccc acctgttcgt gtcaagggaa ttggaggact tcctggtggc
 721   aaggttaagc tctctggttc catcagcagt cagtacttga gtgccttgct gatggctgct
 781   cctttggccc ttggggatgt ggagatcgaa atcattgaca aactaatctc cattccttac
 841   gttgaaatga cattgagatt gatggagcgt tttggtgtga aggcagagca ttctgatagt
 901   tgggacagat tctatattaa gggagggcag aagtacaaat ctcctggaaa tgcctatgtt
 961   gaaggtgatg cctcaagcgc gagctatttc ttggctggtg ctgcaatcac tggaggcact
1021   gtgacagttc aaggttgtgg tacgaccagt ttgcagggtg atgtcaaatt tgctgaggta
1081   cttgagatga tgggagcaaa ggttacatgg actgacacca gtgtaaccgt aactggtcca
1141   ccacgtgagc cttatggaa gaaacacctg aaagctgttg atgtcaacat gaacaaaatg
1201   cctgatgttg ccatgaccct tgccgttgtt gcactcttcg ctgatggtcc aactgctatc
1261   agagatgtgg cttcctggag agtaaaggaa accgaaagga tggttgcaat tcggaccgag
1321   ctaacaaagc tgggagcatc ggttgaagaa ggtcctgact actgcatcat caccccaccg
1381   gagaagctga acatcacggc aatcgacacc tacgatgatc acaggatggc catggccttc
1441   tccctcgctg cctgcgccga cgtgcccgtg acgatcaggg accctggttg cacccgcaag
1501   accttcccca actacttcga cgttctaagc actttcgtca ggaactgaac tgagctttta
1561   aaagagtgag gtctaggttc tgttg
```

SEQ ID NO:2 shows the *Oryza sativa* EPSPS genomic DNA (NCBI Reference Sequence NC_008399).

```
ORIGIN
   1   atggcggcga ccatggcgtc caacgccgcg gctgcggcgg cggtgtccct ggaccaggcc
  61   gtggcggcgt cggcggcgtt ctcgtcgcgg aagcagctgc ggctgccccgc cgcggcgcgc
 121   gggggatgc gggtgcgggt gcgggcgcgg gggcggcggg aggcggtggt ggtggcgtcc
 181   gcgtcgtcgt cgtcggtggc agcgccggcg gcgaaggcgg aggagatcgt gctccagccc
 241   atcagggaga tctccggggc ggttcagctg ccagggtcca agtcgctctc caacaggatc
 301   ctcctcctct ccgccctctc cgaggtgaga cgcggatccc ttcctcttgc gtgaattcca
 361   tttctggaga tgagatttta gggggtttat taggtgaggt ggctgtgttt gtgaaatcct
 421   aggaattatc tctcaagtca atctaacgat gagatataac tgaggttctg gttttaatca
 481   cacactcata taaccaattt attgaaacat tttggtttgg cataagaaac tgcttacgaa
 541   ggtatgatat cctcctacat gtcaggctac taaattttca cgacggtatg atccactcaa
 601   aacaagtttc ttaacgagtc tggtgaggtc tgttatgaaa tttgtgtaaa ctaaggcaac
 661   tttggaggtt tcgcactgta ccaatgttat gtttgaacat tttgcaagca gtgctttctc
 721   ccaaaattat gcaattttga ggctcctcta catcattata attccccaat acattgctct
 781   ttattcttaa tagctttgat cgcgaaattt aacatttta ttcttgagct gttattttgt
 841   agcatcagtt tatcatgagc catgtttggt actaaatata caatcccttg gtttatttg
 901   tttccaagca tgtcattaac ttatcttaat gtggacaaga aactgatgcc tgcttacatt
 961   gctattattt caagcgggta ttgatccttt gacatgtgat tgatcatttt tttttctctg
```

```
1021  gttattaggg cacaacagtg gtggacaact tgctgaacag tgaggatgtt cactacatgc
1081  ttgaggccct gaaagccctc gggctctctg tggaagcaga taaagttgca aaaagagctg
1141  tagtcgttgg ctgtggtggc aagtttcctg ttgaaggga tgcgaaagag aagtgcaac
1201  tcttcttggg gaacgctgga aCtgcaatgc gaCcattgac agcagccgtg actgctgctg
1261  gtggaaatgc aacgtatgtt tttttttta atgtttatga aaatatgtat ggaattcatg
1321  gggtatgttt tatgaccttt ttctttacca tcagttatgt gcttgatgga gtgccacgaa
1381  tgagggagag accgattggt gacttggttg tcgggttgaa acaacttggt gcggatgtcg
1441  actgtttcct tggcactgaa tgcccacctg ttcgtgtcaa gggaattgga ggacttcctg
1501  gtggcaaggt tagttactcc taaactgcat cctttgtact tctgtatgca cctcaattct
1561  ttgtcaacct tctgcattta taaggaacat tctatgatgc aattcgacct tacactgcac
1621  agtaacttga aatgtttcat gcttaatcaa tatgccatat tcctgccaag ctcaagcgag
1681  caatatttgt ttgaatttgg taccatattt ttgtatattt gggcattcct ttttggtctt
1741  gatgtcttct tttgaattag catttaactg aattacactc aacaggttaa gctctctggt
1801  tccatcagca gtcagtactt gagtgccttg ctgatggctg ctcctttggc ccttggggat
1861  gtggagatcg aaatcattga caaactaatc tccattcctt acgttgaaat gacattgaga
1921  ttgatggagc gttttggtgt gaaggcagag cattctgata gttgggacag attctatatt
1981  aagggagggc agaagtacaa gtaagcttct acctgcctta ctgagctgaa ttattcgggt
2041  gtttatgatt aactccctaa actaaccctt tttcttttct ttggcattga cagatctcct
2101  ggaaatgcct atgttgaagg tgatgcctca agcgcgagct atttcttggc tggtgctgca
2161  atcactggag gcactgtgac agttcaaggt tgtggtacga ccagtttgca ggtataactg
2221  tagtgcctgt tttgacattc taccgtttag tcaagtttag tcagtagtca catattcaga
2281  atatagcaca atctgtatta tgccactgtt aatcaaatac gcttgaccta gagagtgcta
2341  tatccctag cttaatcttc aaactaaaca gttctcttgt ggcttgctgt gctgttatgt
2401  tccctgacct acatgttaat attacagggt gatgtcaaat ttgctgaggt acttgagatg
2461  atgggagcaa aggttacatg gactgacacc agtgtaaccg taactggtcc accacgtgag
2521  ccttatggga agaaacacct gaaagctgtt gatgtcaaca tgaacaaaat gcctgatgtt
2581  gccatgaccc ttgccgttgt tgcactcttc gctgatggtc caactgctat cagagatggt
2641  aaacattaag gcctattata cctgttctat catactagca attactgctt agcattgtga
2701  caaaacaaat aaccaaactt tcttcaaaat aacttagaaa tataagaaag gttcgttttg
2761  tgtggtaaac agtactactg tagtttcagc tatgaagttt gctgctggca attttctgaa
2821  cggtttcagc taaattgcat gtttgttcat catacttatc cattgtcttc cacagtggct
2881  tcctggagag taaaggaaac cgaaaggatg gttgcaattc ggaccgagct aacaaaggta
2941  aattcattag gtcccgtgtc ctttcattct tcaagtagtt tgttcataag ttgaattctc
3001  cttcaatgat gtttaaattc atcatcttct tttttggtgt tgtgccagct gggagcatcg
3061  gttgaagaag gtcctgacta ctgcatcatc accccaccgg agaagctgaa catcacggca
3121  atcgacacct acgatgatca caggatggcc atggccttct ccctcgctgc ctgcgccgac
3181  gtgcccgtga cgatcaggga ccctggttgc acccgcaaga ccttccccaa ctacttcgac
3241  gttctaagca cttttcgtcag gaactgaact gagctttaa aagagtgagg tctaggttct
3301  gttg
//
```

SEQ ID NO: 3 shows the EPSPS protein encoded by SEQ ID NO: 2 (NCBI Reference Sequence NP_001056712).

```
ORIGIN
   1 maatmasnaa aaaavsldqa vaasaafssr kqlrlpaaar ggmrvrvrar grreavvvas
  61 assssvaapa akaeeivlqp ireisgavql pgskslsnri lllsalsegt tvvdnllnse
 121 dvhymlealk alglsveadk vakravvvgc ggkfpvekda keevqlflgn agTamrPlta
 181 avtaaggnat yvldgvprmr erpigdlvvg lkqlgadvdc flgtecppvr vkgigglpgg
 241 kvklsgsiss qylsallmaa plalgdveie iidklisipy vemtlrlmer fgvkaehsds
 301 wdrfyikggq kykspgnayv egdassasyf lagaaitggt vtvqgcgtts lqgdvkfaev
 361 lemmgakvtw tdtsvtvtgp prepygkkhl kavdvnmnkm pdvamtlavv alfadgptai
 421 rdvaswrvke termvairte ltklgasvee gpdyciitpp eklnitaidt yddhrmamaf
 481 slaacadvpv tirdpgctrk tfpnyfdvls tfvrn
```

SEQ ID NOs: 4-5 show the DNA sequences for *Triticum aestivum* EPSPS-specific primers of used for genomic sequencing.

| SEQ ID | Primer Name | Primer ID | Primer Sequence |
|---|---|---|---|
| 4 | TaEPS1CL | 3155 | ACAGTGAGGATGTCCACTACATGCTTGA |
| 5 | TaEPS1ER | 3158 | AAATAGCTCGCACTTGAGGCATCACCTT |

SEQ ID NO: 6 shows the DNA sequence of a PCR product that comprises a partial genomic DNA sequence for EPSPS for the A genome of wheat.

GACCTTGGATCTCCGTGGaAGCAGATAAAGTTGCAAAAAGAGCTGTGGT

TGTTGGCTGTGGCGGCAGGTTCCCAGTCGAAAAGGACGCCAAAGAGGAA

GTAAAGCTCTTCTTGGGTAATGCTGGAACTGCAATGCGGCCACTGACGG

CAGCTGTAGTAGCTGCTGGTGGAAATGCAACGTATGTTTTCTTTATCCT

AGTGGAAATAAGTATGAGATCCATGGGTATGTTTGGAGACTGATCGTTT

CTTTTATTAAAAAAAAACTTCAGTTATGTGCTTGATGGCGTACCAAGAA

TGAGGGAGCGACCTATTGGTGACTTAGTTGTAGGTTTGCAACAACTCGG

CGCAGATGTCGATTGTTTCCTTGGCACAAACTGCCCACCTGTCCGTATC

AACGGCAAAGGAGGTCTACCTGGTGGCAAGGTTAGCTACTCATCAACTT

GCATGTTATCTACTTTGTGCACACTTCTGTTCTCTGTCAGAGAAGTTAT

TATTATGGCTAGTACGATGTAATGCAACCTTAGACCGCGCACTAAATTT

TAAGAACCAATCAACATTTAATAATTTCAATATGTGAGTATTGCATGAT

CTATGATAGCTTGGTGCTAAAGATTGAATGATTTCACAGGTTAAGCTCT

CTGGTTCCATTAGCAGTCAATACCTGAGTTCCTTGCTGATGGCTGCTCC

TTTGGCTCTTGAGGATGTCGAGATTGAAATCATTGATAAACTGATCTCC

GTTCCTTATGTTGAAATGACATTGAAATTGATGGAGCGTTTTGGTGTGA

CTGCGGAGCATTCTGATAGTTGGGACAGATTCTACATTAAGGGAGGACA

AAAATACAAGCAAGTTCTACATTTTCCTACTTCTTCTAATAAACTTTTA

ATTGTTTCATTTCTTCTAATAGTGGAGTACTAATGAAAGATATCAGTTT

TCAGTTTGCCAAATATTTACAGACGCAACCCCATTGAATTATGGGTGAA

CTAGGAAATAAATGTTTTACTAAAACTATTGACTGCTCAGTAGCTATGA

AGGTGCACTGTACTATGAAACCAGTGCCTACTGCCTAGGCAATCGGCCC

CACTGCTTACAATGAATTGTACAGTTACGTTTTCTGGTACATAGACTTG

ATCACACCAGAAGTATAATCCATCTTAAAAATGGAAAAAAATAGAGAAT

ATTTTGCGATGAGCATCTATGCAGATGATTCTTGATTTTGCTTCTTTTG

GCCCTTTCTAAGTTATGCCCTTGCTGCTATATGTCACATCTACGCTTTT

ACTGAACATACTCCTCTTATGTACTCGGAAACTGTTAGTCCAAACTTCA

TAAAAGTTGCAGTAAC

SEQ ID NO: 7 shows the DNA sequence of a PCR product that comprises a partial genomic DNA sequence for EPSPS for the B genome of wheat.

CCTTGGATCTCCGTGGAAGCAGATAAAGTTGCAAAAAGAGCTGTGGTTG

TTGGCTGTGGCGGCAGGTTCCCGGTCGAAAAGGACGCCAAAGAGGAAGT

AAAGCTCTTCTTGGGTAATGCTGGAACTGCAATGCGGCCATTGACGGCA

GCTGTAGTTGCTGCTGGTGGAAATGCAACGTATGTTTTCTTTATCCTAG

TGAAATAAGTATGAGATCCATGGGTATGTTTGGAGACTGATCATGTCYT

TTATTTAAAAAAAAAACTTCAGTTATGTGCTTGATGGAGTACCAAGAAT

GAGGGAGCGACCTATTGGTGACTTGGTTGTCGGTTTGCAACAACTCGGC

GCARATGCTGATTGTTTCCTTGGCACTAACTGCCCACCTGTCCGTATCA

ATGGCAAAGGAGGGCTACCTGGTGGCAAGGTTAGCTACTCGTGAAATTG

CATGTTATGTACTTTTGAGCACATTCAGTTCTCTGTCAAAGAAAACAAA

TATTATATTGGTAGTACGATCAATGCGACCTTACACAATGCACTAAAGT

TGAAGAACCAATARACATTGAATAATTTCAATACTTGAGTATTGCATGA

TCAATCATAGATTGACACTTAATATTGAATAATTTCACAGGTTAAGCTC

TCTGGTTCCATTAGCAGTCAATACCTGAGTTCCTTGCTGATGGCTGCTC

CTTTGGCTCTTGAAGATGTCGAGATTGAAATCATTGATAAACTGATCTC

CGTTCCTTACGTTGAAATGACATTGAAATTGATGGAGCGTTTTGGCGTG

```
ACTGCGGCGCATTCTGATAGTTGGGACAGATTCWACATCAAGGGAGGAC

AAAAATACAAGTAAGTTCTACATTGCTTTACTTCTTCTGATAGTGGAGT

ACAAAAGCATGATTCTAATTTTCTGTCTACCCACATATTTATAGACGCA

CCCCCATTTGAATTATTGATAAACTAGGAAATAAATATTGTACAAAATC

TGTCGACTGCTCAGTAGCTCTGAAGGCGCACTGTGCTAGGAAACCAGTG

TCTACTGCCTAGGCAATCAACCCTTCTACCTACAATGCATTGCACAGTT

CTGTTTTCTGGACATATACTTGATCACACCAGAAGTATCATCCATCTTA

AAATTGGACTGARAATAGAGAACATCGGCAGTTGTTTGGCAATGAGCAT

CTATGCAGATGATTCTTGATTTTGCTTCTTTTGGCCCTTTTTTATCTTA

TGCCCTTGCTGCCATATGGCCCATCAGGATACACATCCATGCTTTTACT

GAACATACTCTTATGTACTCGGAAACTGTTAGTTTAAACTTCATAAAAG

TTGCAGTAACCATTTCCTAAACGAGCCATCTGTTCTCGGAATCGACAG
```

SEQ ID NO: 8 shows the DNA sequence of a PCR product that comprises a partial genomic DNA sequence for EPSPS for the D genome of wheat

```
ACGCCAAAGAGGAAGTAAAGCTCTTCTTGGGTAATGCTGGAATGCAATG

CGTCCATTGACGGCAGCTGTAGTAGCTGCTGGTGGAAATGCAACGTATG

TTTTCTTTATCCTAGTTGAAATAAGTATGAGATCCATGGGTATGTTTGG

AGACTGATCGTGTCTTTTATTAAAAAAAAAcACTTCAGTTATGTGCTTG

ATGGAGTACCAAGAATGAGGGAGCGACCTATTGGTGACTTAGTTGTAGG

TTTGCAACAACTCGGCGCAGATGCTGATTGTTTCCTTGGCACTAACTGC

CCACCTGTTCGTATCAATGGCAAAGGAGGGCTACCTGGTGGCAAGGTTA

GCTACTTGTGAACTTGCATGTTATGTACTTTTGTGCACATTCAGTTCTC

TGTCAAAGAAAAATAATATTATTATGGGTAGTACGATGCAACGCGACCT

TACACCGTGCACTAAAGTTTAAGAACCAATAAACATTGAATAAATTCAA

TACTTGAGTATTGCGTGATCAATCATAGATTGGCGCTTAACATTGAATA

ATTTCACAGGTTAAGCTCTCTGGTTCCATTAGCAGTCAATACCTGAGTT

CCTTGCTGATGGCTGCTCCTTTGGCTCTTGAGGATGTCGAGATTGAAAT

CATTGATAAACTGATCTCCGTTCCTTACGTTGAAATGACATTGAAATTG

ATGGAGCGTTTTGGCGTGACTGCGGAGCATTCTGATAGTTGGGACAGAT

TCTACATTAAGGGAGGACAAAAGTACAAGTAAGTTCTACATTGCTTTAC

TTCTTCTGATAGTGGAGTACAAAAGCATGATTCTAGTTTTCAGTCTACC

CAAATATTTATAGACGCACCCCCATTTGAATTATTGATAAACTAGGAAA

TAAATATTGTACAAAATCTGTCGACTGCTCAGTAGCTTTCAAGGCGCAC

TGTACTAGGAAACCAGTGCCTACTGCCTAGGCAATCGACCCTGCTACCT

ACAATGCATTGCACAGTTCTGTTTTCTGGACATAGACTTGATCACACCA

GAAGTATCATCCATCTTAAAATTGGACTGAAAATAGAGGATATCGGCAG

TTGTTTGGCAATGAGCATCTATGCAGATGATACTTGATTTTGCTTCTTT

TGACCCTTTTTATCTTAGGCCCTTGCTGCCATATGGCCCATCAGGATAC

ACATCCATGCTTATACTGAACATACTCTTATGTACTCGGAAACTGTTAG

TTCAAACTTCATAAAAGTTGCAGTAACCATTTCCTAAACGAGCCATCCG

TTCTC
```

SEQ ID NO: 9 shows the amino acid sequence of the wheat EPSPS protein.

```
MAMAAAATVAASASSSAVSLDRAAPAHPRRLRMPAARAAHRGAVRLWGPR

GAAARATSVAAPAAPAGAEE

VVLQPIREISGAVQLPGSKSLSNRILLLSALSEGTTVVDNLLNSEDVHYM

LEALEALGLSVEADKVAKRAVVVGCGGRFPVEKDAKEEVKLFLGNAGTAM

RPLTAAVVAAGGNATYVLDGVPRMRERPIGDLVVGLQQLGADVDCFLGTN

CPPVRINGKGGLPGGKVKLSGSISSQYLSSLLMAAPLALEDVEIEIIDKL

ISVPYVEMTLKLMERFGVTAEHSDSWDRFYIKGGQKYKSPGNAYVEGDAS

SASYELAGAAITGGTVTVEGCGTTSLQGDVKFAEVLEMMGAKVTWTDTSV

TVTGPPRQPFGRKHLKAVDVNMNKMPDVAMTLAVVALFADGPTAIRDVAS

WRVKETERMVAIRTELTKLGATVEEGPDYCIITPPEKLNITAIDTYDDHR

MAMAFSLAACAEVPVTIRDPGCTRKTFPNYEDVLSTFVKN*
```

SEQ ID NOs: 10-13 show the DNA sequences for wheat EPSPS-specific primers used for mutation detection.

| SEQ ID | Primer Name | Primer ID | Primer Sequence |
|---|---|---|---|
| 10 | TaEPS1CL | 3155 | ACAGTGAGGATGTCCACTACATGCTTGA |
| 11 | Ep486AR | 3418 | ACTTCTCTGACAGAGAACAGAAGTGTGCAC |
| 12 | Ep558BR | 3419 | TTGTGTAAGGTCGCATTGATCGTACTACCA |
| 13 | TaEPSJR | 3223 | GAAAACTAGAATCATGCTTTTGTACTCCACTATC |

SEQ ID NOs: 14-17 show TaqMan® Primers Useful for T173I Mutation Detection.

| SEQ ID | Primer Name | Primer Sequence |
|---|---|---|
| 14 | HT_TtoI-TtoIF | ACGCCAAAGAGGAAGTAAAGCT |
| 15 | HT_TtoI-TtoIR | TCCAAACATACCCATGGATCTCATACT |
| 16 | HT_TtoI-TtoIV2 VIC | CGCATTGCAGTTCCA |
| 17 | HT_TtoI-TtoIM2 FAM | CATTGCAATTCCA |

SEQ ID NO. 18 shows the active region of the wheat EPSPS protein:

FLGNAGTAMRPLTAAVVAAGGN.

What is claimed is:

1. A wheat plant comprising a human-induced non-transgenic mutation in an EPSPS gene in each of the A, B, and D genomes, wherein the EPSPS gene of the A genome is homozygous for at least two mutations and encodes an EPSPS polypeptide comprising a threonine to isoleucine change at amino acid position 168 (T168I) and a proline to serine change at amino acid position 172 (P172S) of SEQ ID NO. 9, and wherein the EPSPS gene of the D genome is homozygous for at least two mutations and encodes an EPSPS polypeptide comprising a threonine to isoleucine change at amino acid position 168 (T168I) and a proline to serine change at amino acid position 172 (P172S) of SEQ ID NO. 9, and wherein the EPSPS gene of the B genome is homozygous for a mutation and encodes an EPSPS polypeptide comprising a threonine to isoleucine change at amino acid position 168 of SEQ ID NO. 9, and wherein the mutations in the EPSPS genes contribute to a wheat plant having resistance to glyphosate as compared to a wild type wheat plant.

2. The wheat plant of claim 1, wherein the EPSPS gene of the A genome has one or more additional mutations and encodes an EPSPS polypeptide having one or more mutations recited in Table 4.

3. The wheat plant of claim 1, wherein the EPSPS gene of the B genome has one or more additional mutations and encodes an EPSPS polypeptide having one or more mutations recited in Table 4.

4. The wheat plant of claim 1, wherein the EPSPS gene of the D genome has one or more additional mutations and encodes an EPSPS polypeptide having one or more mutations recited in Table 4.

5. The wheat plant of claim 1, which is *Triticum aestivum* ssp. *aestivum*.

6. Wheat grain from the wheat plant of claim 1.

7. Flour comprising the wheat grain of claim 6.

8. A food product comprising a component of the wheat plant of claim 1.

9. A wheat seed, plant part or progeny thereof from the wheat plant of claim 1, wherein said progeny comprises the mutations in the EPSPS gene in each of the A, B, and D genomes.

10. The wheat plant of claim 1, wherein the EPSPS gene of the B genome is homozygous for a an additional mutation that encodes an EPSPS polypeptide comprising a proline to serine change at amino acid position 172 (P172S) of SEQ ID NO. 9.

* * * * *

SEQUENCE LISTING

<160> NUMBER OF SEQ ID NOS: 21

<210> SEQ ID NO 1
<211> LENGTH: 1585
<212> TYPE: DNA
<213> ORGANISM: Oryza sativa

<400> SEQUENCE: 1

| | | | | | |
|---|---|---|---|---|---|
| atggcggcga | ccatggcgtc | caacgccgcg | gctgcggcgg | cggtgtccct | ggaccaggcc | 60 |
| gtggcggcgt | cggcggcgtt | ctcgtcgcgg | aagcagctgc | ggctgcccgc | cgcggcgcgc | 120 |
| gggggatgc | gggtgcgggt | gcggcgcgg | gggcggcggg | aggcggtggt | ggtggcgtcc | 180 |
| gcgtcgtcgt | cgtcggtggc | agcgccggcg | gcgaaggcgg | aggagatcgt | gctccagccc | 240 |
| atcagggaga | tctccggggc | ggttcagctg | ccagggtcca | agtcgctctc | caacaggatc | 300 |
| ctcctcctct | ccgccctctc | cgagggcaca | acagtggtgg | acaacttgct | gaacagtgag | 360 |
| gatgttcact | acatgcttga | ggccctgaaa | gccctcgggc | tctctgtgga | agcagataaa | 420 |
| gttgcaaaaa | gagctgtagt | cgttggctgt | ggtggcaagt | ttcctgttga | aaggatgcg | 480 |
| aaagaggaag | tgcaactctt | cttggggaac | gctggaactg | caatgcgacc | attgacagca | 540 |
| gccgtgactg | ctgctggtgg | aaatgcaact | tatgtgcttg | atggagtgcc | acgaatgagg | 600 |
| gagagaccga | ttggtgactt | ggttgtcggg | ttgaaacaac | ttggtgcgga | tgtcgactgt | 660 |
| ttccttggca | ctgaatgccc | acctgttcgt | gtcaagggaa | ttggaggact | tcctggtggc | 720 |
| aaggttaagc | tctctggttc | catcagcagt | cagtacttga | gtgccttgct | gatggctgct | 780 |
| cctttggccc | ttggggatgt | ggagatcgaa | atcattgaca | aactaatctc | cattccttac | 840 |
| gttgaaatga | cattgagatt | gatggagcgt | tttggtgtga | aggcagagca | ttctgatagt | 900 |
| tgggacagat | tctatattaa | gggagggcag | aagtacaaat | ctcctggaaa | tgcctatgtt | 960 |
| gaaggtgatg | cctcaagcgc | gagctatttc | ttggctggtg | ctgcaatcac | tggaggcact | 1020 |
| gtgacagttc | aaggttgtgg | tacgaccagt | ttgcagggtg | atgtcaaatt | tgctgaggta | 1080 |
| cttgagatga | tgggagcaaa | ggttacatgg | actgacacca | gtgtaaccgt | aactggtcca | 1140 |
| ccacgtgagc | cttatgggaa | gaaacacctg | aaagctgttg | atgtcaacat | gaacaaaatg | 1200 |
| cctgatgttg | ccatgaccct | tgccgttgtt | gcactcttcg | ctgatggtcc | aactgctatc | 1260 |
| agagatgtgg | cttcctggag | agtaaaggaa | accgaaagga | tggttgcaat | tcggaccgag | 1320 |
| ctaacaaagc | tgggagcatc | ggttgaagaa | ggtcctgact | actgcatcat | caccccaccg | 1380 |
| gagaagctga | acatcacggc | aatcgacacc | tacgatgatc | acaggatggc | catggccttc | 1440 |
| tccctcgctg | cctgcgccga | cgtgcccgtg | acgatcaggg | accctggttg | cacccgcaag | 1500 |
| accttcccca | actacttcga | cgttctaagc | actttcgtca | ggaactgaac | tgagctttta | 1560 |
| aaagagtgag | gtctaggttc | tgttg | | | | 1585 |

<210> SEQ ID NO 2
<211> LENGTH: 3304
<212> TYPE: DNA
<213> ORGANISM: Oryza sativa

<400> SEQUENCE: 2

| | | | | | |
|---|---|---|---|---|---|
| atggcggcga | ccatggcgtc | caacgccgcg | gctgcggcgg | cggtgtccct | ggaccaggcc | 60 |
| gtggcggcgt | cggcggcgtt | ctcgtcgcgg | aagcagctgc | ggctgcccgc | cgcggcgcgc | 120 |
| gggggatgc | gggtgcgggt | gcggcgcgg | gggcggcggg | aggcggtggt | ggtggcgtcc | 180 |
| gcgtcgtcgt | cgtcggtggc | agcgccggcg | gcgaaggcgg | aggagatcgt | gctccagccc | 240 |

```
atcagggaga tctccggggc ggttcagctg ccagggtcca agtcgctctc caacaggatc     300
ctcctcctct ccgccctctc cgaggtgaga cgcggatccc ttcctcttgc gtgaattcca     360
tttctggaga tgagatttta gggggtttat taggtgaggt ggctgtgttt gtgaaatcct     420
aggaattatc tctcaagtca atctaacgat gagatataac tgaggttctg gttttaatca     480
cacactcata taaccaattt attgaaacat tttggtttgg cataagaaac tgcttacgaa     540
ggtatgatat cctcctacat gtcaggctac taaattttca cgacggtatg atccactcaa     600
aacaagtttc ttaacgagtc tggtgaggtc tgttatgaaa tttgtgtaaa ctaaggcaac     660
tttggaggtt tcgcactgta ccaatgttat gtttgaacat tttgcaagca gtgctttctc     720
ccaaaattat gcaattttga ggctcctcta catcattata attccccaat acattgctct     780
ttattcttaa tagctttgat cgcgaaattt aacattttaa ttcttgagct gttattttgt     840
agcatcagtt tatcatgagc catgtttggt actaaatata caatcccttg ggtttatttg     900
tttccaagca tgtcattaac ttatcttaat gtggacaaga aactgatgcc tgcttacatt     960
gctattattt caagcgggta ttgatccttt gacatgtgat tgatcatttt ttttctctg    1020 gttattaggg cacaacagtg gtggacaact tgctgaacag tgaggatgtt cactacatgc    1080
ttgaggccct gaaagccctc gggctctctg tggaagcaga taaagttgca aaagagctg    1140 tagtcgttgg ctgtggtggc aagtttcctg ttgagaagga tgcgaaagag gaagtgcaac    1200
tcttcttggg gaacgctgga actgcaatgc gaccattgac agcagccgtg actgctgctg    1260
gtggaaatgc aacgtatgtt tttttttta atgtttatga aaatatgtat ggaattcatg    1320
gggtatgttt tatgaccttt ttctttacca tcagttatgt gcttgatgga gtgccacgaa    1380
tgagggagag accgattggt gacttggttg tcgggttgaa acaacttggt gcggatgtcg    1440
actgtttcct tggcactgaa tgcccacctg ttcgtgtcaa gggaattgga ggacttcctg    1500
gtggcaaggt tagttactcc taaactgcat cctttgtact tctgtatgca cctcaattct    1560
ttgtcaacct tctgcattta taggaacat tctatgatgc aattcgacct tacactgcac    1620
agtaacttga atgtttcat gcttaatcaa tatgccatat tcctgccaag ctcaagcgag    1680
caatatttgt ttgaatttgg taccatattt ttgtatattt gggcattcct ttttggtctt    1740
gatgtcttct tttgaattag catttaactg aattacactc aacaggttaa gctctctggt    1800
tccatcagca gtcagtactt gagtgccttg ctgatggctg ctcctttggc ccttggggat    1860
gtggagatcg aaatcattga caaactaatc tccattcctt acgttgaaat gacattgaga    1920
ttgatggagc gttttggtgt gaaggcagag cattctgata gttgggacag attctatatt    1980
aagggagggc agaagtacaa gtaagcttct acctgcctta ctgagctgaa ttattcgggt    2040
gtttatgatt aactccctaa actaacccct tttctttct ttggcattga cagatctcct    2100
ggaaatgcct atgttgaagg tgatgcctca agcgcgagct atttcttggc tggtgctgca    2160
atcactggag gcactgtgac agttcaaggt tgtggtacga ccagtttgca ggtataactg    2220
tagtgcctgt tttgacattc taccgtttag tcaagtttag tcagtagtca catattcaga    2280
atatagcaca atctgtatta tgccactgtt aatcaaatac gcttgaccta gagagtgcta    2340 tatccctag cttaatcttc aaactaaaca gttctcttgt ggcttgctgt gctgttatgt    2400
tccctgacct acatgttaat attacagggt gatgtcaaat ttgctgaggt acttgagatg    2460
atgggagcaa aggttacatg gactgacacc agtgtaaccg taactggtcc accacgtgag    2520
ccttatggga agaaacacct gaaagctgtt gatgtcaaca tgaacaaaat gcctgatgtt    2580
```

| | | |
|---|---|---|
| gccatgacccc ttgccgttgt tgcactcttc gctgatggtc caactgctat cagagatggt | 2640 |
| aaacattaag gcctattata cctgttctat catactagca attactgctt agcattgtga | 2700 |
| caaaacaaat aaccaaactt tcttcaaaat aacttagaaa tataagaaag gttcgttttg | 2760 |
| tgtggtaaac agtactactg tagtttcagc tatgaagttt gctgctggca attttctgaa | 2820 |
| cggtttcagc taaattgcat gtttgttcat catacttatc cattgtcttc cacagtggct | 2880 |
| tcctggagag taaggaaac cgaaaggatg gttgcaattc ggaccgagct aacaaaggta | 2940 |
| aattcattag gtcccgtgtc ctttcattct tcaagtagtt tgttcataag ttgaattctc | 3000 |
| cttcaatgat gtttaaattc atcatcttct ttttggtgt tgtgccagct gggagcatcg | 3060 |
| gttgaagaag gtcctgacta ctgcatcatc accccaccgg agaagctgaa catcacggca | 3120 |
| atcgacacct acgatgatca caggatggcc atggccttct ccctcgctgc ctgcgccgac | 3180 |
| gtgcccgtga cgatcaggga ccctggttgc acccgcaaga ccttccccaa ctacttcgac | 3240 |
| gttctaagca ctttcgtcag gaactgaact gagcttttaa aagagtgagg tctaggttct | 3300 |
| gttg | 3304 |

<210> SEQ ID NO 3
<211> LENGTH: 515
<212> TYPE: PRT
<213> ORGANISM: Oryza sativa

<400> SEQUENCE: 3

Met Ala Ala Thr Met Ala Ser Asn Ala Ala Ala Ala Ala Val Ser
1               5                   10                  15

Leu Asp Gln Ala Val Ala Ala Ser Ala Ala Phe Ser Ser Arg Lys Gln
            20                  25                  30

Leu Arg Leu Pro Ala Ala Ala Arg Gly Gly Met Arg Val Arg Val Arg
        35                  40                  45

Ala Arg Gly Arg Arg Glu Ala Val Val Ala Ser Ala Ser Ser Ser
    50                  55                  60

Ser Val Ala Ala Pro Ala Ala Lys Ala Glu Glu Ile Val Leu Gln Pro
65                  70                  75                  80

Ile Arg Glu Ile Ser Gly Ala Val Gln Leu Pro Gly Ser Lys Ser Leu
                85                  90                  95

Ser Asn Arg Ile Leu Leu Leu Ser Ala Leu Ser Glu Gly Thr Thr Val
            100                 105                 110

Val Asp Asn Leu Leu Asn Ser Glu Asp Val His Tyr Met Leu Glu Ala
        115                 120                 125

Leu Lys Ala Leu Gly Leu Ser Val Glu Ala Asp Lys Val Ala Lys Arg
    130                 135                 140

Ala Val Val Val Gly Cys Gly Gly Lys Phe Pro Val Glu Lys Asp Ala
145                 150                 155                 160

Lys Glu Glu Val Gln Leu Phe Leu Gly Asn Ala Gly Thr Ala Met Arg
                165                 170                 175

Pro Leu Thr Ala Ala Val Thr Ala Ala Gly Gly Asn Ala Thr Tyr Val
            180                 185                 190

Leu Asp Gly Val Pro Arg Met Arg Glu Arg Pro Ile Gly Asp Leu Val
        195                 200                 205

Val Gly Leu Lys Gln Leu Gly Ala Asp Val Asp Cys Phe Leu Gly Thr
    210                 215                 220

Glu Cys Pro Pro Val Arg Val Lys Gly Ile Gly Gly Leu Pro Gly Gly
225                 230                 235                 240

```
Lys Val Lys Leu Ser Gly Ser Ile Ser Ser Gln Tyr Leu Ser Ala Leu
            245                 250                 255

Leu Met Ala Ala Pro Leu Ala Leu Gly Asp Val Glu Ile Glu Ile Ile
        260                 265                 270

Asp Lys Leu Ile Ser Ile Pro Tyr Val Glu Met Thr Leu Arg Leu Met
            275                 280                 285

Glu Arg Phe Gly Val Lys Ala Glu His Ser Asp Ser Trp Asp Arg Phe
        290                 295                 300

Tyr Ile Lys Gly Gly Gln Lys Tyr Lys Ser Pro Gly Asn Ala Tyr Val
305                 310                 315                 320

Glu Gly Asp Ala Ser Ser Ala Ser Tyr Phe Leu Ala Gly Ala Ala Ile
            325                 330                 335

Thr Gly Gly Thr Val Thr Val Gln Gly Cys Gly Thr Thr Ser Leu Gln
            340                 345                 350

Gly Asp Val Lys Phe Ala Glu Val Leu Glu Met Met Gly Ala Lys Val
        355                 360                 365

Thr Trp Thr Asp Thr Ser Val Thr Val Thr Gly Pro Pro Arg Glu Pro
        370                 375                 380

Tyr Gly Lys Lys His Leu Lys Ala Val Asp Val Asn Met Asn Lys Met
385                 390                 395                 400

Pro Asp Val Ala Met Thr Leu Ala Val Val Ala Leu Phe Ala Asp Gly
            405                 410                 415

Pro Thr Ala Ile Arg Asp Val Ala Ser Trp Arg Val Lys Glu Thr Glu
            420                 425                 430

Arg Met Val Ala Ile Arg Thr Glu Leu Thr Lys Leu Gly Ala Ser Val
        435                 440                 445

Glu Glu Gly Pro Asp Tyr Cys Ile Ile Thr Pro Pro Glu Lys Leu Asn
    450                 455                 460

Ile Thr Ala Ile Asp Thr Tyr Asp Asp His Arg Met Ala Met Ala Phe
465                 470                 475                 480

Ser Leu Ala Ala Cys Ala Asp Val Pro Val Thr Ile Arg Asp Pro Gly
            485                 490                 495

Cys Thr Arg Lys Thr Phe Pro Asn Tyr Phe Asp Val Leu Ser Thr Phe
            500                 505                 510

Val Arg Asn
        515

<210> SEQ ID NO 4
<211> LENGTH: 28
<212> TYPE: DNA
<213> ORGANISM: Artificial Sequence
<220> FEATURE:
<223> OTHER INFORMATION: Primer

<400> SEQUENCE: 4
acagtgagga tgtccactac atgcttga                                    28

<210> SEQ ID NO 5
<211> LENGTH: 28
<212> TYPE: DNA
<213> ORGANISM: Artificial Sequence
<220> FEATURE:
<223> OTHER INFORMATION: Primer

<400> SEQUENCE: 5
aaatagctcg cacttgaggc atcacctt                                    28
```

<210> SEQ ID NO 6
<211> LENGTH: 1339
<212> TYPE: DNA
<213> ORGANISM: Triticum aestivum

<400> SEQUENCE: 6

| | | | | | |
|---|---|---|---|---|---|
| gaccttggat | ctccgtggaa | gcagataaag | ttgcaaaaag | agctgtggtt | gttggctgtg | 60 |
| gcggcaggtt | cccagtcgaa | aaggacgcca | agaggaagt | aaagctcttc | ttgggtaatg | 120 |
| ctggaactgc | aatgcggcca | ctgacggcag | ctgtagtagc | tgctggtgga | aatgcaacgt | 180 |
| atgttttctt | tatcctagtg | aaataagta | tgagatccat | gggtatgttt | ggagactgat | 240 |
| cgtttctttt | attaaaaaaa | aacttcagtt | atgtgcttga | tggcgtacca | agaatgaggg | 300 |
| agcgacctat | tggtgactta | gttgtaggtt | tgcaacaact | cggcgcagat | gtcgattgtt | 360 |
| tccttggcac | aaactgccca | cctgtccgta | tcaacggcaa | aggaggtcta | cctggtggca | 420 |
| aggttagcta | ctcatcaact | tgcatgttat | ctactttgtg | cacacttctg | ttctctgtca | 480 |
| gagaagttat | tattatggct | agtacgatgt | aatgcaacct | tagaccgcgc | actaaatttt | 540 |
| aagaaccaat | caacatttaa | taatttcaat | atgtgagtat | tgcatgatct | atgatagctt | 600 |
| ggtgctaaag | attgaatgat | ttcacaggtt | aagctctctg | gttccattag | cagtcaatac | 660 |
| ctgagttcct | tgctgatggc | tgctcctttg | gctcttgagg | atgtcgagat | tgaaatcatt | 720 |
| gataaactga | tctccgttcc | ttatgttgaa | atgacattga | aattgatgga | gcgttttggt | 780 |
| gtgactgcgg | agcattctga | tagttgggac | agattctaca | ttaagggagg | acaaaaatac | 840 |
| aagcaagttc | tacattttcc | tacttcttct | aataaacttt | taattgtttc | atttcttcta | 900 |
| atagtggagt | actaatgaaa | gatatcagtt | ttcagtttgc | caaatattta | cagacgcaac | 960 |
| cccattgaat | tatgggtgaa | ctaggaaata | aatgttttac | taaaactatt | gactgctcag | 1020 |
| tagctatgaa | ggtgcactgt | actatgaaac | cagtgcctac | tgcctaggca | atcggcccca | 1080 |
| ctgcttacaa | tgaattgtac | agttacgttt | tctggtacat | agacttgatc | acaccagaag | 1140 |
| tataatccat | cttaaaaatg | gaaaaaaata | gagaatattt | tgcgatgagc | atctatgcag | 1200 |
| atgattcttg | attttgcttc | ttttggcct | ttctaagtta | tgcccttgct | gctatatgtc | 1260 |
| acatctacgc | ttttactgaa | catactcctc | ttatgtactc | ggaaactgtt | agtccaaact | 1320 |
| tcataaaagt | tgcagtaac | | | | | 1339 |

<210> SEQ ID NO 7
<211> LENGTH: 1371
<212> TYPE: DNA
<213> ORGANISM: Triticum aestivum

<400> SEQUENCE: 7

| | | | | | |
|---|---|---|---|---|---|
| ccttggatct | ccgtggaagc | agataaagtt | gcaaaagag | ctgtggttgt | tggctgtggc | 60 |
| ggcaggttcc | cggtcgaaaa | ggacgccaaa | gaggaagtaa | agctcttctt | gggtaatgct | 120 |
| ggaactgcaa | tgcggccatt | gacggcagct | gtagttgctg | ctggtggaaa | tgcaacgtat | 180 |
| gttttcttta | tcctagtgaa | ataagtatga | gatccatggg | tatgtttgga | gactgatcat | 240 |
| gtcytttatt | taaaaaaaaa | acttcagtta | tgtgcttgat | ggagtaccaa | gaatgaggga | 300 |
| gcgacctatt | ggtgacttgg | ttgtcggttt | gcaacaactc | ggcgcaratg | ctgattgttt | 360 |
| ccttggcact | aactgcccac | ctgtccgtat | caatggcaaa | ggagggctac | tggtggcaa | 420 |
| ggttagctac | tcgtgaaatt | gcatgttat | actttgtag | cacattccgt | tctctgtcaa | 480 |
| agaaaacaaa | tattatattg | gtagtacgat | caatgcgacc | ttacacaatg | cactaaagtt | 540 |

```
gaagaaccaa taracattga ataatttcaa tacttgagta ttgcatgatc aatcatagat      600
tgacacttaa tattgaataa tttcacaggt taagctctct ggttccatta gcagtcaata      660
cctgagttcc ttgctgatgg ctgctccttt ggctcttgaa gatgtcgaga ttgaaatcat      720
tgataaactg atctccgttc cttacgttga aatgacattg aaattgatgg agcgttttgg      780
cgtgactgcg gcgcattctg atagttggga cagattcwac atcaagggag acaaaaata      840 caagtaagtt ctacattgct ttacttcttc tgatagtgga gtacaaaagc atgattctaa      900
ttttctgtct acccacatat ttatagacgc accccatttt gaattattga taaactagga      960
aataaatatt gtacaaaatc tgtcgactgc tcagtagctc tgaaggcgca ctgtgctagg     1020
aaaccagtgt ctactgccta ggcaatcaac ccttctacct acaatgcatt gcacagttct     1080
gttttctgga catatacttg atcacaccag aagtatcatc catcttaaaa ttggactgar     1140
aatagagaac atcggcagtt gtttggcaat gagcatctat gcagatgatt cttgattttg     1200
cttcttttgg cccttttttta tcttatgccc ttgctgccat atggcccatc aggatacaca     1260
tccatgcttt tactgaacat actcttatgt actcggaaac tgttagttta aacttcataa     1320
aagttgcagt aaccatttcc taaacgagcc atctgttctc ggaatcgaca g              1371
```

<210> SEQ ID NO 8
<211> LENGTH: 1280
<212> TYPE: DNA
<213> ORGANISM: Triticum aestivum

<400> SEQUENCE: 8

```
acgccaaaga ggaagtaaag ctcttcttgg gtaatgctgg aactgcaatg cgtccattga       60
cggcagctgt agtagctgct ggtggaaatg caacgtatgt tttctttatc ctagttgaaa      120
taagtatgag atccatgggt atgttggag actgatcgtg tcttttatta aaaaaaaaca      180
cttcagttat gtgcttgatg gagtaccaag aatgagggag cgacctattg gtgacttagt      240 tgtaggttg caacaactcg gcgcagatgc tgattgtttc cttggcacta actgccacc       300 tgttcgtatc aatggcaaag gagggctacc tggtggcaag gttagctact tgtgaacttg      360
catgttatgt acttttgtgc acattcagtt ctctgtcaaa gaaaataat attattatgg      420 gtagtacgat gcaacgcgac cttacaccgt gcactaaagt ttaagaacca ataaacattg      480
aataaattca atacttgagt attgcgtgat caatcataga ttggcgctta acattgaata      540
atttcacagg ttaagctctc tggttccatt agcagtcaat acctgagttc cttgctgatg      600
gctgctcctt tggctcttga ggatgtcgag attgaaatca ttgataaact gatctccgtt      660
ccttacgttg aaatgacatt gaaattgatg gagcgttttg gcgtgactgc ggagcattct      720
gatagttggg acagattcta cattaaggga ggacaaaagt acaagtaagt tctacattgc      780
tttacttctt ctgatagtgg agtacaaaag catgattcta gttttcagtc tacccaaata      840
tttatagacg caccccccatt tgaattattg ataaactagg aaataaatat tgtacaaaat      900
ctgtcgactg ctcagtagct ttcaaggcgc actgtactag gaaaccagtg cctactgcct      960
aggcaatcga ccctgctacc tacaatgcat tgcacagttc tgttttctgg acatagactt     1020
gatcacacca aagtatcat ccatcttaaa attggactga aaatagagga tatcggcagt     1080
tgtttggcaa tgagcatcta tgcagatgat acttgattt gcttcttttg accctttttta     1140 tcttaggccc ttgctgccat atggcccatc aggatacaca tccatgctta tactgaacat     1200
actcttatgt actcggaaac tgttagttca aacttcataa aagttgcagt aaccatttcc     1260
taaacgagcc atccgttctc                                                  1280
```

<210> SEQ ID NO 9
<211> LENGTH: 510
<212> TYPE: PRT
<213> ORGANISM: Triticum aestivum

<400> SEQUENCE: 9

Met Ala Met Ala Ala Ala Thr Val Ala Ala Ser Ala Ser Ser Ser
1               5                   10                  15

Ala Val Ser Leu Asp Arg Ala Ala Ala His Pro Arg Arg Leu Arg
            20                  25                  30

Met Pro Ala Ala Arg Ala Ala His Arg Gly Ala Val Arg Leu Trp Gly
        35                  40                  45

Pro Arg Gly Ala Ala Ala Arg Ala Thr Ser Val Ala Ala Pro Ala Ala
50                  55                  60

Pro Ala Gly Ala Glu Glu Val Val Leu Gln Pro Ile Arg Glu Ile Ser
65                  70                  75                  80

Gly Ala Val Gln Leu Pro Gly Ser Lys Ser Leu Ser Asn Arg Ile Leu
                85                  90                  95

Leu Leu Ser Ala Leu Ser Glu Gly Thr Thr Val Val Asp Asn Leu Leu
            100                 105                 110

Asn Ser Glu Asp Val His Tyr Met Leu Glu Ala Leu Glu Ala Leu Gly
        115                 120                 125

Leu Ser Val Glu Ala Asp Lys Val Ala Lys Arg Ala Val Val Val Gly
    130                 135                 140

Cys Gly Gly Arg Phe Pro Val Glu Lys Asp Ala Lys Glu Glu Val Lys
145                 150                 155                 160

Leu Phe Leu Gly Asn Ala Gly Thr Ala Met Arg Pro Leu Thr Ala Ala
                165                 170                 175

Val Val Ala Ala Gly Gly Asn Ala Thr Tyr Val Leu Asp Gly Val Pro
            180                 185                 190

Arg Met Arg Glu Arg Pro Ile Gly Asp Leu Val Val Gly Leu Gln Gln
        195                 200                 205

Leu Gly Ala Asp Val Asp Cys Phe Leu Gly Thr Asn Cys Pro Pro Val
    210                 215                 220

Arg Ile Asn Gly Lys Gly Gly Leu Pro Gly Gly Lys Val Lys Leu Ser
225                 230                 235                 240

Gly Ser Ile Ser Ser Gln Tyr Leu Ser Ser Leu Leu Met Ala Ala Pro
                245                 250                 255

Leu Ala Leu Glu Asp Val Glu Ile Glu Ile Asp Lys Leu Ile Ser
            260                 265                 270

Val Pro Tyr Val Glu Met Thr Leu Lys Leu Met Glu Arg Phe Gly Val
        275                 280                 285

Thr Ala Glu His Ser Asp Ser Trp Asp Arg Phe Tyr Ile Lys Gly Gly
    290                 295                 300

Gln Lys Tyr Lys Ser Pro Gly Asn Ala Tyr Val Glu Gly Asp Ala Ser
305                 310                 315                 320

Ser Ala Ser Tyr Phe Leu Ala Gly Ala Ala Ile Thr Gly Gly Thr Val
                325                 330                 335

Thr Val Glu Gly Cys Gly Thr Thr Ser Leu Gln Gly Asp Val Lys Phe
            340                 345                 350

Ala Glu Val Leu Glu Met Met Gly Ala Lys Val Thr Trp Thr Asp Thr
        355                 360                 365

Ser Val Thr Val Thr Gly Pro Pro Arg Gln Pro Phe Gly Arg Lys His

```
              370                 375                 380
Leu Lys Ala Val Asp Val Asn Met Asn Lys Met Pro Asp Val Ala Met
385                 390                 395                 400

Thr Leu Ala Val Val Ala Leu Phe Ala Asp Gly Pro Thr Ala Ile Arg
                405                 410                 415

Asp Val Ala Ser Trp Arg Val Lys Glu Thr Glu Arg Met Val Ala Ile
            420                 425                 430

Arg Thr Glu Leu Thr Lys Leu Gly Ala Thr Val Glu Glu Gly Pro Asp
        435                 440                 445

Tyr Cys Ile Ile Thr Pro Pro Glu Lys Leu Asn Ile Thr Ala Ile Asp
    450                 455                 460

Thr Tyr Asp Asp His Arg Met Ala Met Ala Phe Ser Leu Ala Ala Cys
465                 470                 475                 480

Ala Glu Val Pro Val Thr Ile Arg Asp Pro Gly Cys Thr Arg Lys Thr
                485                 490                 495

Phe Pro Asn Tyr Phe Asp Val Leu Ser Thr Phe Val Lys Asn
            500                 505                 510

<210> SEQ ID NO 10
<211> LENGTH: 28
<212> TYPE: DNA
<213> ORGANISM: Artificial Sequence
<220> FEATURE:
<223> OTHER INFORMATION: Primer

<400> SEQUENCE: 10
acagtgagga tgtccactac atgcttga                                       28

<210> SEQ ID NO 11
<211> LENGTH: 30
<212> TYPE: DNA
<213> ORGANISM: Artificial Sequence
<220> FEATURE:
<223> OTHER INFORMATION: Primer

<400> SEQUENCE: 11
acttctctga cagagaacag aagtgtgcac                                     30

<210> SEQ ID NO 12
<211> LENGTH: 30
<212> TYPE: DNA
<213> ORGANISM: Artificial Sequence
<220> FEATURE:
<223> OTHER INFORMATION: Primer

<400> SEQUENCE: 12
ttgtgtaagg tcgcattgat cgtactacca                                     30

<210> SEQ ID NO 13
<211> LENGTH: 34
<212> TYPE: DNA
<213> ORGANISM: Artificial Sequence
<220> FEATURE:
<223> OTHER INFORMATION: Primer

<400> SEQUENCE: 13
gaaaactaga atcatgcttt tgtactccac tatc                                34

<210> SEQ ID NO 14
<211> LENGTH: 22
<212> TYPE: DNA
<213> ORGANISM: Artificial Sequence
```

-continued

<220> FEATURE:
<223> OTHER INFORMATION: Primer

<400> SEQUENCE: 14
acgccaaaga ggaagtaaag ct                                           22

<210> SEQ ID NO 15
<211> LENGTH: 27
<212> TYPE: DNA
<213> ORGANISM: Artificial Sequence
<220> FEATURE:
<223> OTHER INFORMATION: Primer

<400> SEQUENCE: 15
tccaaacata cccatggatc tcatact                                      27

<210> SEQ ID NO 16
<211> LENGTH: 15
<212> TYPE: DNA
<213> ORGANISM: Artificial Sequence
<220> FEATURE:
<223> OTHER INFORMATION: Primer

<400> SEQUENCE: 16
cgcattgcag ttcca                                                   15

<210> SEQ ID NO 17
<211> LENGTH: 13
<212> TYPE: DNA
<213> ORGANISM: Artificial Sequence
<220> FEATURE:
<223> OTHER INFORMATION: Primer

<400> SEQUENCE: 17
cattgcaatt cca                                                     13

<210> SEQ ID NO 18
<211> LENGTH: 22
<212> TYPE: PRT
<213> ORGANISM: Triticum aestivum

<400> SEQUENCE: 18

Phe Leu Gly Asn Ala Gly Thr Ala Met Arg Pro Leu Thr Ala Ala Val
1               5                   10                  15

Val Ala Ala Gly Gly Asn
            20

<210> SEQ ID NO 19
<211> LENGTH: 510
<212> TYPE: PRT
<213> ORGANISM: Triticum aestivum

<400> SEQUENCE: 19

Met Ala Met Ala Ala Ala Ala Thr Val Ala Ala Ser Ala Ser Ser Ser
1               5                   10                  15

Ala Val Ser Leu Asp Arg Ala Ala Pro Ala His Pro Arg Arg Leu Arg
                20                  25                  30

Met Pro Ala Ala Arg Ala Ala His Arg Gly Ala Val Arg Leu Trp Gly
            35                  40                  45

Pro Arg Gly Ala Ala Ala Arg Ala Thr Ser Val Ala Ala Pro Ala Ala
        50                  55                  60

Pro Ala Gly Ala Glu Glu Val Val Leu Gln Pro Ile Arg Glu Ile Ser
65                  70                  75                  80

-continued

Gly Ala Val Gln Leu Pro Ser Lys Ser Leu Ser Asn Arg Ile Leu
                85                  90                  95

Leu Leu Ser Ala Leu Ser Glu Gly Thr Thr Val Val Asp Asn Leu Leu
            100                 105                 110

Asn Ser Glu Asp Val His Tyr Met Leu Glu Ala Leu Glu Ala Leu Gly
        115                 120                 125

Leu Ser Val Glu Ala Asp Lys Val Ala Lys Arg Ala Val Val Gly
    130                 135                 140

Cys Gly Gly Arg Phe Pro Val Glu Lys Asp Ala Lys Glu Val Lys
145                 150                 155                 160

Leu Phe Leu Gly Asn Ala Gly Thr Ala Met Arg Pro Leu Thr Ala Ala
                165                 170                 175

Val Val Ala Ala Gly Asn Ala Thr Tyr Val Leu Asp Gly Val Pro
            180                 185                 190

Arg Met Arg Glu Arg Pro Ile Gly Asp Leu Val Val Gly Leu Gln Gln
        195                 200                 205

Leu Gly Ala Asp Val Asp Cys Phe Leu Gly Thr Asn Cys Pro Pro Val
    210                 215                 220

Arg Ile Asn Gly Lys Gly Gly Leu Pro Gly Gly Lys Val Lys Leu Ser
225                 230                 235                 240

Gly Ser Ile Ser Ser Gln Tyr Leu Ser Ser Leu Leu Met Ala Ala Pro
                245                 250                 255

Leu Ala Leu Glu Asp Val Glu Ile Glu Ile Asp Lys Leu Ile Ser
            260                 265                 270

Val Pro Tyr Val Glu Met Thr Leu Lys Leu Met Glu Arg Phe Gly Val
        275                 280                 285

Thr Ala Glu His Ser Asp Ser Trp Asp Arg Phe Tyr Ile Lys Gly Gly
    290                 295                 300

Gln Lys Tyr Lys Ser Pro Gly Asn Ala Tyr Val Glu Gly Asp Ala Ser
305                 310                 315                 320

Ser Ala Ser Tyr Phe Leu Ala Gly Ala Ala Ile Thr Gly Gly Thr Val
                325                 330                 335

Thr Val Glu Gly Cys Gly Thr Thr Ser Leu Gln Gly Asp Val Lys Phe
            340                 345                 350

Ala Glu Val Leu Glu Met Met Gly Ala Lys Val Thr Trp Thr Asp Thr
        355                 360                 365

Ser Val Thr Val Thr Gly Pro Pro Arg Gln Pro Phe Gly Arg Lys His
    370                 375                 380

Leu Lys Ala Val Asp Val Asn Met Asn Lys Met Pro Asp Val Ala Met
385                 390                 395                 400

Thr Leu Ala Val Val Ala Leu Phe Ala Asp Gly Pro Thr Ala Ile Arg
                405                 410                 415

Asp Val Ala Ser Trp Arg Val Lys Glu Thr Glu Arg Met Val Ala Ile
            420                 425                 430

Arg Thr Glu Leu Thr Lys Leu Gly Ala Thr Val Glu Glu Gly Pro Asp
        435                 440                 445

Tyr Cys Ile Ile Thr Pro Pro Glu Lys Leu Asn Ile Thr Ala Ile Asp
    450                 455                 460

Thr Tyr Asp Asp His Arg Met Ala Met Ala Phe Ser Leu Ala Ala Cys
465                 470                 475                 480

Ala Glu Val Pro Val Thr Ile Arg Asp Pro Gly Cys Thr Arg Lys Thr
                485                 490                 495

```
Phe Pro Asn Tyr Phe Asp Val Leu Ser Thr Phe Val Lys Asn
            500                 505                 510
```

<210> SEQ ID NO 20
<211> LENGTH: 515
<212> TYPE: PRT
<213> ORGANISM: Oryza sativa

<400> SEQUENCE: 20

```
Met Ala Ala Thr Met Ala Ser Asn Ala Ala Ala Ala Ala Val Ser
1               5                   10                  15

Leu Asp Gln Ala Val Ala Ala Ser Ala Ala Phe Ser Ser Arg Lys Gln
                20                  25                  30

Leu Arg Leu Pro Ala Ala Arg Gly Gly Met Arg Val Arg Val Arg
        35                  40                  45

Ala Arg Gly Arg Arg Glu Ala Val Val Ala Ser Ala Ser Ser Ser
        50                  55                  60

Ser Val Ala Ala Pro Ala Ala Lys Ala Glu Glu Ile Val Leu Gln Pro
65                  70                  75                  80

Ile Arg Glu Ile Ser Gly Ala Val Gln Leu Pro Gly Ser Lys Ser Leu
                85                  90                  95

Ser Asn Arg Ile Leu Leu Leu Ser Ala Leu Ser Glu Gly Thr Thr Val
                100                 105                 110

Val Asp Asn Leu Leu Asn Ser Glu Asp Val His Tyr Met Leu Glu Ala
                115                 120                 125

Leu Lys Ala Leu Gly Leu Ser Val Glu Ala Asp Lys Val Ala Lys Arg
            130                 135                 140

Ala Val Val Gly Cys Gly Gly Lys Phe Pro Val Glu Lys Asp Ala
145                 150                 155                 160

Lys Glu Glu Val Gln Leu Phe Leu Gly Asn Ala Gly Thr Ala Met Arg
                165                 170                 175

Pro Leu Thr Ala Ala Val Thr Ala Ala Gly Gly Asn Ala Thr Tyr Val
            180                 185                 190

Leu Asp Gly Val Pro Arg Met Arg Glu Arg Pro Ile Gly Asp Leu Val
        195                 200                 205

Val Gly Leu Lys Gln Leu Gly Ala Asp Val Asp Cys Phe Leu Gly Thr
210                 215                 220

Glu Cys Pro Pro Val Arg Val Lys Gly Ile Gly Gly Leu Pro Gly Gly
225                 230                 235                 240

Lys Val Lys Leu Ser Gly Ser Ile Ser Ser Gln Tyr Leu Ser Ala Leu
                245                 250                 255

Leu Met Ala Ala Pro Leu Ala Leu Gly Asp Val Glu Ile Glu Ile Ile
            260                 265                 270

Asp Lys Leu Ile Ser Ile Pro Tyr Val Glu Met Thr Leu Arg Leu Met
        275                 280                 285

Glu Arg Phe Gly Val Lys Ala Glu His Ser Asp Ser Trp Asp Arg Phe
    290                 295                 300

Tyr Ile Lys Gly Gly Gln Lys Tyr Lys Ser Pro Gly Asn Ala Tyr Val
305                 310                 315                 320

Glu Gly Asp Ala Ser Ser Ala Ser Tyr Phe Leu Ala Gly Ala Ala Ile
                325                 330                 335

Thr Gly Gly Thr Val Thr Val Gln Gly Cys Gly Thr Thr Ser Leu Gln
            340                 345                 350

Gly Asp Val Lys Phe Ala Glu Val Leu Glu Met Met Gly Ala Lys Val
        355                 360                 365
```

```
Thr Trp Thr Asp Thr Ser Val Thr Val Thr Gly Pro Pro Arg Glu Pro
    370                 375                 380

Tyr Gly Lys Lys His Leu Lys Ala Val Asp Val Asn Met Asn Lys Met
385                 390                 395                 400

Pro Asp Val Ala Met Thr Leu Ala Val Val Ala Leu Phe Ala Asp Gly
                405                 410                 415

Pro Thr Ala Ile Arg Asp Val Ala Ser Trp Arg Val Lys Glu Thr Glu
                420                 425                 430

Arg Met Val Ala Ile Arg Thr Glu Leu Thr Lys Leu Gly Ala Ser Val
            435                 440                 445

Glu Glu Gly Pro Asp Tyr Cys Ile Ile Thr Pro Glu Lys Leu Asn
    450                 455                 460

Ile Thr Ala Ile Asp Thr Tyr Asp Asp His Arg Met Ala Met Ala Phe
465                 470                 475                 480

Ser Leu Ala Ala Cys Ala Asp Val Pro Val Thr Ile Arg Asp Pro Gly
                485                 490                 495

Cys Thr Arg Lys Thr Phe Pro Asn Tyr Phe Asp Val Leu Ser Thr Phe
                500                 505                 510

Val Arg Asn
    515

<210> SEQ ID NO 21
<211> LENGTH: 514
<212> TYPE: PRT
<213> ORGANISM: Artificial Sequence
<220> FEATURE:
<223> OTHER INFORMATION: Consensus sequence
<220> FEATURE:
<221> NAME/KEY: misc_feature
<222> LOCATION: (1)..(4)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: Xaa can be any naturally occurring amino acid
<220> FEATURE:
<221> NAME/KEY: misc_feature
<222> LOCATION: (14)..(15)
<223> OTHER INFORMATION: Xaa can be any naturally occurring amino acid
<220> FEATURE:
<221> NAME/KEY: misc_feature
<222> LOCATION: (19)..(20)
<223> OTHER INFORMATION: Xaa can be any naturally occurring amino acid
<220> FEATURE:
<221> NAME/KEY: misc_feature
<222> LOCATION: (22)..(23)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (39)..(39)
<223> OTHER INFORMATION: Xaa can be any naturally occurring amino acid
<220> FEATURE:
<221> NAME/KEY: misc_feature
<222> LOCATION: (41)..(42)
<223> OTHER INFORMATION: Xaa can be any naturally occurring amino acid
<220> FEATURE:
```

```
<221> NAME/KEY: misc_feature
<222> LOCATION: (46)..(46)
<223> OTHER INFORMATION: Xaa can be any naturally occurring amino acid
<220> FEATURE:
<221> NAME/KEY: misc_feature
<222> LOCATION: (49)..(49)
<223> OTHER INFORMATION: Xaa can be any naturally occurring amino acid
<220> FEATURE:
<221> NAME/KEY: misc_feature
<222> LOCATION: (52)..(52)
<223> OTHER INFORMATION: Xaa can be any naturally occurring amino acid
<220> FEATURE:
<221> NAME/KEY: misc_feature
<222> LOCATION: (56)..(58)
<223> OTHER INFORMATION: Xaa can be any naturally occurring amino acid
<220> FEATURE:
<221> NAME/KEY: misc_feature
<222> LOCATION: (60)..(60)
<223> OTHER INFORMATION: Xaa can be any naturally occurring amino acid
<220> FEATURE:
<221> NAME/KEY: misc_feature
<222> LOCATION: (62)..(62)
<223> OTHER INFORMATION: Xaa can be any naturally occurring amino acid
<220> FEATURE:
<221> NAME/KEY: misc_feature
<222> LOCATION: (65)..(67)
<223> OTHER INFORMATION: Xaa can be any naturally occurring amino acid
<220> FEATURE:
<221> NAME/KEY: misc_feature
<222> LOCATION: (69)..(70)
<223> OTHER INFORMATION: Xaa can be any naturally occurring amino acid
<220> FEATURE:
<221> NAME/KEY: misc_feature
<222> LOCATION: (76)..(76)
<223> OTHER INFORMATION: Xaa can be any naturally occurring amino acid
<220> FEATURE:
<221> NAME/KEY: misc_feature
<222> LOCATION: (225)..(225)
<223> OTHER INFORMATION: Xaa can be any naturally occurring amino acid
<220> FEATURE:
<221> NAME/KEY: misc_feature
<222> LOCATION: (231)..(232)
<223> OTHER INFORMATION: Xaa can be any naturally occurring amino acid
<220> FEATURE:
<221> NAME/KEY: misc_feature
<222> LOCATION: (255)..(255)
<223> OTHER INFORMATION: Xaa can be any naturally occurring amino acid
<220> FEATURE:
<221> NAME/KEY: misc_feature
<222> LOCATION: (278)..(278)
<223> OTHER INFORMATION: Xaa can be any naturally occurring amino acid
<220> FEATURE:
<221> NAME/KEY: misc_feature
<222> LOCATION: (344)..(344)
<223> OTHER INFORMATION: Xaa can be any naturally occurring amino acid
<220> FEATURE:
<221> NAME/KEY: misc_feature
<222> LOCATION: (383)..(383)
<223> OTHER INFORMATION: Xaa can be any naturally occurring amino acid
<220> FEATURE:
<221> NAME/KEY: misc_feature
<222> LOCATION: (486)..(486)
<223> OTHER INFORMATION: Xaa can be any naturally occurring amino acid

<400> SEQUENCE: 21

Xaa Xaa Xaa Xaa Met Ala Xaa Xaa Ala Xaa Ala Ala Xaa Xaa Ser
1               5                   10                  15

Leu Asp Xaa Xaa Ser Xaa Xaa Arg Ala Ala Phe Xaa His Arg Arg Arg
            20                  25                  30

Leu Arg Xaa Pro Ala Ala Xaa Arg Xaa Xaa His Arg Gly Xaa Val Arg
            35                  40                  45

Xaa Arg Gly Xaa Arg Glu Ala Xaa Xaa Xaa Ala Xaa Ala Xaa Ser Ser
        50                  55                  60

Xaa Xaa Xaa Ala Xaa Xaa Ala Gly Ala Glu Glu Xaa Val Leu Gln Pro
```

```
                65                  70                  75                  80
Ile Arg Glu Ile Ser Gly Ala Val Gln Leu Pro Gly Ser Lys Ser Leu
                    85                  90                  95

Ser Asn Arg Ile Leu Leu Leu Ser Ala Leu Ser Glu Gly Thr Thr Val
                100                 105                 110

Val Asp Asn Leu Leu Asn Ser Glu Asp Val His Tyr Met Leu Glu Ala
                115                 120                 125

Leu Glu Ala Leu Gly Leu Ser Val Glu Ala Asp Lys Val Ala Lys Arg
                130                 135                 140

Ala Val Val Gly Cys Gly Arg Phe Pro Val Glu Lys Asp Ala
145                 150                 155                 160

Lys Glu Glu Val Gln Leu Phe Leu Gly Asn Ala Gly Thr Ala Met Arg
                165                 170                 175

Pro Leu Thr Ala Ala Val Thr Ala Ala Gly Gly Asn Ala Thr Tyr Val
                180                 185                 190

Leu Asp Gly Val Pro Arg Met Arg Glu Arg Pro Ile Gly Asp Leu Val
                195                 200                 205

Val Gly Leu Gln Gln Leu Gly Ala Asp Val Asp Cys Phe Leu Gly Thr
                210                 215                 220

Xaa Cys Pro Pro Val Arg Xaa Xaa Gly Ile Gly Gly Leu Pro Gly Gly
225                 230                 235                 240

Lys Val Lys Leu Ser Gly Ser Ile Ser Ser Gln Tyr Leu Ser Xaa Leu
                245                 250                 255

Leu Met Ala Ala Pro Leu Ala Leu Glu Asp Val Glu Ile Glu Ile Ile
                260                 265                 270

Asp Lys Leu Ile Ser Xaa Pro Tyr Val Glu Met Thr Leu Arg Leu Met
                275                 280                 285

Glu Arg Phe Gly Val Lys Ala Glu His Ser Asp Ser Trp Asp Arg Phe
                290                 295                 300

Tyr Ile Lys Gly Gly Gln Lys Tyr Lys Ser Pro Gly Asn Ala Tyr Val
305                 310                 315                 320

Glu Gly Asp Ala Ser Ser Ala Ser Tyr Phe Leu Ala Gly Ala Ala Ile
                325                 330                 335

Thr Gly Gly Thr Val Thr Val Xaa Gly Cys Gly Thr Thr Ser Leu Gln
                340                 345                 350

Gly Asp Val Lys Phe Ala Glu Val Leu Glu Met Met Gly Ala Lys Val
                355                 360                 365

Thr Trp Thr Asp Thr Ser Val Thr Val Thr Gly Pro Pro Arg Xaa Pro
                370                 375                 380

Gly Arg Lys His Leu Lys Ala Val Asp Val Asn Met Asn Lys Met Pro
385                 390                 395                 400

Asp Val Ala Met Thr Leu Ala Val Ala Leu Phe Ala Asp Gly Pro
                405                 410                 415

Thr Ala Ile Arg Asp Val Ala Ser Trp Arg Val Lys Glu Thr Glu Arg
                420                 425                 430

Met Val Ala Ile Arg Thr Glu Leu Thr Lys Leu Gly Ala Ser Val Glu
                435                 440                 445

Glu Gly Pro Asp Tyr Cys Ile Ile Thr Pro Pro Glu Lys Leu Asn Ile
                450                 455                 460

Thr Ala Ile Asp Thr Tyr Asp Asp His Arg Met Ala Met Ala Phe Ser
465                 470                 475                 480
```

-continued

```
Leu Ala Ala Cys Ala Xaa Val Pro Val Thr Ile Arg Asp Pro Gly Cys
                485                 490                 495

Thr Arg Lys Thr Phe Pro Asn Tyr Phe Asp Val Leu Ser Thr Phe Val
            500                 505                 510

Arg Asn
```